(12) United States Patent
Satya et al.

(10) Patent No.: US 6,528,818 B1
(45) Date of Patent: Mar. 4, 2003

(54) TEST STRUCTURES AND METHODS FOR INSPECTION OF SEMICONDUCTOR INTEGRATED CIRCUITS

(75) Inventors: Akella V. S. Satya, Milpitas, CA (US); Gustavo A. Pinto, Belmont, CA (US); David L. Adler, San Jose, CA (US); Robert Thomas Long, Santa Cruz, CA (US); Neil Richardson, Palo Alto, CA (US); Kurt H. Weiner, San Jose, CA (US); David J. Walker, Sunol, CA (US); Lynda C. Mantalas, Campbell, CA (US)

(73) Assignee: KLA-Tencor, San Jose, CA (US)

( * ) Notice: Subject to any disclaimer, the term of this patent is extended or adjusted under 35 U.S.C. 154(b) by 0 days.

(21) Appl. No.: 09/648,380

(22) Filed: Aug. 25, 2000

Related U.S. Application Data

(60) Provisional application No. 60/170,655, filed on Dec. 14, 1999, and provisional application No. 60/197,512, filed on Apr. 18, 2000.

(51) Int. Cl.$^7$ .............................................. H01L 23/58
(52) U.S. Cl. ........................................ 257/48; 257/758
(58) Field of Search ................. 257/48, 758; 324/751

(56) References Cited

U.S. PATENT DOCUMENTS

| | | |
|---|---|---|
| 4,644,172 A | 2/1987 | Sandland et al. ............ 250/548 |
| 4,868,492 A * | 9/1989 | Beha et al. .................... 324/73 |
| 4,902,967 A | 2/1990 | Flesner ....................... 324/158 |
| 5,489,852 A | 2/1996 | Gomez ........................ 324/754 |
| 5,502,306 A | 3/1996 | Meisburger et al. ......... 250/310 |
| 5,514,974 A * | 5/1996 | Bouldin ....................... 324/763 |
| 5,537,669 A | 7/1996 | Evans et al. ................. 382/141 |
| 5,578,821 A | 11/1996 | Meisberger et al. ......... 250/310 |
| 5,665,968 A | 9/1997 | Meisberger et al. ......... 250/310 |
| 5,717,204 A | 2/1998 | Meisburger et al. ......... 250/310 |
| 5,804,459 A | 9/1998 | Bolam et al. .................. 453/12 |
| 5,959,459 A | 9/1999 | Satya et al. .................. 324/751 |
| 6,021,214 A | 2/2000 | Evans et al. ................. 382/141 |
| 6,061,814 A | 5/2000 | Sugasawara ................. 714/724 |
| 6,091,249 A | 7/2000 | Talbot et al. ................ 324/751 |
| 6,252,412 B1 | 6/2001 | Talbot et al. ................ 324/750 |
| 6,265,232 B1 | 7/2001 | Simmons ...................... 434/14 |
| 6,292,582 B1 | 9/2001 | Lin et al. ..................... 382/149 |
| 6,324,298 B1 | 11/2001 | O'Dell et al. ................ 382/149 |
| 6,344,750 B1 | 2/2002 | Lo et al. ...................... 324/751 |

FOREIGN PATENT DOCUMENTS

| | | | |
|---|---|---|---|
| EP | 0 853 243 A2 | 7/1998 | ......... G01R/31/307 |
| EP | 0 892 275 A2 | 1/1999 | ......... G01R/31/305 |
| WO | WO 99/22310 | 5/1999 | ........... G06F/17/00 |
| WO | WO 99/22311 | 5/1999 | ........... G06F/17/00 |

OTHER PUBLICATIONS

Tugbawa, et al, "Pattern And Process Dependencies In Copper Damascene Chemical Mechanical Polishing Processes," Jun. 1998, VLSI Multilevel Interconnect conference (VMIC).

Park et al, "Multi–Level Pattern Effects In Copper CMP," Oct. 1999, CMP Symposium Electrochemical Society Meeting.

* cited by examiner

*Primary Examiner*—Phat X. Cao
(74) *Attorney, Agent, or Firm*—Beyer, Weaver & Thomas, LLP.; Mary R. Olynick, Esq.

(57) ABSTRACT

Disclosed is a semiconductor die having a scanning area. The semiconductor die includes a first plurality of test structures wherein each of the test structures in the first plurality of test structures is located entirely within the scanning area. The semiconductor die further includes a second plurality of test structures wherein each of the test structures in the first plurality of test structures is located only partially within the scanning area. The test structures are arranged so that a scan of the scanning area results in detection of defects outside of the scanning area.

19 Claims, 35 Drawing Sheets

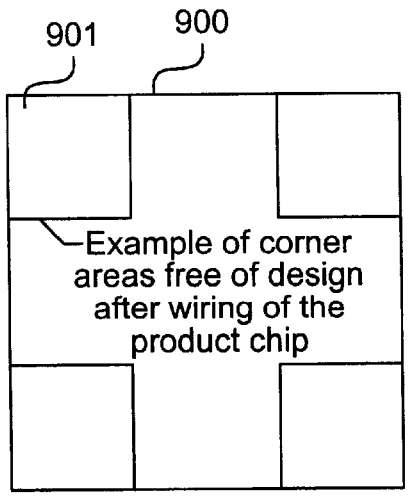
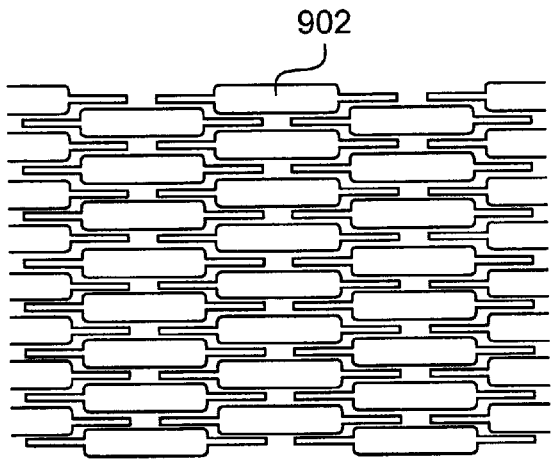
FIG. 26A
FIG. 26B
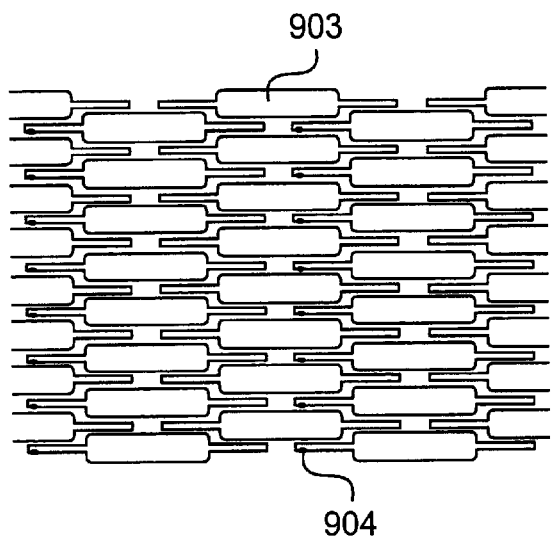
FIG. 26C

TEST STRUCTURES AND METHODS FOR INSPECTION OF SEMICONDUCTOR INTEGRATED CIRCUITS

CROSS REFERENCE TO RELATED PATENT APPLICATION

This application claims the benefit of U.S. Provisional Application No. 60/170,655 filed on Dec. 14, 1999, the disclosure of which is incorporated herein by reference.

This application claims the benefit of U.S. Provisional Application No. 60/197,512 filed on Apr. 18, 2000, the disclosure of which is incorporated herein by reference.

This application is related to concurrently filed U.S. patent applications having application Nos. 09/648,380, 09/648,109, 09/648,094, 09/648,212, 09/648,095, 09/648,381, 09/648,096 09/648,379 and 09/648,092.

BACKGROUND OF THE INVENTION

1. Field of the Invention

The present invention generally relates to the field of inspection and analysis of specimens and, more particularly, to defect inspection and analysis of semiconductor integrated circuits.

2. Description of the Prior Art

In the semiconductor integrated circuit (IC) industry, there is a continuing demand for higher circuit packing densities. This demand of increased packing densities has led the semiconductor industry to develop new materials and processes to achieve sub-micron device dimensions. Manufacturing IC's at such minute dimensions adds more complexity to circuits and the demand for improved methods to inspect integrated circuits in various stages of their manufacture is ever present.

Although inspection of such products at various stages of manufacture is very important and can significantly improve production yield and product reliability, the increased complexity of IC's increases the cost of such inspections, both in terms of expense and time. However, if a defect can be detected early in production, the cause of the defect can be determined and corrected before a significant number of defective IC's are manufactured.

In order to overcome the problems posed by defective IC's, IC manufacturers sometimes fabricate semiconductor defect test structures. Such defect test structures are dedicated to defect analysis. The defect test structures are fabricated such that they are sensitive to defects that occur in IC product, but are designed so that the presence of defects is more readily ascertained. Such defect test structures are often constructed on the same semiconductor substrate as the IC products.

One example of a defect test structure is found in the Copper CMP Test Mask Set designed at MIT. This test mask set is designed to quantify the dependence of the resulting copper line profile on parameters such as line pitch, line width and line aspect ratio. However, the MIT mask set is designed to be probed using conventional electrical testing in which current is passed through the device by contacting predefined pad of large area (approximately 100×100 $\mu m^2$) with electrical probes, not by electron beam. As is well known in the art, defect detecting systems frequently utilize charged particle beams. In such systems, a charged particle beam, such as an electron beam, is irradiated on defect test structures. The interaction of the electron beam with features in the circuitry generates a number of signals in varying intensities, such as secondary electrons, back-scattered electrons, x-rays, etc. Typically, electron beam methods employ secondary electron signals for the well known "voltage contrast" technique for circuit defect detection.

The voltage contrast technique operates on the basis that potential differences in the various locations of a test structure under examination cause differences in secondary electron emission intensities. Thus, the potential state of the scanned area is acquired as a voltage contrast image such that a low potential portion of, for example, a wiling pattern might be displayed as bright (intensity of the secondary electron emission is high) and a high potential portion might be displayed as dark (lower intensity secondary electron emission). Alternatively, the system may be configured such that a low potential portion might be displayed as dark and a high potential portion might be displayed as bright.

A secondary electron detector is used to measure the intensity of the secondary electron emission that originates only at the path swept by the scanning electron beam. A defective portion can be identified from the potential state of the portion under inspection. In one form of inspection, the mismatched portion between the defective voltage contrast image and the defect free one reveals the defect location.

Thus, in such systems, the voltage contrast is simultaneously monitored for both defective and defect free circuits for each circuit manufactured. However, considering the density of IC's currently produced, the time necessary to scan voltage contrast data to perform comparisons is significant. The inspection and analysis of such circuits may take several days. Accordingly, more efficient voltage contrast inspection systems are desirable.

SUMMARY

The present invention includes a system for detecting defects in test structures. The system operates so as to provide efficient and effective testing of defects. It also includes novel test structures that provide for improved defect testing, as are described more fully below.

In one embodiment, a semiconductor die having a scanning area is disclosed. The semiconductor die includes a first plurality of test structures wherein each of the test structures in the first plurality of test structures is located entirely within the scanning area. The semiconductor die further includes a second plurality of test structures wherein each of the test structures in the first plurality of test structures is located only partially within the scanning area. The test structures are arranged so that a scan of the scanning area results in detection of defects outside of the scanning area. In a preferred embodiment, the second plurality of test structures include test structures that are primarily located outside the scanning area. In another aspect, the second plurality of test structures are arranged such that a short associated with a portion of the second plurality of test structures that is located outside the scanning area is detectable by performing voltage contrast on a portion of the second plurality of test structures that is located within the scanning area. In a specific implementation, the first plurality of test structures include a mix of test structure types, and these test structures include a first type of test structure and a second type of test structure. The first type differs from the second type, and the first and second test structures may be a via chain test structure, a chemical mechanical polishing (CMP) test structure, a contact array test structure, a test structure for measuring misalignment, or a CMP dummy metal filler test structure.

In another embodiment, a semiconductor die has at least one electrically isolated conductive test structure positioned adjacent to at least one electrically non-isolated conductive test structures. A first portion of the electrically isolated test structure is located with in a scanning area, and a second portion of the electrically isolated test structure is located outside the scanning are so that a short between the second portion of the electrically isolated test structure and the electrically non-isolated test structure is detectable through voltage contrast on the first portion of the at least one electrically isolated test structure. In a preferred embodiment, a width of the first portion of the electrically non-isolated test structure is substantially equal to or less than a width of the second portion of the electrically non-isolated test structure.

In yet another embodiment, a semiconductor die includes at least one electrically non-isolated conductive test structure. A first portion of the electrically non-isolated test structure is located within a scanning area, and a second portion of the electrically non-isolated test structure is located outside the scanning area so that an open type defect within the at least one electrically non-isolated test structure is detectable through voltage contrast on the first portion of the electrically isolated test structure. Also, a width of the first portion of the electrically non-isolated test structure is substantially equal to or less than a width of the second portion.

These and other features and advantages of the present invention will be presented in more detail in the following specification of the invention and the accompanying figures which illustrate by way of example the principles of the invention.

BRIEF DESCRIPTION OF THE DRAWINGS

FIGS. 26a through 26c illustrate the process for utilizing dummy shapes for purposes of testing for defects.

DESCRIPTION OF SPECIFIC EMBODIMENT(S)

Figure 1:
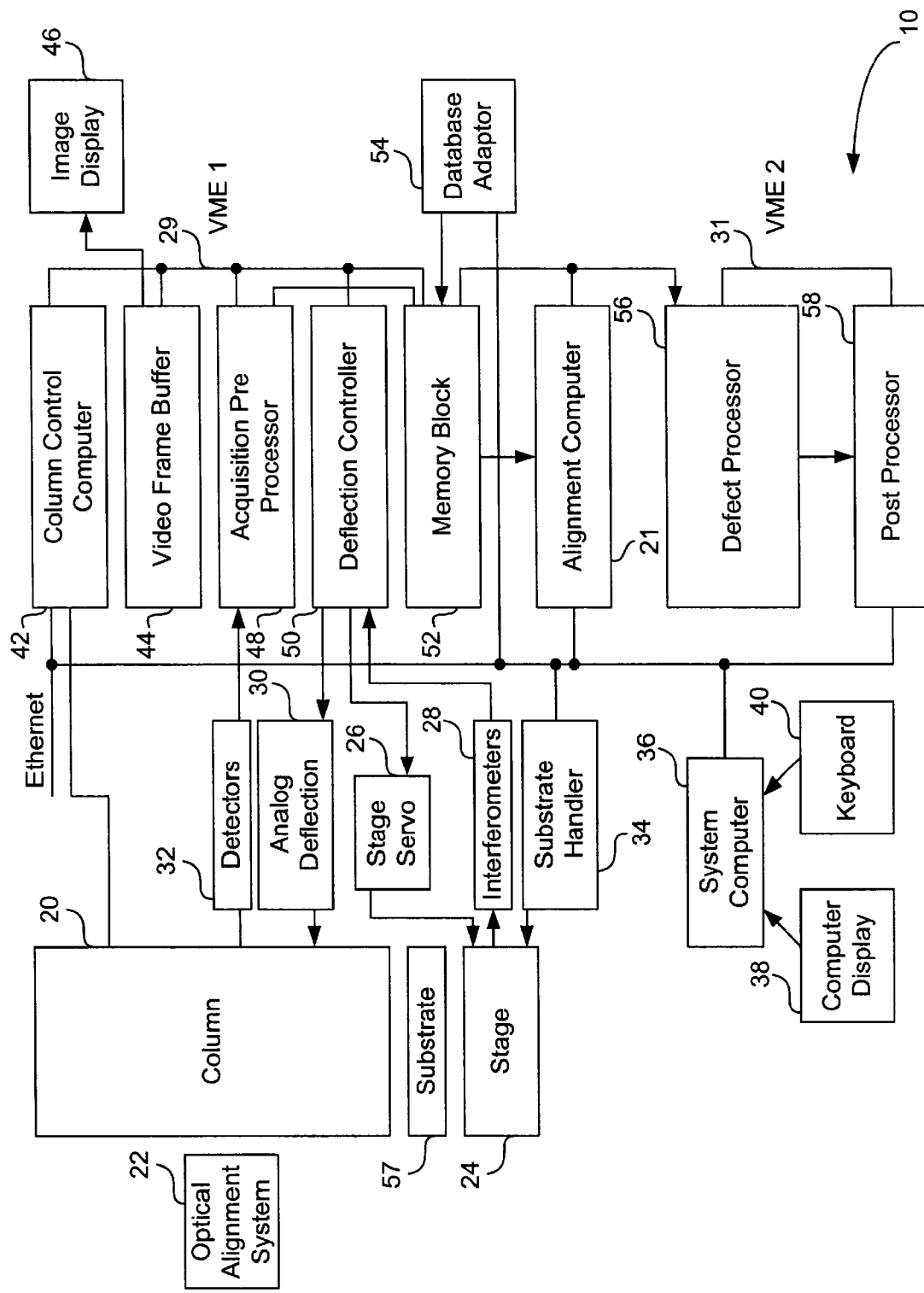
FIG. 1 illustrates a block diagram of an SEM inspection system in accordance with one embodiment of the present invention.

As will be further described below, the preferred embodiment of the present invention provides automated, rapid, contactless wafer inspection capabilities in order to detect, isolate and characterize electrical defects impacting integrated circuits.

Several embodiments of the present invention are described herein in the context of exemplary multilevel integrated circuit structures, including semiconductor structures and overlying metallization or other interconnects, using various levels of conductors that are separated from each other and the substrate by dielectric layers. However, structures formed using other methods of semiconductor fabrication also fall within the scope of the present invention.

One application of the present invention includes the operation of a scanning electron microscope (SEM) with a continuously moving stage. However, the test structures and many of the methods described herein are also useful in the context of other testing devices, including SEM's operated in step and repeat mode. As an alternative to moving the stage with respect to the beam, the beam may be moved by deflecting the field of view with an electromagnetic lens. Alternatively, the beam column may be moved with respect to the stage.

A. Utilization of Scanning Electron Microscope with Continuously Moving Stage for Scanning Primary Area The present invention, in one embodiment, utilizes an SEM with a continuously moving stage. Use of such an SEM provides significant advantages in connection with the detection of defects in semiconductor devices, as is described more fully below.

An SEM system may be used to provide automatic inspection of wafers and other substrates. Such SEM systems are well known in the art. For example, U.S. Pat. No. 5,578,821, issued to Meisburger et al. on Nov. 26, 1996 and entitled "ELECTRON BEAM INSPECTION SYSTEM AND METHOD," describes an apparatus for a charged particle scanning system and an automatic inspection system, including wafers used in microcircuit fabrication. This patent is herein incorporated by reference in its entirety. In the Meisburger apparatus, a charged particle beam is directed at the surface of a substrate for scanning that substrate and a selection of detectors are included to detect at least one of the secondary charged particles, back-scattered charged particles and transmitted charged particles from the substrate.

The substrate is mounted on an x-y stage to provide at least one degree of freedom in movement while the substrate is being scanned by the charged particle beam. The substrate may also be subjected to an electric field on or near its surface to accelerate the secondary charged particles. The system facilitates inspection at low beam energies on charge sensitive insulating substrates and has the capability to accurately measure the position of the substrate with respect to the charged particle beam.

Additionally, there is an optical alignment system for initially aligning the substrate beneath the charged particle beam. To function most efficiently there is also a vacuum system for evacuating and repressurizing a chamber containing the substrate. The vacuum system can be used to hold one substrate at vacuum while a second one is being loaded/unloaded, evacuated or repressurized. In the inspection configuration, there is also a comparison system for comparing the pattern on the substrate with a second pattern.

The '821 patent further describes an automatic system for the automatic inspection of a substantially non-conductive substrate. The system includes a field emission electron source to provide an electron beam, a charged particle beam column to deliver and scan the electron beam from the field emission electron source on a surface of the substrate, one or more charged particle detector(s) to detect one or more of three types of charged particles emanating from the top and bottom surfaces of the substrate, (namely, secondary charged particles, back-scattered charged particles and transmitted charged particles). The system also includes a continuously moving x-y stage disposed to receive the substrate and to provide at least one degree of motion to the substrate while the substrate is being scanned by the charged particle beam and a multi-processor image defect computer coupled to the charged particle detector(s) to identify defects on the substrate. Such a system is suitable for practicing the preferred embodiment of the present invention.

Similarly, U.S. Pat. No. 5,502,306, issued to Meisburger et al. on Mar. 26, 1996, entitled "ELECTRON BEAM INSPECTION SYSTEM AND METHOD," describes an inspection system suitable for practice of the present invention. In the '306 patent, numerous embodiments of a method and apparatus for a particle scanning system and an automatic inspection system suitable for practice of the preferred embodiment of the present invention are described. Applicants incorporate herein this reference U.S. Pat. No. 5,502,306 in its entirety.

The inspection system utilized in the practice of the present invention can operate in several modes, including, for example, array, die-to-die and die-to-database. In each of these modes, defects are detected by comparing an electron beam image derived from scanning the substrate against a standard. In array mode, signals from a first portion of an array of substantially identical circuit elements are compared with signals from a second portion of such an array. In a variation on this technique, an image of the array can be compared with an electronically modified version of the same image, and the repeating content can be subtracted. A resulting difference image will show the defects. An example of such a system is shown in commonly assigned U.S. Pat. No. 5,537,669, issued to Evans et al. on Jul. 16, 1996, entitled "INSPECTION METHOD AND APPARATUS FOR THE INSPECTION OF EITHER RANDOM OR REPEATING PATTERNS," which patent is incorporated herein by reference in its entirety.

In die-to-die inspection, signals from two die of the same substrate are compared with each other. In die-to-database inspection the signal from one die derived from the electron microscope is compared with a signal that is derived from the database. The database may include design data that is used to make the die and to generate a plurality of perfect images of how the die would appear without any defects. For example, each image contains voltage contrast signatures specifying how the corresponding test image should appear without defects. The perfect images are compared to corresponding images obtained from the die. Alternatively, the database may include the plurality of perfect images themselves. In the case of die-to-die inspection, the function of the defect processor is to compare image data obtained from a first die with image data obtained from a second die, or, in the case of die-to-database inspection, to compare image data obtained from a die with data derived from a database adapter. Preferably, the defect processor is a multi-pixel image computer that allows efficient comparisons to take place. In a specific embodiment, the processor operates with pixel resolution sizes in a range of about 25 nm to 2000 nm. in more general terms, the processor operates with a pixel size nominally equivalent to two times a width of the test structure line width to maximize throughput at optimal signal to noise sensitivity. The routines and the basic implementation of a defect processor are described in U.S. Pat. No. 4,644,172, issued to Sandland et al. on Feb. 17, 1987, entitled "ELECTRONIC CONTROL OF AN AUTOMATIC WAFER INSPECTION SYSTEM," which patent is incorporated herein by reference in its entirety. Other inventive inspection techniques (e.g., die-to-truth table and die-to-perfect image) are also described below.

The sample to be inspected may be supported by a holder that is placed beneath an electron beam column on an x-y stage. The sample should be aligned on the stage such that the x-directional motion of the stage is substantially parallel to the x-axis of the core area of the sample patterns, i.e., the area of interest for the inspection. Once the sample is properly aligned, the inspection process is initiated.

The column and an analog deflection circuit direct an electron beam towards the sample surface, and the detector (s) may detect one or more of the secondary electrons, back-scattered electrons, and transmitted electrons. The position and movement of the stage during the inspection of the sample is controlled by a stage servo.

FIG. 1 provides an overall block diagram of an inspection system 10 suitable for practice of one embodiment of the present invention. In system 10 an automatic inspection apparatus of X-ray masks, wafers, and other samples, is shown which uses a scanning electron microscope as its sensor.

Sample 57 to be inspected is held in a holder which is automatically placed beneath electron beam column 20 on x-y stage 24 by sample handler 34. This is accomplished by commanding sample handler 34 by system computer 36 to remove the sample 57 of interest from a cassette with the flat or notch (see FIG. 4a) on sample 57 being detected automatically to properly orient the sample 57 in handler 34. The sample is then loaded under column 20. Next, the operator visually observes the mask through optical alignment system 22 to locate the alignment points on the sample (these may be any operator selected features on the sample) to ensure that the x-directional motion of the stage is substantially parallel to the x-axis of the care area of the sample patterns, i.e., the area of interest for the inspection. That completes the coarse alignment.

Fine alignment is subsequently achieved by the operator scanning the sample with the electron beam and observing the image on image display 46. All alignment data is then stored in alignment computer 21 which works in cooperation with system computer 36 for calculation of the actual combined x and y motions necessary to scan the die along its x and y axes so that no further operator alignment action is required for inspections of the same type of samples. Once the sample is properly aligned, the inspection process is initiated.

Column 20 and its optical alignment system 22 and analog deflection circuit 30 (as described more completely below) then direct an electron beam towards sample surface 57, and detectors 32 detect the secondary electrons, the back-scattered electrons and those electrons which pass through sample 57. That operation and the data collection from that exposure is performed by column control computer 42, video frame buffer 44, acquisition pre-processor 48, deflection controller 50, memory block 52. Bus VME1 29, serves as the communication link between the subsystems.

The position and movement of stage 24 during the inspection of sample 57 is controlled by stage servo 26 and interferometers 28 under the control of deflection controller 50 and alignment computer 21.

When the comparison mode is die-to-database, database adapter 54 in communication with memory block 52 is used as a source of the signal that is equivalent to the expected die format.

The actual defect processing is performed on the data in memory block 52 by defect processor 56 in conjunction with post processor 58, with the communication between these blocks being via bus VME2 31.

The overall operation of the system is performed by system computer 36, user keyboard 40 and computer display 38 in communication with the other blocks via a data bus 23 which may be similar to an Ethernet bus. (Ethernet is a trademark of Xerox Corp.).

In one embodiment of the invention, significant benefits are achieved by scanning with a continuously moving stage. That is, measurements of the sample are obtained while the stage (or beam) is moving. In contrast, stepper type systems utilize alternating cycles of movement and measurement of the sample. Additionally, stepper type systems require time to settle after each movement before measurements of the sample can be taken. The illustrated embodiment provides a more efficient mechanisms for taking measurements during movement of the sample without requiring any settle periods.

In the illustrated embodiment, the stage moves continuously in the x-direction. More preferably, the stage moves continuously at a constant speed in the x-direction. Typical speeds of the continuous movement of the stage are approximately 1.0 to 200 mm per second. Note that movement in the x-direction can also be achieved by movement of the e-beam, whether by movement of the actual e-beam column or by deflection of the beam rather than the stage. Moreover, the stage itself can operate such that it moves in both the x- and y-directions or a combination thereof.

Simultaneously with the continuous movement of the stage in the x-direction, the electron beam is repeatedly deflected back and forth in the y-direction. During a typical application of the present invention, the e-beam may move back and forth at approximately 100 kHz. Preferably, the deflection is largely free of distortion and is substantially perpendicular to the surface, so that the imaging characteristics are uniform over the scan field.

Figure 2:
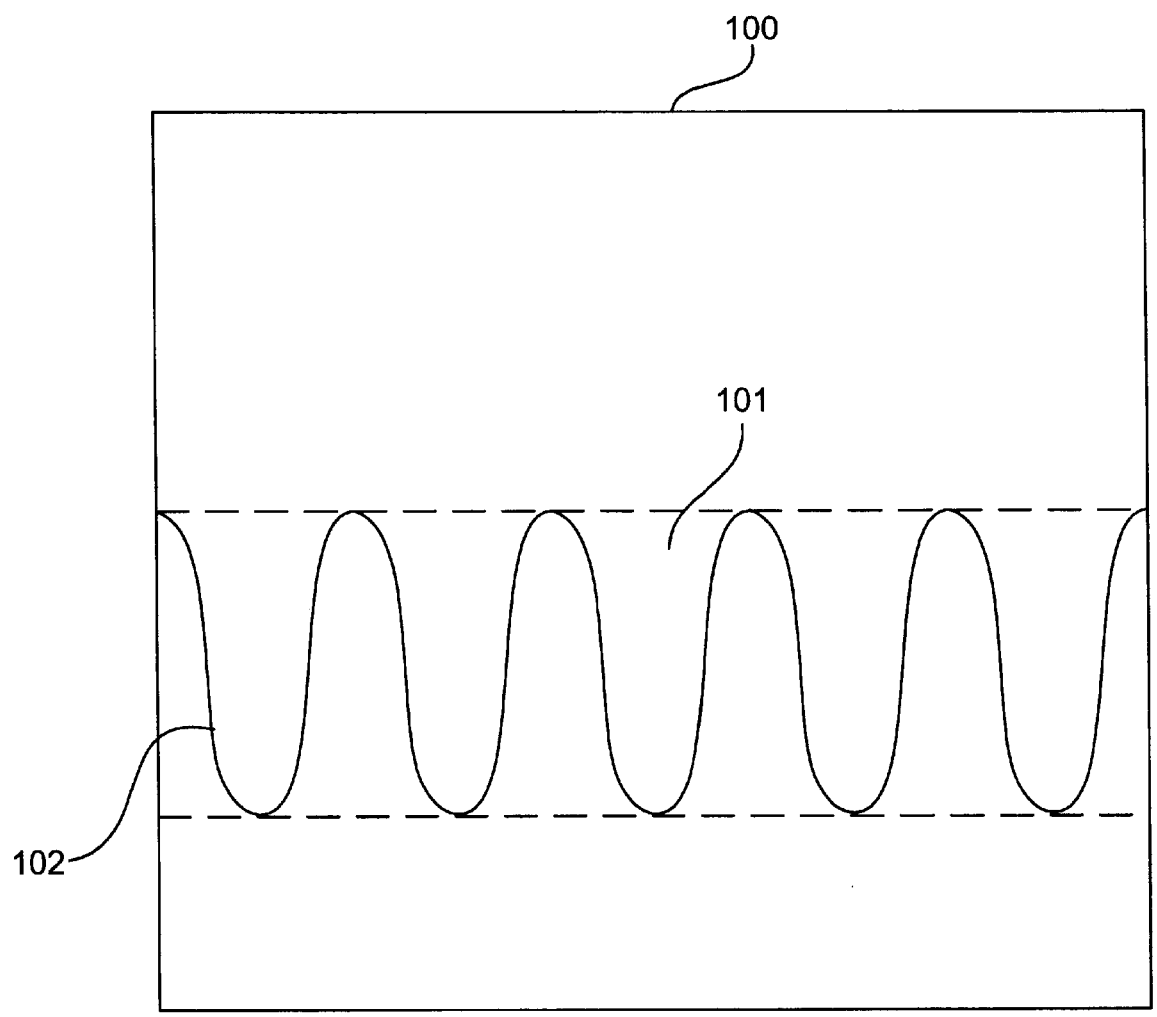
FIG. 2 illustrates the typical scan pattern of the present invention.

FIG. 2 illustrates a scan pattern. Here a single test chip 100 is shown on a substrate. Within the test chip there is a scanned swath (or "area of significance" or "primary scan area") 101 that is to be inspected. During the inspection of the die, the effective scanning motion in the x-direction is provided by a moving stage and the effective motion in the y-direction is provided by deflection of the electron beam.

As a result of the combined movement of the stage and the e-beam, the path of the beam relative to the substrate forms a scan pattern 102 as is shown in FIG. 2. Although this scan pattern 102 is shown as a sinusoidal pattern, it could instead be a triangular pattern or other shape, and data could be gathered from the resulting secondary electrons or other emissions as the beam is scanned in either direction, or in both directions. In the illustrated embodiment, the length of the scanned swath is the width of the test chip (e.g., 7 mm for a 7 mm by 7 mm test chip or 10 mm for a 10 mm by 10 mm test chip). However, the scanned swath can be less than the width of the test chip and still fall within the scope of the present invention. Preferably, the width of the scanned swath is as large as possible. For current commercially available systems the scan swath is between 50 μm and 500 μm in width. More preferably, the scanned swath is approximately 200 μm.

In one embodiment, the scanned swath includes at least part of each test structure on the test chip. So that a single scan may test all of the test structures. The scanned swath can contain a variety of different types of test structures. This permits the system to detect differing types of defects with a single pass through one scanned swath. However, it is also possible to create a structure having multiple swaths where each swath has only one type of test structure wholly or partially therein. The various types of test structures that can be included within the scanned swath are described more fully below.

Figure 3:
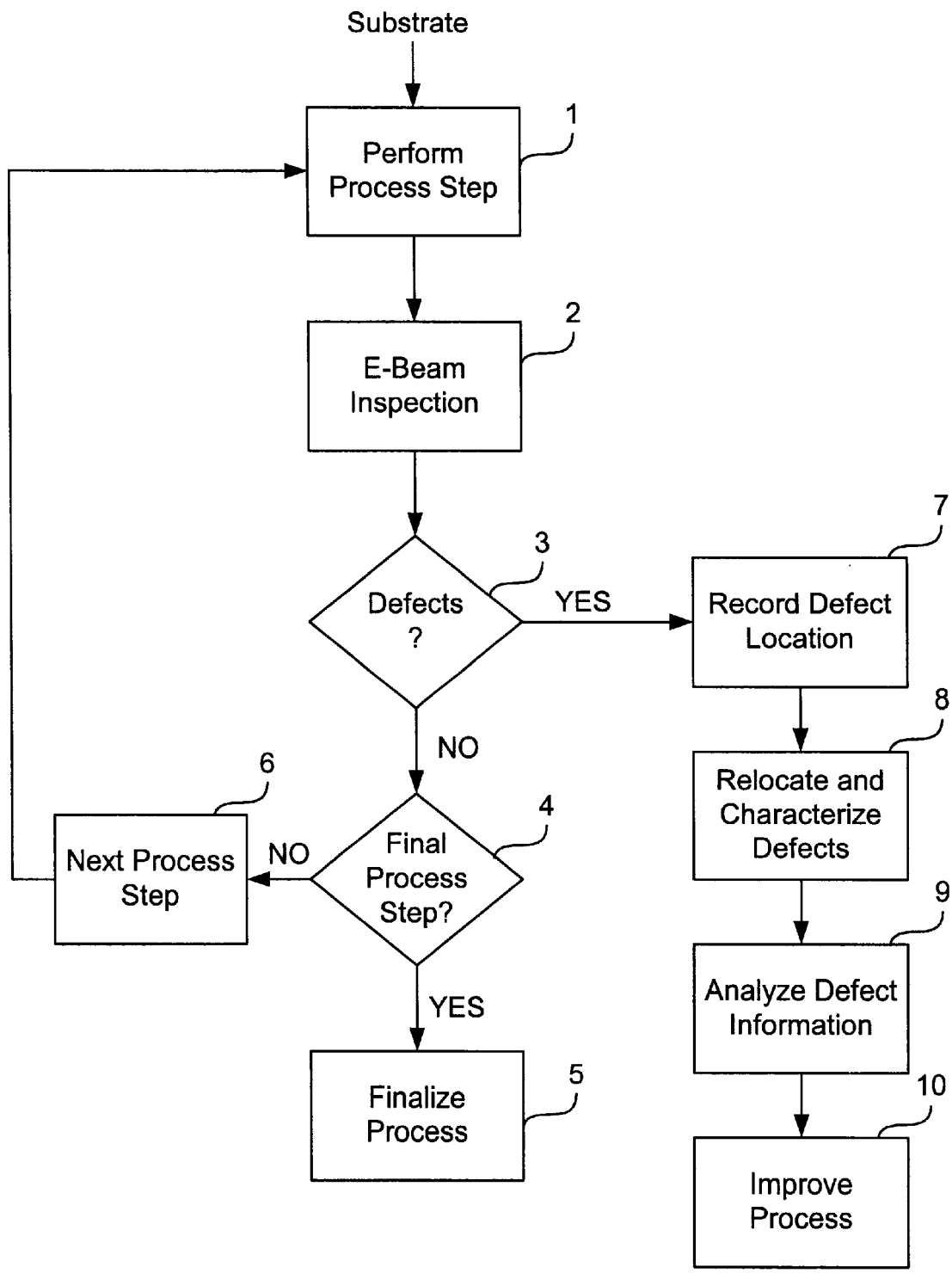
FIG. 3 is a flow chart illustrating an inspection procedure in accordance with one embodiment of the present invention.

FIG. 3 is a flowchart illustrating a process and test procedure in accordance with one embodiment of the present invention. Initially 3, in operation 1, a sequence of initial manufacturing process steps are performed to form a test structure such as conductive lines on a substrate. In operation 2 the structure is inspected by an electron beam inspection system. In operation 3, detected signals from the electron beam inspection are processed to determine whether a potential defect such as an open or a short in the conductive lines has been detected. If potential defects of sufficient severity to warrant termination of the manufacturing process have not been detected, then in operation 4 a subsequent manufacturing process step is performed. It is not unusual for thousands of potential defects to be found during inspection; however, they are often of insufficient number and severity to warrant termination of the manufacturing process, even for product wafers. If the process is still undergoing characterization, and the wafers are not product wafers, the processing of such wafers and the test structures thereon can continue even if numerous severe defects are located.

The number of test structures present in a lot of wafers and the relative area required for the test structures can be varied in a number of ways. One possibility is to have several reticles, each with varying amounts of area dedicated to test structures, which may be used in the manufacturing process. Reticles having a relatively large area devoted to test structures that can be used for certain wafers in a lot (or can be stepped over for a predetermined fraction of such wafers), while reticles having relatively fewer test structures can be used for other wafers in the lot (or stepped over a remaining fraction of such wafers). The relative extent of usage of each type of reticle determines the number of test structures in the lot, and this fraction can be varied from lot to lot depending on the testing requirements of the process at the time each lot is fabricated. Alternatively, a portion of a reticle containing test structures can be "bladed off" to a sufficient extent to create the desired predetermined number of test structures, and the remainder of each wafer would be covered with product structures.

If there is no subsequent manufacturing process step, the manufacturing process is finalized at 5. If there remains a subsequent manufacturing process step, the next manufacturing process step is initiated at 6.

However, if, in operation 3 a potential defect is detected, in operation 7 the location of the potential defect can be recorded. In operation 8, the potential defects can be re-located on the substrate and can be characterized using various characterization techniques such as scanning electron microscopy, optical microscopy, Energy Dispersive X-Ray Spectroscopy (EDS) and/or Focused Ion Beam (FIB) techniques, or any combination thereof. Finally, in operations 9 and 10 information from the characterization process is analyzed and the resulting data can be used to eliminate defect-causing process conditions. Of course, if the testing defect characterization process is nondestructive, the substrate can be returned to the process line for further processing.

C. Test Chip Design

Scanning a test chip using an apparatus with a moving stage provides a fast and efficient method for testing semiconductor devices for defects. It should be noted, as is described more fully below, that in order to be tested, a test structure need not reside wholly within the scanned swath. For many structures, voltage contrast testing can be accomplished by scanning only a small portion of a test structure. In such a case, if a defect is detected via the voltage contrast technique, the exact location of the defect can be determined in a subsequent operation, even if the defect is located outside the scanned swath.

As is discussed more fully below, a myriad of different types of test structures can be fabricated within the scanned swath. Some of these test structures are described more fully below. Such structures can include via chains and conductive lines, which preferably (but not necessarily) reside within the scanned swath only in part. The preferred structure of the via chains and conductive lines is described in more detail herein. Such structures can also include more compact test elements such as contact arrays and elements designed to detect defects caused by specific process steps, such as chemical mechanical polishing. These more compact elements preferably (but not necessarily) reside entirely within the scanned swath.

It should be further noted that the test structures described herein can also be tested by techniques other than that described herein as the preferred embodiment. For example, such test structures might be tested by a particle beam without a continuously moving stage, e.g. a step and repeat type stage in which the electron beam scanning is accomplished while the stage is stationary, and the stage is then moved and allowed to settle before a subsequent electron beam scanning step takes place. One embodiment of a stepper type test structure is described further below with reference to FIG. 33. Also, voltage contrast techniques that do not involve scanning with a particle beam can also be used in connection with many of the test structures described herein. For example, a photon beam (rather than an incident electron beam) could be used to induce voltage contrast. The photon beam could be used under conditions suitable for photo electron emission microscopy ("PEEM").

D. Exemplary Test Chip

Described in this section is an exemplary test chip that is specifically designed to take full advantage of the present invention. It should be recognized, however, that the specific design described herein is exemplary only and that many other designs or configuration are possible within the scope of the present invention.

Several embodiments of the present invention are described herein in the context of exemplary multilevel integrated circuit structures, including semiconductor structures and overlying metallization or other interconnects, using various levels of conductors that are separated from each other and the substrate by dielectric layers. As is well known in the art, in such multilevel structures, a first conductor (M1) and a second conductor (M2) can be connected by vias formed through an interlayer dielectric (ILD). Similarly, contacts can be formed between the conductors and the substrate. The defect detection system of the present invention is advantageously able to detect opens, intra-layer shorts (within M1 or M2) or interlayer (between M1 and M2) shorts caused by errors occurring systematically or randomly during the manufacturing process.

In addition, specific embodiments of the present invention are also able to detect defects caused by particular process steps, such as lithographic steps, dry etch steps, deposition steps, or a chemical mechanical polishing (CMP) process. As is well known in the art, the CMP process is often used to planarize structures that build up during multilevel deposition processes. These structures can be used as damascene interconnects, conductive plugs, or for other purposes. The CMP process is expected to become even more important as the semiconductor industry shifts to copper metallization, since copper cannot be easily dry-etched (the etch products being non-volatile), but is readily processed using CMP. However, the CMP process may polish away functioning circuit parts through dishing (leading to opens) or copper smearing (leading to shorts) when the circuit layout changes drastically in density, pitch and or in the horizontal aspect ratio (length:width). The defects created by CMP process are preferably detected during the inspection process.

Figure 4A:
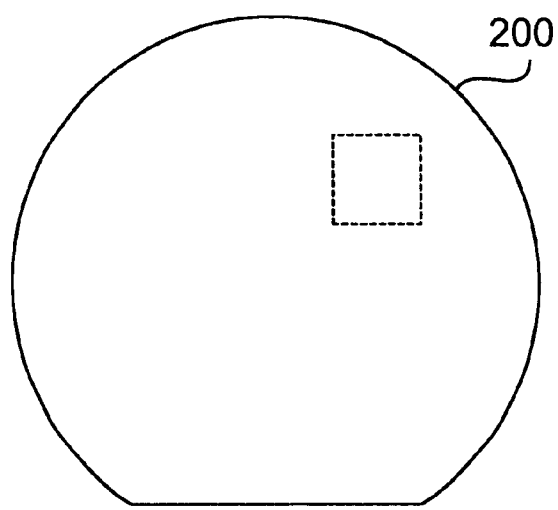
FIGS. 4a and 4b illustrate a semiconductor wafer comprising a die array that is prepared in accordance with the principles of the present invention.
Figure 4B:
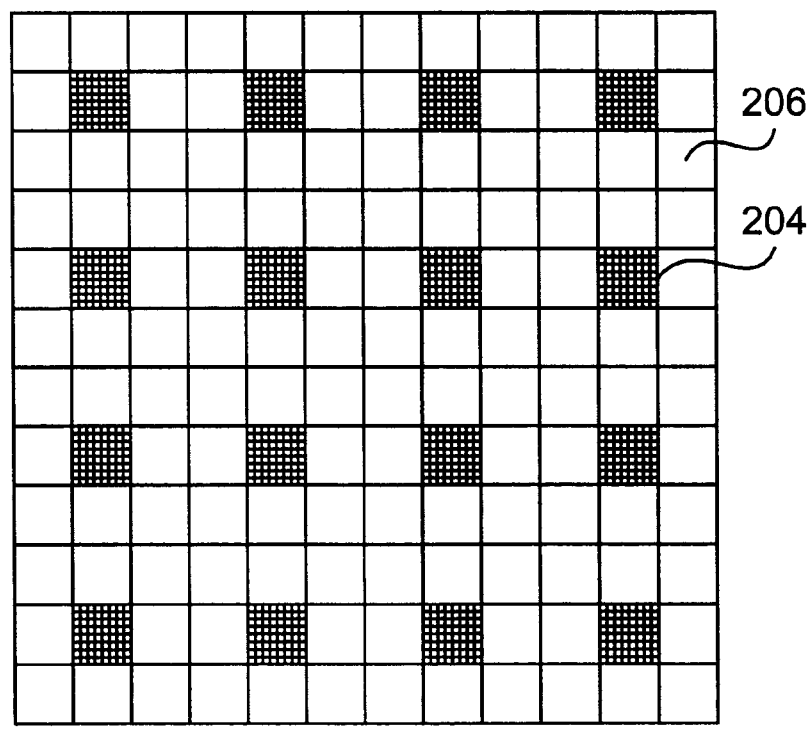

FIGS. 4*a* and 4*b* illustrate a semiconductor wafer 200 comprising a die array 202 that is prepared in accordance with the principles of one embodiment of the present invention. As illustrated in FIG. 4*b,* the array 202 may be comprised of a plurality of test dies 204 and a plurality of actual product dies 206 containing intended integrated circuitry. As will be described below, the test dies 204 allow defect location, defect identification, defect type and defect density through in-line inspections during the actual manufacturing process of integrated circuits.

The ability to detect defects in line (i.e., during the manufacturing process) is a significant advantage of the present invention. Unlike functional testing of semiconductor devices performed on completed wafers by wafer probing methods, the present invention can perform testing in line. This results in better and more timely information for the engineers controlling the manufacturing the process, and provides them with an opportunity to service machinery or alter process conditions to improve yield, before many devices are lost as scrap. By contrast, if the engineer were to wait until processing of the devices were completed, millions of dollars may be lost due to poor yield because of the delay. Moreover, the test methodologies of the present invention could be used as part of an Advanced Process Control ("APC") system, in which data from the testing process is fed to automated control systems that improve process yield with little or no human intervention, based on software algorithms that take into account the equipment and process technology used in the manufacturing process. As an example, test structures designed to detect CMP overpolish could provide data that automatically feeds back to the CMP process and causes the process to be modified such that polishing time is reduced, or pressure on the polishing pad is diminished.

The test dies 204 may be laid out in an orderly row-column fashion as shown in FIG. 4b. Such an orderly layout can be also used as a map to evaluate final test data and to locate certain types of defects occurring on various locations on the wafer during the manufacturing process. In one embodiment, the test dies 204 occupy a predetermined area on the wafer 200 so as to provide a statistically significant data set of test data, yet minimize the inspection cost and avoid adversely affecting the production yield. Such a test die has about the same dimensions as the product die in the range (e.g., 10 mm by 10 mm or 7 mm by 7 mm). Alternatively, when developing a new process, the wafer could be comprised entirely of test dies.

Figure 4C:
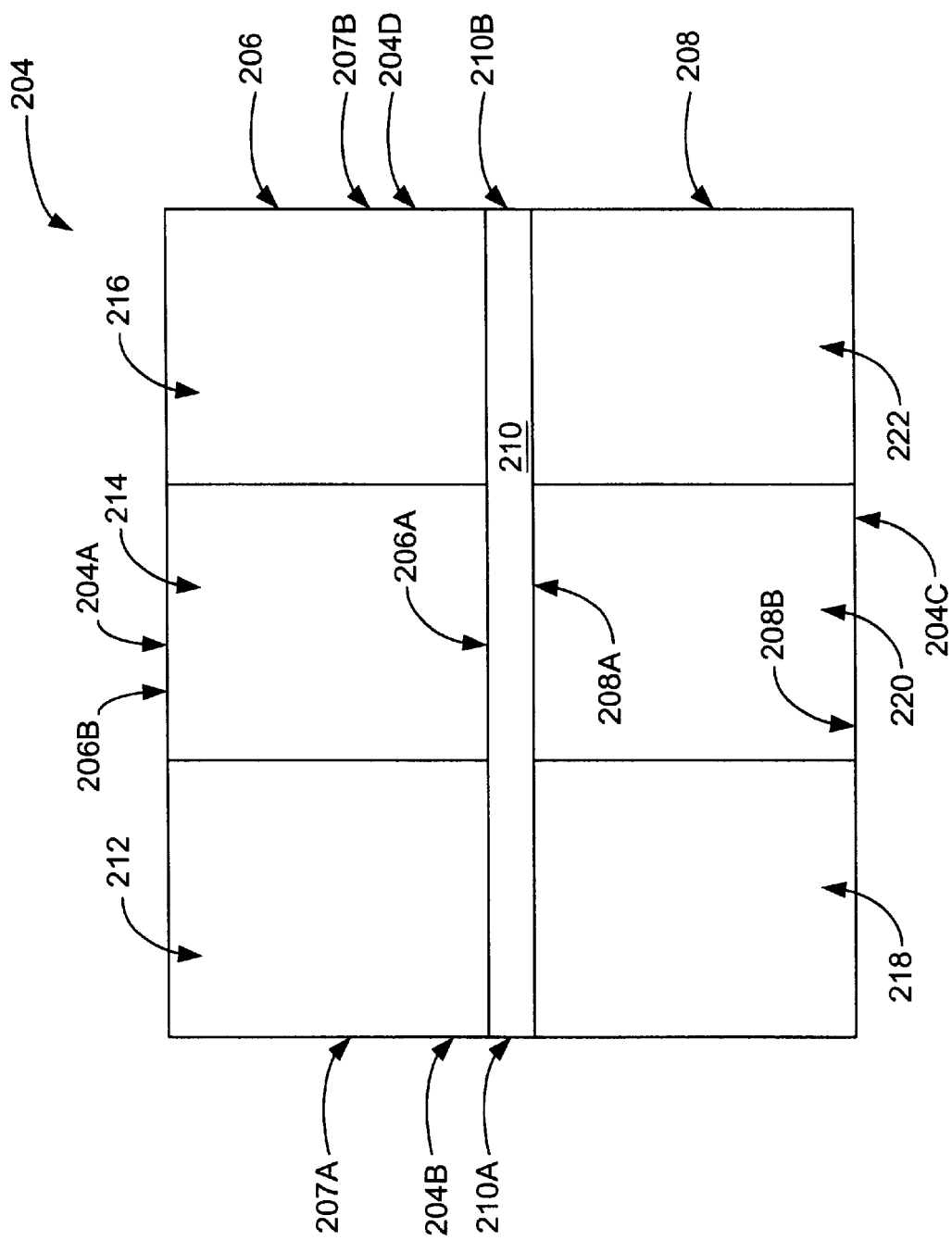
FIGS. 4c and 4d illustrate a test die fabricated in accordance with the principles of the present invention.

As illustrated in FIG. 4c, each individual test die 204 may be square or rectangular in shape defined by first, second, third and fourth edges 204A–204D, and configured to have a number of portions, namely, a first portion 206 and a second portion 208 separated by an intermediate portion 210. Sections 206–210 define the test sites where the test structures are formed. The portions 206, 208 and 210 of the test die 204 are preferably rectangular in shape.

As shown in FIG. 4c, the first portion 206 may be defined by a proximal edge 206A, a distal edge 206B, a first edge 207A and a second edge 207B. The second portion 208 may be defined by a proximal edge 208A, a distal edge 208B, a first edge 209A, and a second edge 209B. Finally, the intermediate portion 210 may be defined by the distal edges 206A and 208A, a first edge 210A and a second edge 210B.

As will be described more fully below, the test structures represent structures constructed in various steps of the semiconductor IC manufacturing process. Once the portions 206–210 are defined on the test die 204, the portions 206–210 may also be further divided into a plurality of sections, preferably rectangular, on which test structures may be placed by test type, as in the manner shown in FIG. 4c.

In a specific embodiment, the first portion may comprise a first section 212, a second section 214 and a third section 216. Similarly, the second portion 208 may be divided into three sections: namely a fourth section 218, a fifth section 220 and a sixth section 222. As will be described more fully below, each of the sections 212–222 as well as the portion 210 may comprise one or more groups of test structures that are laid out in a predetermined fashion according to their design (i.e., the type of functional structure to which the test structures correspond, or the type of defect the test structure is designed to find). The quantity of test structures of each type in a given portion, or on a test chip, or over an entire wafer, is selected to provide a statistically significant sample of such test structures, so that a statistically significant quantity of defective regions is likely to be found therein. This quantity will vary with the expected yield of the chips on the wafer. For example, in a low yield process (as might be expected to be found in a process that is under development and not yet in production), a relatively small number of test devices might be needed to obtain a reasonable sample size. By contrast, in a high yield process, a larger sample size (and therefore more test structures) may be needed. The quantity of test structures may also be varied depending on the goals of the chip manufacturer. For example, if the chip manufacturer is unwilling to devote much space on the wafer to test structures, the number of such structures could be kept relatively small. If process problems arise, the quantity of test structures present on each wafer could then be increased (to provide the manufacturer with more test data regarding the process) until the nature of the problem has been determined and corrected.

Data from such testing can also be used by both fabless integrated circuit makers, and the foundries that do their manufacturing. For example, the test structures may be inspected during the manufacturing process by the foundry. The same test structures may then be re-inspected by the fabless IC company before acceptance, to determine if the lot of wafers is likely to have an acceptable yield, to have an acceptable result during reliability testing, and to have acceptable quality. The data can also be used by the fabless IC company to improve the designs of its integrated circuits to make them easier to manufacture at higher yield and/or with superior quality. This data may be used as part of the purchasing process, so that the fabless companies could base their payment to the foundry, at least in part, on statistics calculated from the testing process, such as the predicted yield. For example, if the payment were to be made based on predicted good die, a lot having 500 die, and a predicted yield of 80 percent based on voltage contrast testing, could result in a payment for 400 predicted good die to the IC manufacturer. Testing by the fabless company could be facilitated, as described in more detail below, by using stacked vias containing stacked conductive plugs to create vertical conductive paths that tap down to the lowest test structures. Such test structures would otherwise be rendered inaccessible by subsequent processing, which would bury them under insulators and make them impossible to see in an electron beam system. However, by adding one or more conductive taps, these buried features can be re-tested even after all levels of the entire wafer have been fabricated. This makes the wafer testable by fabless semiconductor companies, and permits them to verify test data provided by the foundry. As described below, probable pads may also be added to the described voltage contrast test structures so that standard wafer probing techniques may also be implemented without the need for an expensive SEM device, for example.

Data from such testing could also be used to determine the need for other sorts of tests. For example, reliability is a relatively time consuming and expensive test. By processing data derived from the test structures of the present invention, one can better predict whether reliability testing is needed and how many chips from each lot should be subjected to such testing. For example, certain reliability failure mechanisms may be indicated as likely when test data from at least certain types of the test structures of the present invention indicates that defects are present which are close to, but not quite reaching, a quantity or level of severity that would affect device functionality. Under such circumstances, one could predict that reliability testing conditions would cause such devices to fail at an unacceptable level. Reliability testing could be conducted to verify this, and the process (if desired) could be altered to lessen the severity of such predicted reliability failures, even before the reliability testing is actually performed.

As previously mentioned above, the first section 212 may comprise test structures involving M1 interconnect level, for example. A test structure formed on the first section 212 may represent the M1 processing stage of an integrated circuit and allow testing and evaluation at this stage of the production. At this stage, inspections may be performed to detect opens and intra-layer shorts in the M1 interconnect wiring, in-line, during the manufacturing process. Similarly, test structures relating to M2 and M3 interconnect lines are formed on the third and fifth sections 216 and 220 respectively. M2 and M3 test structures also allow detection of opens and shorts, and interlayer shorts such as those between the M1 and M2 interconnect test structures. Via chain test structures may be formed on the second, fourth and sixth sections 214, 218 and 222. The second section 214, for example, may represent via chains constructed between M1 and M2 interconnect lines. In this respect, the fourth and sixth sections 218 and 222 may have via chain test structures representing vias between M2 and M3 interconnect lines and M3 and M4 interconnect lines, respectively.

As will be described below, via chain test structures allow two types of tests, namely opens only tests to detect opens in via chains, and opens and shorts tests to detect both opens in the chain and shorts between the neighboring conductor or metal shapes.

In this embodiment, various other groups of test structures are formed along the intermediate portion 210 of the die 204. As is described more fully below, such test structure groups may comprise CMP test structures, overlay or misalignment structures and individual contacts, as well as dummy CMP fillings. In this embodiment, dummy CMP fillings can also be formed on available unoccupied areas on the product dies, such as those available along the corners of the die or unoccupied areas found between the neighboring circuit layout sections.

Figure 4D:
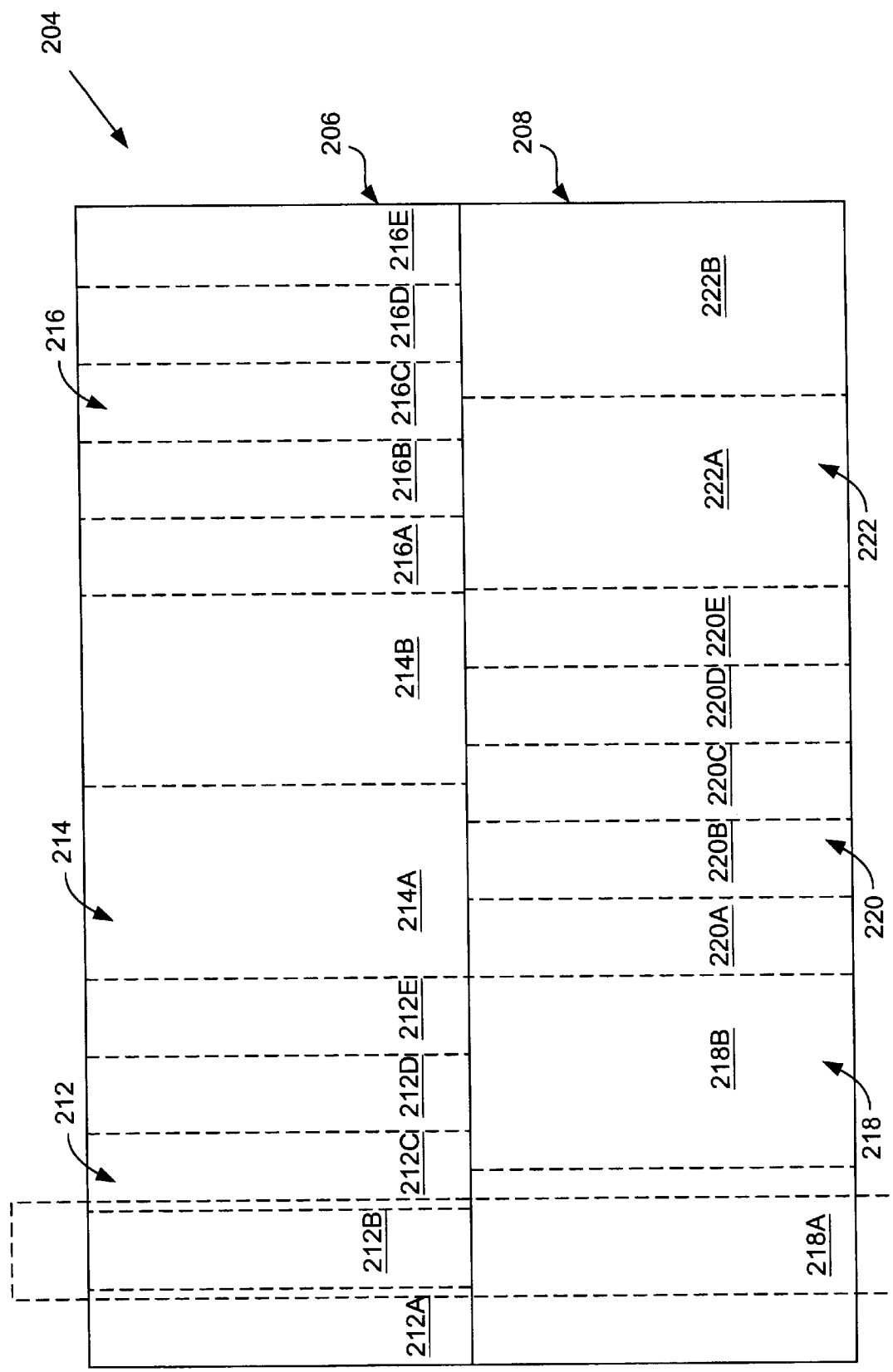

As illustrated in FIG. 4d, sections 212–222 may be further divided into a plurality of subsections or modules to have test structures with differing critical dimensions over such modules. In this context, critical dimension often refers to a predetermined test size of a feature or the distance between features. By way of using test structures having different critical dimensions, superior IC features can be produced. In other words, if a particular acceptable critical dimension produces the best result with respect to a specific design feature, that critical dimension can be adopted and design rules for that process or product family can be altered accordingly. More importantly, test structures implemented with various geometries and critical dimensions help to determine which device geometries or dimensions are more prone to certain defects, and can predict the resulting defects occurring between the two devices due to the distance between them.

In this respect, for example, the M1 interconnect lines in the section 212 may be formed on a first, second, third, fourth and fifth modules 212A–212E, each module having one type of test structure group formed with a critical dimension different than the critical dimensions used in other modules. The modules 212A–212E help to determine which critical dimension for M1 interconnects are more vulnerable to opens, shorts and interlayer short type of defects. Similarly, first, second, third, fourth and fifth modules 216A–216E in section 216 and first, second, third, fourth and fifth modules 220A–220E in section 220 provide interconnect lines with differing critical dimensions for M2 and M3 process steps respectively, for opens, shorts and interlayer short types of defects.

Referring to FIG. 4d, the section 214 may be comprised of two modules, namely first and second modules 214A and 214B, each comprising via chain test structures formed between the M1 and M2 interconnect levels. In this embodiment, first module 214A may comprise via chains that are formed to detect opens type of defects while the second module 214B comprises via chains to detect both opens and shorts type of defects. As will be described more fully below, in the second module 214B, individual via chain lines may be interposed neighboring metal lines so as to detect and monitor both shorts occurring between the via chains and the neighboring metal lines and opens in individual chains. Similarly, first and second modules 218A and 218B in section 218 and first and second modules 222A and 222B in the section 222 provide via chain test structures to monitor and detect opens as well as opens and shorts types of defects as described for modules 214a and 214B.

It should be noted again that the above-described test chip is exemplary only. For example, test structures can be located in different places in such a chip, or certain test structures described herein may not be included at all. Many different configurations are possible within the scope of the present invention.

E. Testing of the Exemplary Test Chip

As previously described, an electron beam inspection system, such as an SEM, may be used. When the electron probe strikes over the surface of the die at a given point, this action gives rise to signals that can be collected by the detector to give information about that point. The electron beam system is programmed to move the wafer to bring the first test chip into position at a low magnification (60–500×), and locate, for example the first line of features such as opens/shorts-test-patterns in a linear array, and draw the electron beam scan line through them in a raster mode.

In one embodiment, the primary signal source comprises electrons. Secondary electrons are generated as a result of the incident (primary) electron beam striking the surface of the wafer. The secondary electrons are emitted from the wafer and collected by the detector to create the image. In the image, the high-intensity secondary electron emitting features come out, for example, visually brighter than the low-intensity secondary electron emitting features. If this variation in secondary electron emission intensity is plotted with respect to the distance, along the swath-length that the electron beam scans, an intensity distribution of the scanned test structure is obtained.

In a die-to-database or die-to-perfect-image inspection mode, the system operates to match the intensity distribution of a defect-free test structure as represented in the data base to the intensity plot of the corresponding structure on the test chip provided by the electron beam unit. In one embodiment, the die under test is compared to an image that represents what the die under test looks like without any defects. For example, an array of interconnect lines may alternate between being tied to ground and left floating. In this case, a perfect image is generated that has alternating dark and bright interconnect lines. This comparison operation allows the detection of all the defects in the test structure in terms of missing and/or extra peaks. Alternatively, the intensity peaks of the test structure may be compared to a predetermined set of expected values, e.g., arranged in a truth table. For example, a set of interconnect lines on the test structure under test may be expected to have alternating high and low intensity values. In one embodiment, each line is compared with a predetermined threshold to determine whether the conductive line is grounded or floating. These high and low values are then compared to the expected high and low values. The test structure itself may also be configured to facilitate die-to-perfect die inspection and die-to-truth table inspection. In one embodiment, the length of the proximal-ends (or stubs) of the test pattern have varying lengths, which may also be matched to the corresponding perfect die portion or truth table values. For example, two stubs in a row may have a same length (while the other stubs have a different same length) to indicate a starting or reference point to begin the comparison procedure. In a second example programmed defects are incorporated at fixed intervals along the scan path to form a fixed grid to aid in defect location during subsequent analysis.

The generated perfect image and/or set of predetermined intensity values or truth table values, along with the corresponding test structures, may also be provided to the customer so that they may easily inspect the corresponding test structures. Of course, standard die-to-die and array inspection techniques may also be utilized. However, the die-to-database, die-to-perfect image, and die-to-truth-table techniques represent a more efficient inspection procedure since a perfect die or die portion does not have to be found for comparison to the die under test.

The scanning electron microscope, in the voltage contrast mode, enables one to distinguish the charged floating conductor shapes from the charge-drained grounded shapes in terms of visual or intensity contrasts. These shapes can be monitored visually on a CRT-screen, or, preferably, stored and analyzed electronically. This principle has been used previously to manually locate, isolate, and in-situ characterize defects causing unintended discontinuities to ground or unintended shorts to the neighboring grounded-shapes in a product chip. However, such a manual product-inspection process is extremely tedious and slow because of the complexity of the product design and the high magnification source on the poorly contrasting CRT screen of the SEM.

Figure 5:
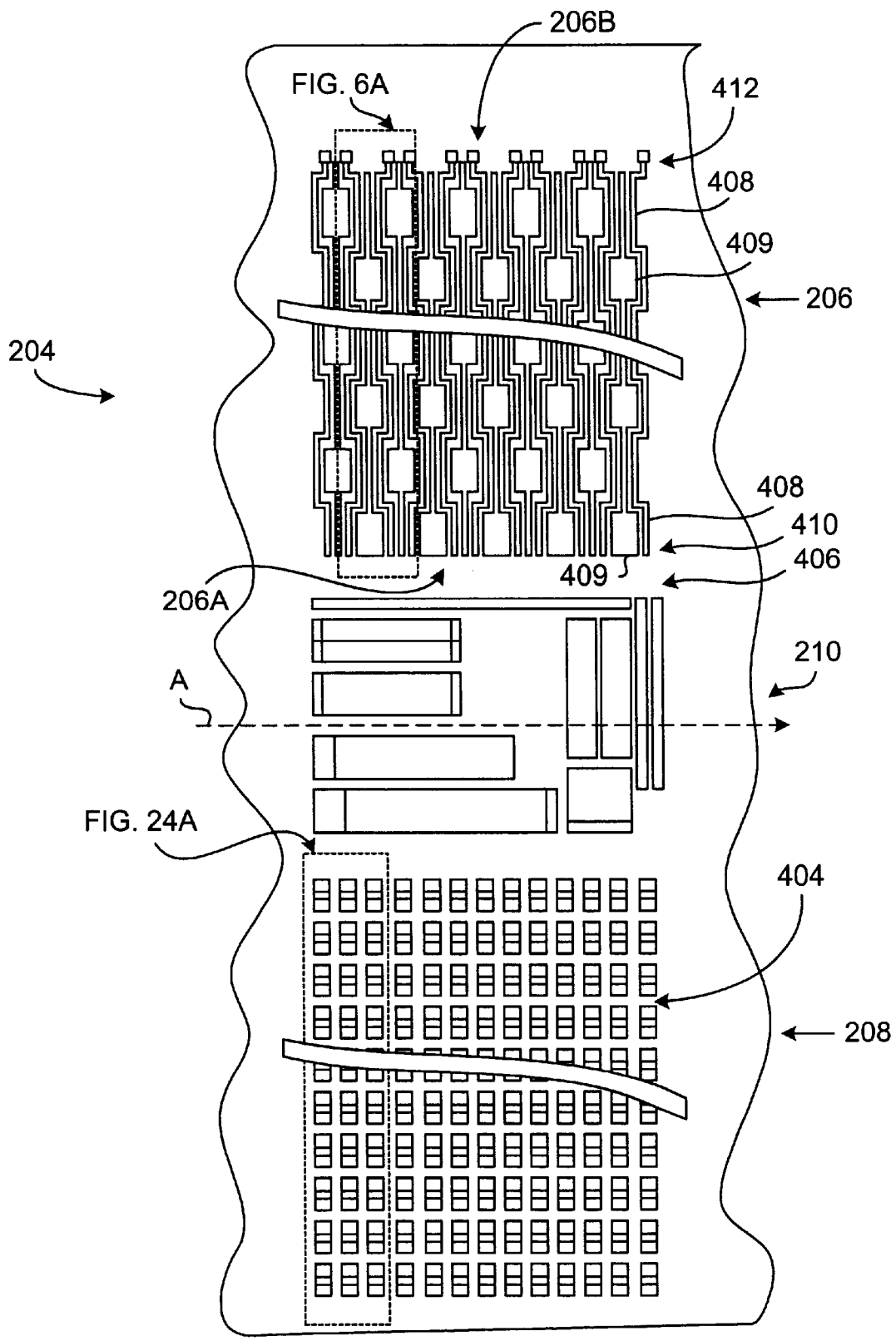
FIG. 5 illustrates in plan view an exemplary portion of the test die of FIGS. 4c and 4d.

In FIG. 5, in plan view, an exemplary portion 400 of the test die 204 is shown in detail. The portion 400 gives a detailed view of parts of the first portion 206, the second portion 208 and the intermediate portion 210 of the test die 204 (e.g., of FIG. 4c). One technique of the present invention will be exemplified using first test structures 402 on the first portion, second test structure 404 on the second portion of the test die 204 and third test structures 406 on the intermediate portion of the test die 204. It is understood that, during the electron beam inspection of the test die 204, the electron beam is scanned over the intermediate portion in a raster mode and in the direction of arrow A. The electron beam interacts with the test structures on the intermediate portion as well as with the proximal ends (referred to as "stubs") of the test structures on the first and second portions but located adjacent to proximal edges of the first and second portions. In the following section of this application, the first, second and third test structures are described in further detail.

Figure 32:
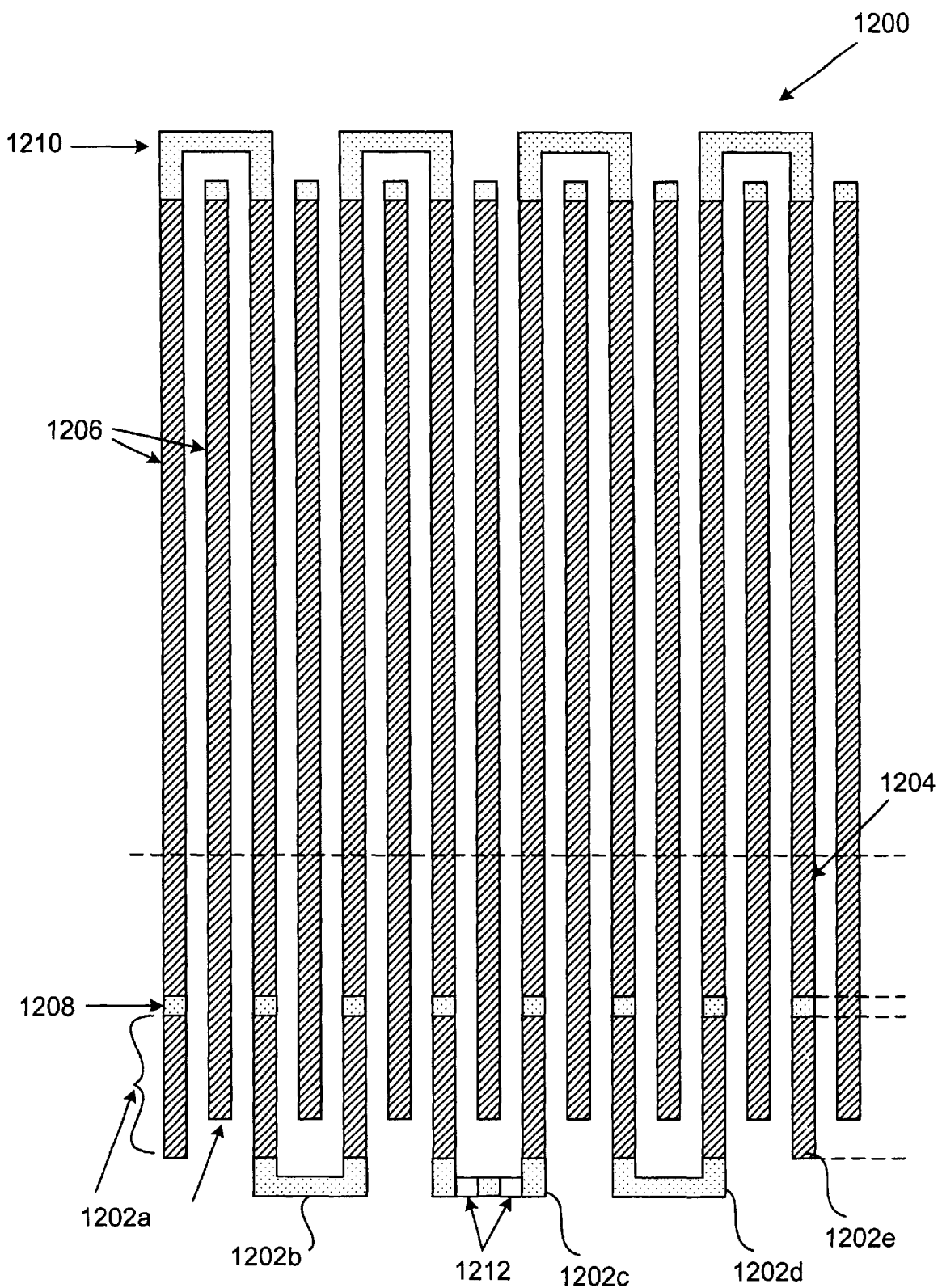
FIG. 32 illustrates a serpentine type test structure that may be utilized to measure line resistance.

As is described more fully below and seen in FIGS. 5, 6a, 6b, 6c, the first test structures 402 comprises rows of first conductors 408 and second conductors 409, extending parallel to the edges 204B and 204D, and between the proximal and distal edges 206A and 206B of the test die 204 (See FIG. 4c). The second conductors 409 are located between the rows of first connectors 408 as in the manner shown in FIG. 5. In a specific embodiment, proximal stub is ends 410 of the first connectors 408, which are referred to herein as interconnect lines, are located at the proximal edge 206A of the portion 206 of the test die 204 (See FIG. 4c), and distal ends 412 of the interconnect lines 408 are located at the distal edge 206B of the die portion 206. It is understood that the first test structure 402 exemplified in FIG. 5 may represent a plan view of any of the metal interconnect layers such as M1, M2, M3 or M4. As will be described below, the distal ends 412 of the interconnect lines 408 are grounded to the substrate of the die 204 while the proximal stub ends 410 are free and are not grounded to the substrate. As is described below, the second connectors 409, which are referred to as island members, are not grounded and help to distinguish defects occurring in grounded interconnect lines 408 in the voltage contrast mode. These proximal ends of 408 and 409 may be extended to different lengths for exposure in the primary-scan area, as described earlier. Also, it will be understood that 408 and 409 shapes can be straight-lines without corners or islands as shown in FIG. 32.

In a preferred embodiment, each stub 410 has a width that is the same or less than the rest of the interconnect line 408. That is, a widened flag area is not utilized. Since the stub width is the same or less than the rest of the interconnect line, a plurality of interconnect lines may be densely packed in a simplified array. In other words, the proximal end of the test structure itself can be scanned "as is" in the Primary-Scan Area. In this embodiment, the spot size of the inspection SEM is generally configured to the stub's dimensions.

Referring to the exemplary test chip illustrated in FIGS. 4a–d, the test chip is preferably scanned in a single pass. The scanned swath preferably includes all of intermediate portion 210. Further, portion 210 is preferably located substantially in the center of the test chip. Additionally, in one embodiment, the intermediate portions 210 of a plurality of test chips are aligned such that a single scan may be performed on a plurality of intermediate portions 210 on a plurality of test chips.

Preferably, the scanned swath includes an area larger than portion 210, however. In a specific embodiment, all of the test structures on the test chip are scanned in a single pass. Therefore, where the width of the scanned swath is 200 μm, for example, the width of portion 210 might be 190 μm. In such an instance, the scanned swath might include up to 5 μm above and up to 5 μm below portion 210.

In such an instance, it would be possible, and preferable, to inspect all of the test structures of the test chip with only a single scan of the scanned swath (e.g., the Primary-Scan Area). In this regard, a scan of the scanned swath would scan all the test structures that reside in portion 210. Such a scan would also scan portions of the test structures of portions 212, 214, 216, 218, 220, and 222. In the event the scan of the scanned swath reveals a defect in one of the test structures of portions 212, 214, 216, 218, 220, or 222, the system, according to a specific embodiment, would then take steps to locate and further characterize the defect (which is typically located outside the scanned swath (e.g., in the potential Secondary-Scan Area).

It should be noted that the scanned swath need not be located in the center of the test chip, but can be located elsewhere on the chip. For example, the scanned swath could be located at the bottom or top of the chip. In the case, for example, where the scanned swath is located at the bottom of the chip, the scanned swath might comprise test structures that reside entirely within the scanned swath, as well as portions of test structures that extend upward from the scanned swath.

Further, a test chip might be designed to have more than one scanned swath. In an alternative embodiment, there are multiple intermediate portions 210 within a single test die so that the aspect ratio of each test structure is optimized. For example, the interconnect lines 408 may be shortened so as to reduce their resistance, capacitance and/or the time required to locate a defect on such lines. In another embodiment, intermediate portions (e.g., 210) and corresponding first and second portions (e.g., 206 and 208) are configured in an array so that scans of the intermediate portions may be conducted in an array mode. In addition, a scanned swath might not be coextensive with the width of the test chip, but might be located entirely on the inside of the test chip. In fact, it is possible to have several scanned swaths on a single test chip, all located entirely inside the chip. However, it should be recognized that it is preferred that any scanned swath comprise specific test structures that reside entirely within the scanned swath and other-specific test structures that reside only in part within the scanned swath.

F. Conductive Line Test Structures

One type of test structure that can be included on a test chip may have its end-regions projecting into the Primary-Scan-swath. In the preferred embodiment, such test structures will reside within a scanned swath only in part. It is preferable only to scan initially a small portion of a conductive line. If a defect is detected, then further testing and analysis can be undertaken in order to locate the defect more precisely and to characterize it.

Figure 6A:
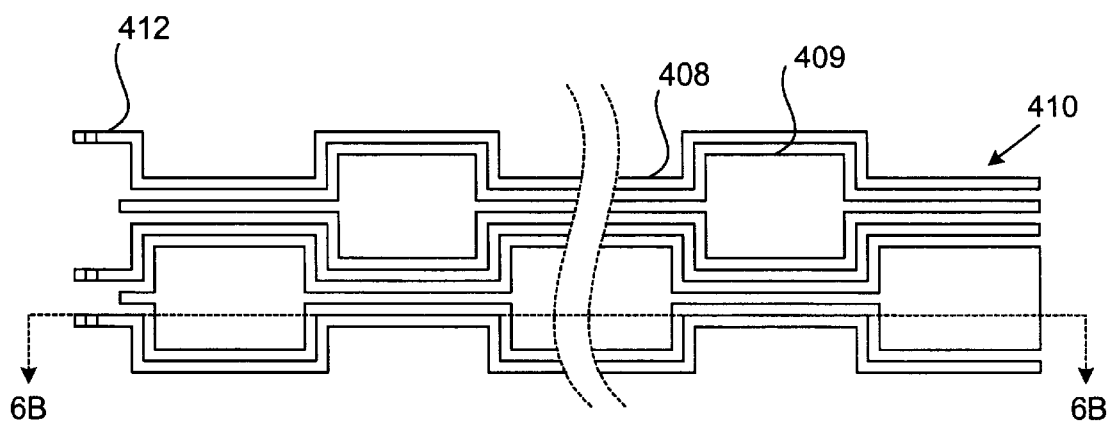
FIGS. 6a through 6c illustrate a part of a test structure in plan view, cross section and a side view.
Figure 6B:
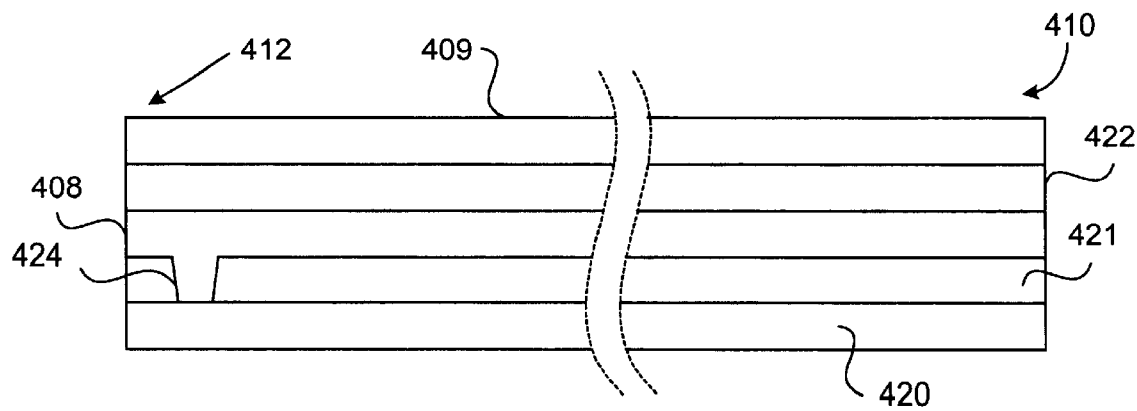
Figure 6C:
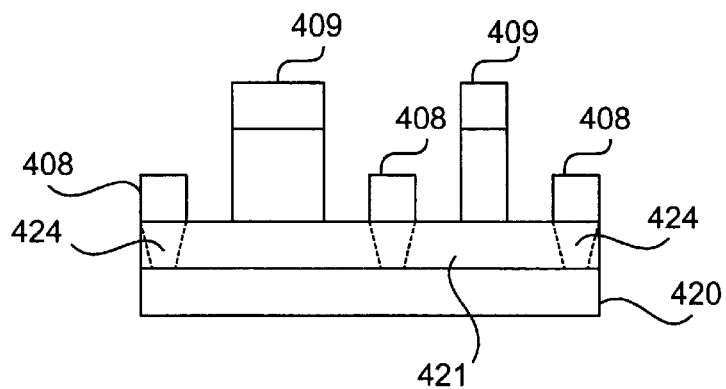

FIGS. 6a–6c illustrate a part of the test structure 402 an M1 wiring test structure in plan view, cross section and a side view in detail. Referring to FIGS. 6a–6c, the M1 interconnect 408 and the floating-member 409 are formed over a substrate 420 using conventional semiconductor IC process techniques such as Chemical Vapor Deposition (CVD), patterning and etching techniques. An isolation layer 421, such as an oxide layer, that is interposed between the substrate 420 and the M1 interconnect 408 isolates the M1 interconnect 408 from the substrate 420. The island member 409 is separated from the M1 interconnect by a dielectric layer 422 and configured such that the island member 409 has an elevated posture as in the manner shown in FIG. 6c in side view. The interconnect line 408 is connected to the substrate 420 through a contact that may be etched through the oxide layer 421. Through the contact 424, the interconnect line 408 is electrically grounded to the substrate 420.

An electron beam may scan across the distal end 410 of the exposed metals of the interconnects 408 and floating-members 409 to detect defects, for example, opens, shorts and intra-layer shorts in the M1 wiring. This preferred embodiment provides an immediate calibration of the scan-intensities of the grounded or floating shapes during the Primary Scan. Detection of intra-layer shorts and opens tests are performed by scanning the electron beam across the distal end 410.

During the electron beam inspection, since the island members 409 are not grounded, electron flow from the incoming incident electron beam charges island members 409. Contrary to the grounded interconnect lines 408, electrons cannot find a path to the ground and secondary electron emission does not occur, as a result the island members 409 charged by the beam remain nominally dark. Owing to their ground connection and assuming that they are defect free, however, the interconnect lines 408 remain charge-drained and generate significant amount of secondary electron radiation to be detected by the detector of the electron beam system. For the grounded interconnect lines 408, the electrons from the beam will find a path to ground and secondary electrons will be emitted from that particular interconnect line 408 if such interconnect line 408 is not broken. As a result, that interconnect line 408 will appear brighter or appear to glow, thus indicating that the corresponding interconnect line does not have an open (i.e., it is not defective). The intensity peak arising from this secondary electron emission will also be registered by the system to match with the corresponding data on this particular test structure. However, if the line under test is broken (i.e., it is open), there will be less secondary electron emission and, thus, the interconnect 408 will remain dark. As previously mentioned, the missing peak will then be registered by the system, hence indicating a potentially defective interconnect for further analysis. In another possible case, if an interconnect line is shorted to another interconnect line for the same M1 wiring, both interconnect lines 408 and 409 will glow, indicating the electrical short between them.

With the inventive test die, the quality of the M1 wiring or other levels of wiring can be monitored throughout the manufacturing process. During the manufacture of multi-level metal structures, elevated temperatures may cause shorts and opens in the previously produced wiring interconnect patterns having latent defects. This problem can be monitored using a test structure shown in FIGS. 7a and 7b. In the following section, for the purpose of clarity, island members 409 will not be shown in the figures that provide sectional views.

Figure 7A:
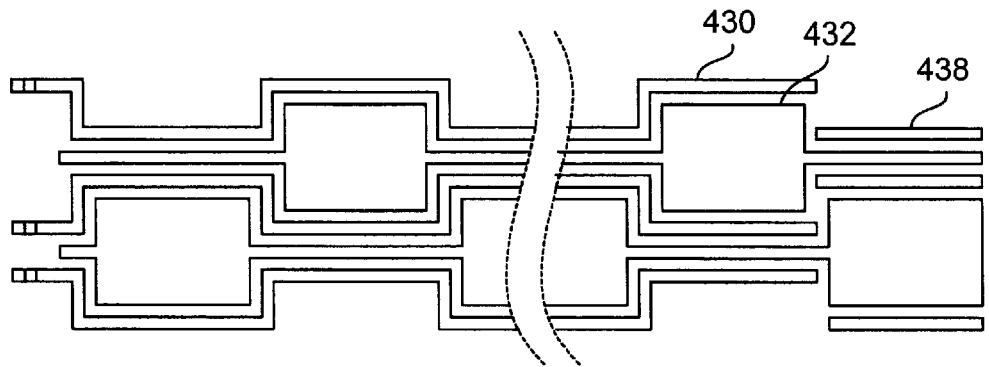
FIGS. 7a and 7b show a part of a test structure having M2 interconnect wiring and island elements at the top.
Figure 7B:
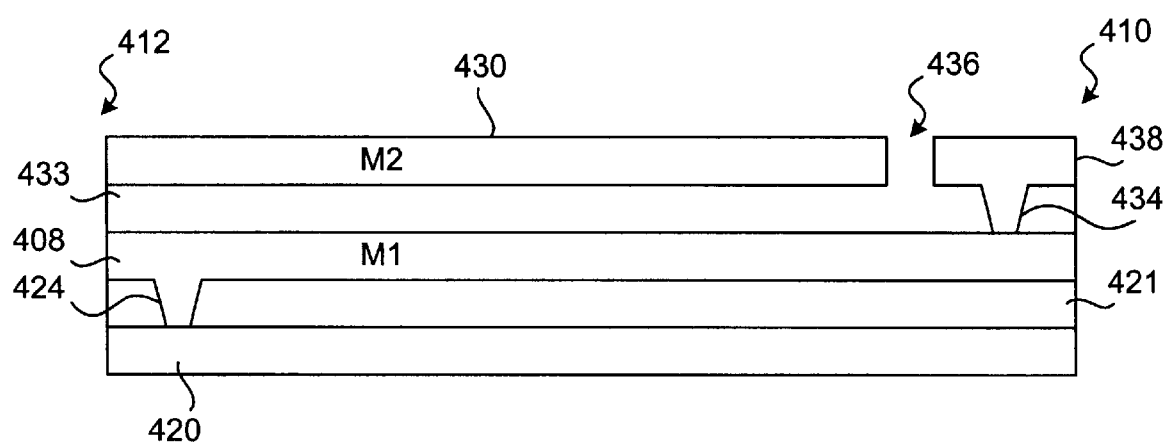

FIGS. 7a and 7b show a part of the test structure 402 having M2 interconnect wiring 430 and island elements 432 at the top. That is, the M1 interconnect wiring is buried. As shown in cross section in FIG. 7b, the M1 interconnect lines 408 are connected to the substrate 420 through the contact 424 as in the manner shown also in FIG. 6b. An interlayer dielectric layer 433 is interposed between an M2 interconnect layer 430 and the M1 interconnect layer 408. A via 434 connects the proximal end 410 of the interconnect 430 to the M1 interconnect through the dielectric 433.

However, in this embodiment, in order to monitor the quality of the M1 interconnect layer, after the M2 process step, the M2 interconnect 430 is made discontinuous by forming an opening 436 adjacent to the via 434 between the interconnects 408 and 430 and separating a distal portion 438 from the rest of the M2 interconnect. The opening 432 may be filled with an isolating material such as a damascene oxide using techniques well known in the art. The distal portion 438, is referred to as the first scan element hereinafter (also later referred to as a "tap").

At this step of the process, an electron beam probe may be scanned across the first scan element 438 of the M2 interconnects and island members 430 to detect defects, for example, opens, shorts and intra-layer shorts in the M1 wiring. Detection of intra-layer shorts and opens tests are performed by scanning the electron beam across the scan element 438. In one situation, if M1 interconnect line 408 is not broken, the electrons from the beam will find a path to ground from the scan element to substrate through the M1 interconnect 408. As a result, secondary electrons will be emitted from the scan element 438, thus indicating that the M1 interconnect line 408 is still good after the M2 wiring-process step. In another situation, if the M2 wiring step causes an open in the M1 interconnect 408, the first scan element 438 will not emit secondary electrons and thus the first scan element 438 will remain dark. If the rest of the M2 interconnect 430 is shorted to the underlying M1 interconnect line, the electrons from the electron beam will find a path to ground and the shorted M2 interconnect and the corresponding scan element will glow, indicating the interlayer short between the M1 and M2 wiring at that interconnect.

In configurations constructed in accordance with the principle exemplified by FIG. 7b, it is also possible to make use of stacked vias (vias that extend upward through multiple layers). In this manner, for example, one or more stacked vias may extend from M1 to M3 to allow testing of the integrity of M1 after the fabrication of M3. Additionally, redundant vias (i.e., multiple vias) may be utilized in place of any of the single vias (e.g.,234 and 424). Redundant vias tend to result in less defects than single vias, but redundant vias have slightly more complex design requirements.

Figure 8:
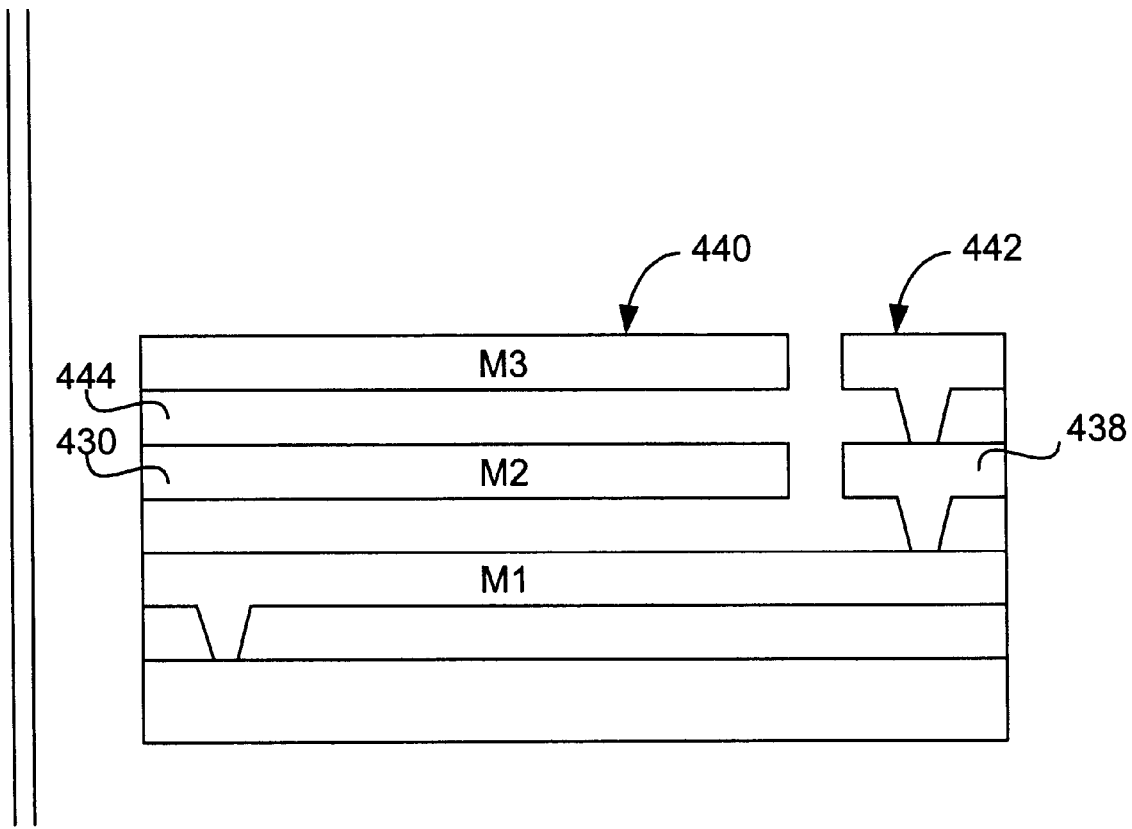
FIGS. 8 through 13 illustrate test structures that are designed to test the integrity of covered metal layers.
Figure 9:
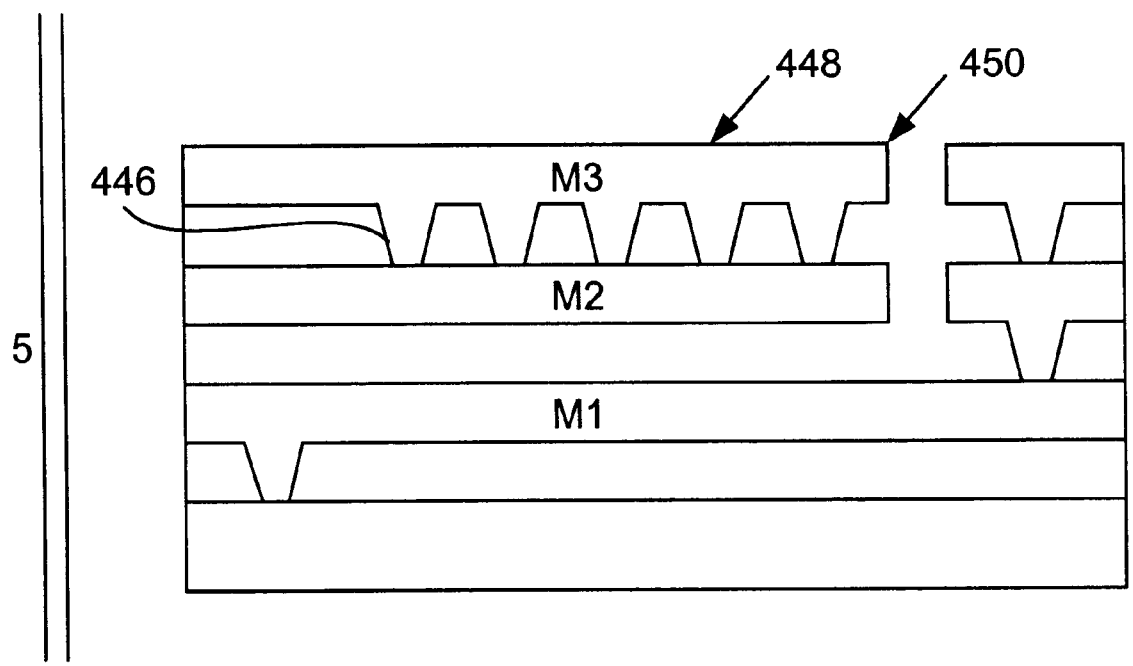
Figure 10:
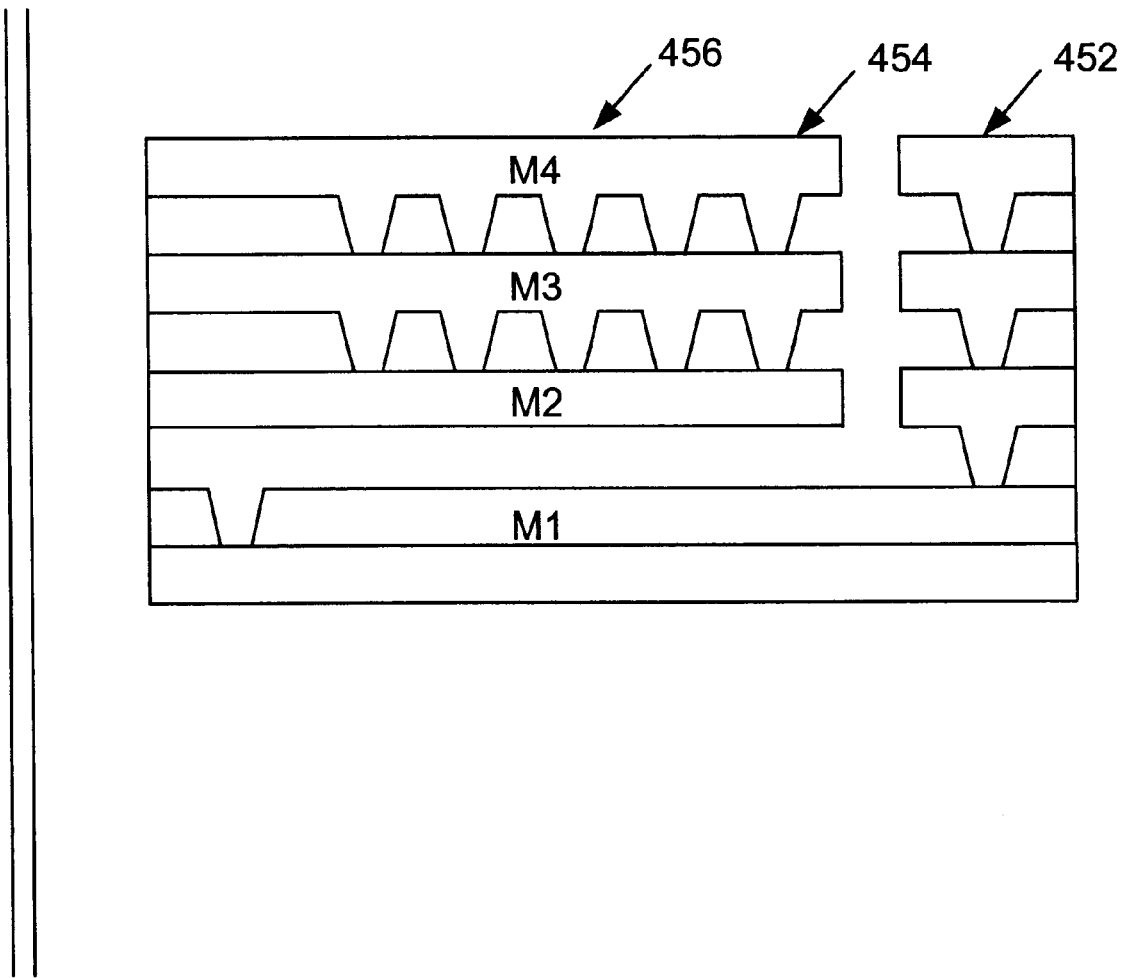

As illustrated in FIGS. 8–10, the integrity of the M1 interconnect 408 can be further detected after the fabrication of the third, fourth and more metal interconnect layers. For example, in FIG. 8, an M3 interconnect 440 having a first scan element 442 connected to the first scan element 438 of the M2 interconnect 430 can be formed on an interlayer dielectric 444. In other words, a stacked plug (first scan elements 442 and 438) is formed to monitor opens within a buried metal layer M1. As shown in FIG. 9, by forming a number of vias 446 between the M3 and M2 interconnects, a second scan element 448 can be formed to monitor a possible short between the M1 and M2 interconnects. During the electron beam inspection of the scanned swath, a proximal end of the M3 interconnect may be scanned. Similarly, as shown in FIG. 10 after forming first and second scan elements 452 and 454 of a M4 interconnect 456, opens in the M1 layer (through stacked plugs 452), as well as shorts between the M1 and M2 interconnects, can still be inspected through scan element 454).

Figure 11:
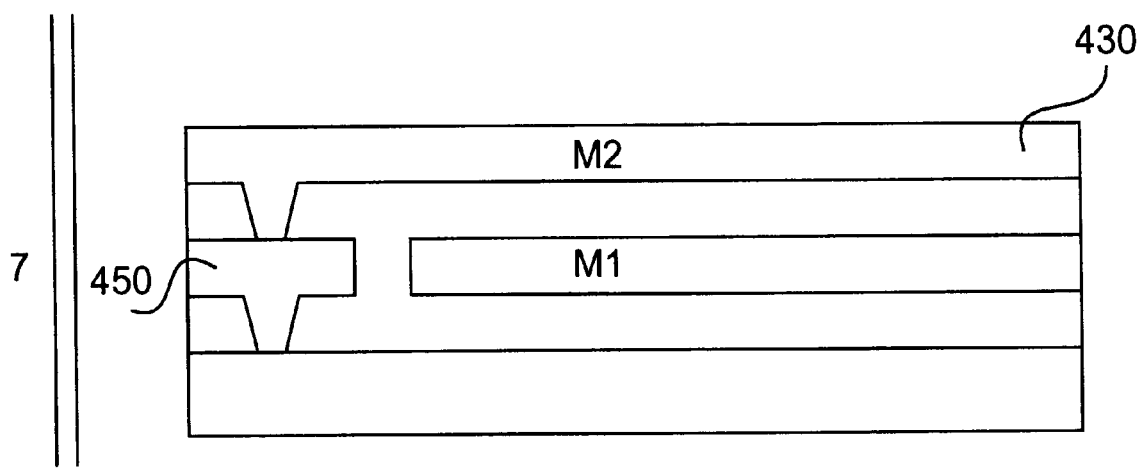
Figure 12:
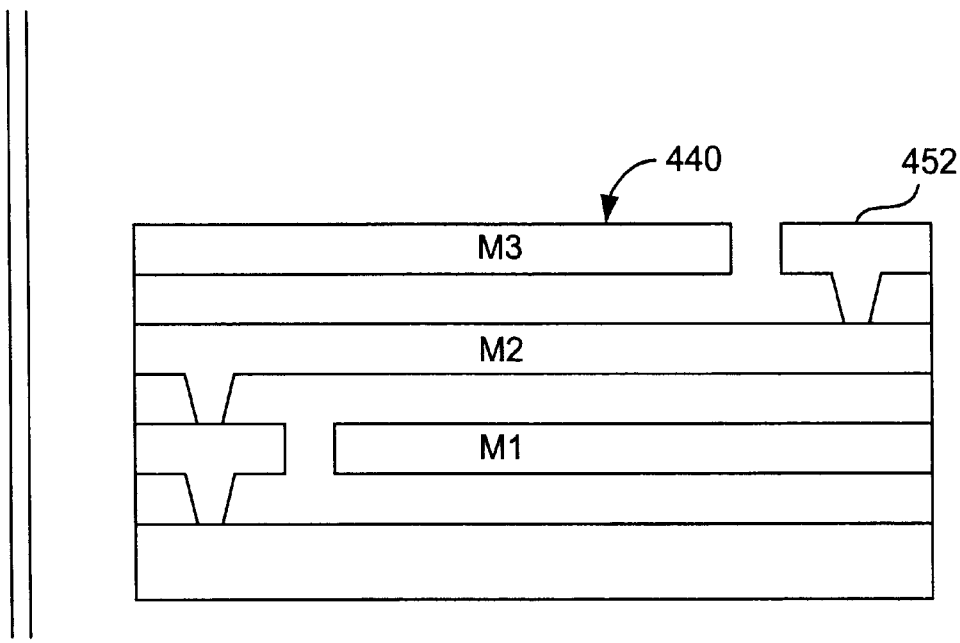
Figure 13:
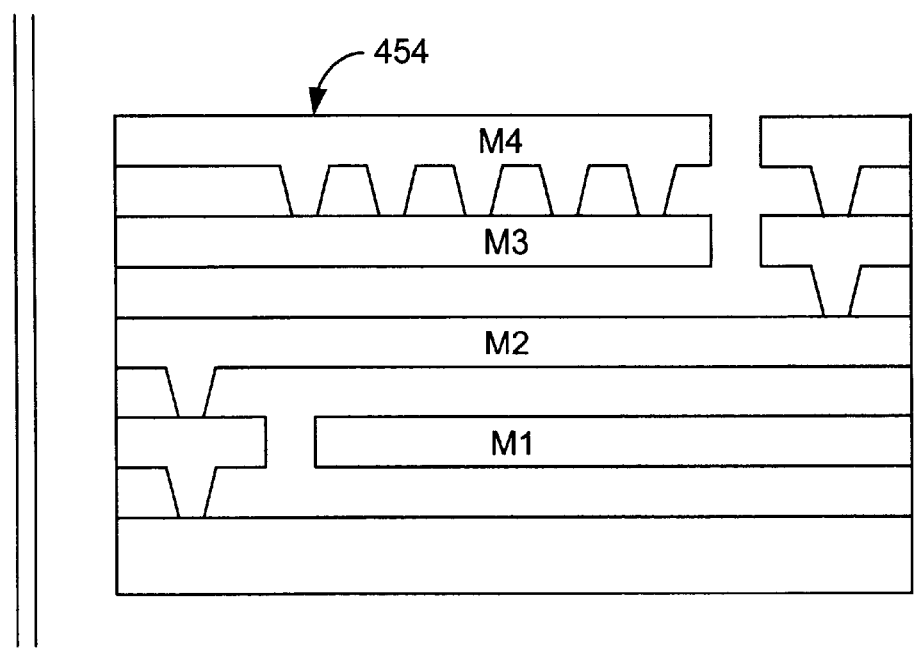

As illustrated in FIGS. 11 to 13, the same aspects can be applied to the testing of M2 interconnects. As shown in FIG. 10, the M2 interconnect is grounded through a disconnected portion 450 of the M1 interconnect. As shown in FIG. 12, the integrity of the M2 layer can be still tested using a first scan element 452 of M3 interconnect 440. As shown in FIG. 13, possible shorts between the M3 and M2 interconnects, after forming the M4 interconnect, can be detected using a second scan element 454 of the M4 interconnect.

The above described stacked test structures may be utilized to inspect buried structures. A single test structure may include mechanisms for inspecting two or more buried structures each at different levels. For example, a first tap may be connected to an M1 conductive line that is grounded at its distal end, while a second tap is coupled to an M2 conductive line that is grounded at its distal end. Alternatively, there can be dedicated areas for inspecting particular buried layers (e.g., as described with reference to FIG. 4d). For example, a first area may include test structures having taps to a first buried layer, and a second area may include test structures having taps to a second buried layer.

Additionally, the above described taps may also be each coupled to a probable pad. Thus, parametric information regarding a buried layer may also be obtained. That is, standard wafer probing techniques may be utilized on the finished, or partially finished, wafer to inspect buried structures (e.g., conductive interconnect lines). For example, leakage current may be measured in a buried interconnect structure having a short. Additionally, mixed signal tests may also be performed on the buried structure via the probable pad. In this embodiment, parametric information and voltage contrast information may be obtained from a buried structure. One such probable test structure in described below with reference to FIG. 31.

G. Via Chains

As is described more fully below, the second test structures 404 preferably comprise rows of first via chains 500 that may be formed in one specified module (see FIGS. 14a–14b), and second chains 501 formed in another module (see FIG. 4c) in portion 208 of the test die 204. The via chains 500 and 501 extend parallel to the edges 204B and 204D, and between the proximal and distal edges 208A and 208B of the test die 204 (e.g., of FIG. 4c). In a specific embodiment, proximal ends 502 of the via chains 500 and 501 are located at the proximal edge 208A of the portion 208 of the test die 204 (e.g.., of FIG. 4c), and distal ends 504 of the vias 500 and 501 are located at the distal edge 208B of the die portion 206. It is understood that, the second test structure 404 exemplified in FIG. 5 may represent plan view of any of the via chains constructed between any of the metal layers, such as between M1 and M2, M2 and M3 or M3 and M4, etc.

Figure 14A:
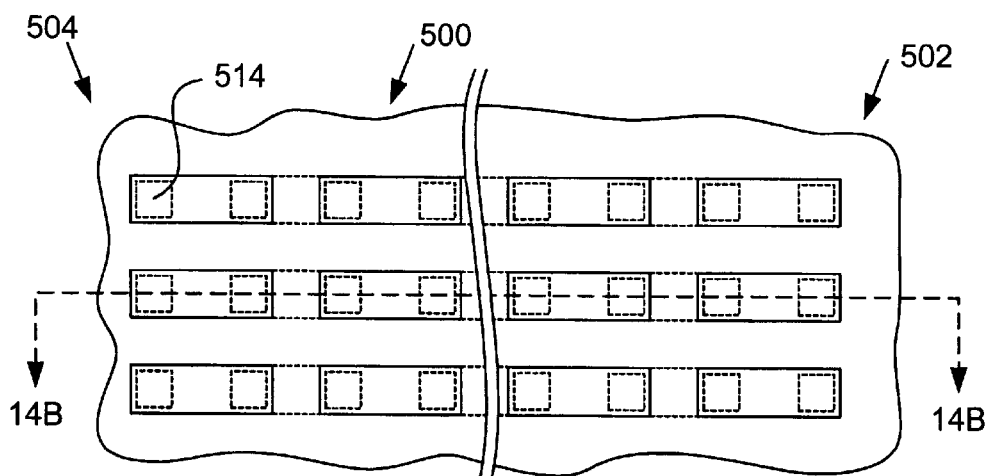
FIGS. 14a through 14c exemplify a part of a test structure comprising an array of via chains.
Figure 14B:
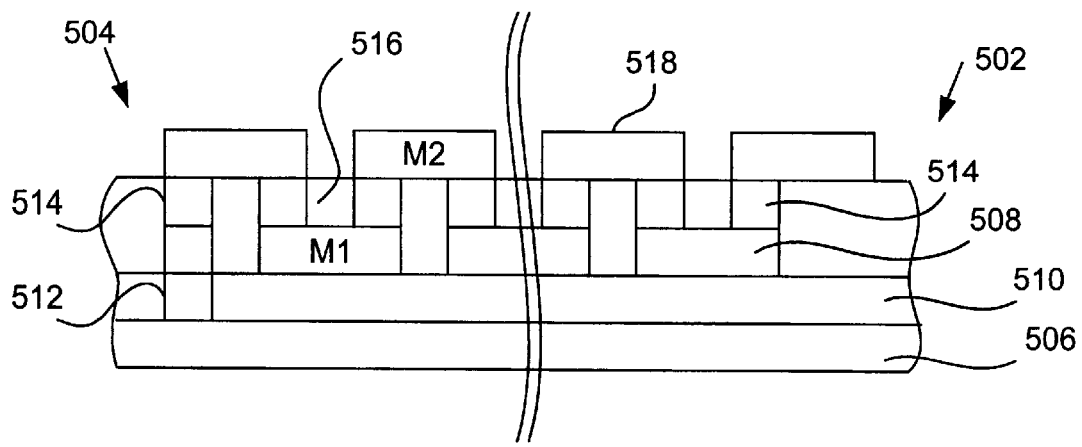

FIGS. 14a and 14b exemplify a part of the test structure 404 comprising an array of via chains 500, constructed between an M1 interconnect and an M2 interconnect, having a proximal end 502 and a distal end 504. Referring to FIG. 14b, in cross section, via chains 500 may be constructed over a substrate 506 that is isolated from an M1 interconnect line 508 by an oxide layer 510. A contact 512 formed through the oxide 510 grounds the M1 interconnect 508, and hence the via chain 500 to the substrate 506. A series of vias 514 formed through an interlayer dielectric 516 connects M1 and M2 interconnects 508 and 518.

As is described below, the via chain test structure 500 allows opens-only test types to detect opens in via chains. At this step of the process, an electron beam probe may be scanned across exposed metals of the M2 interconnects at the proximal end 502 to detect defects, for example, opens, in the test structure 404. If the via chain does not have opens, electrons from the beam will find a path to ground and secondary electrons will be emitted from the top M2 interconnect indicating that the via chain is good. However, if the chain is broken, the M2 interconnect will remain dark and will be registered by the system as a potentially defective chain for further processing.

Figure 14C:
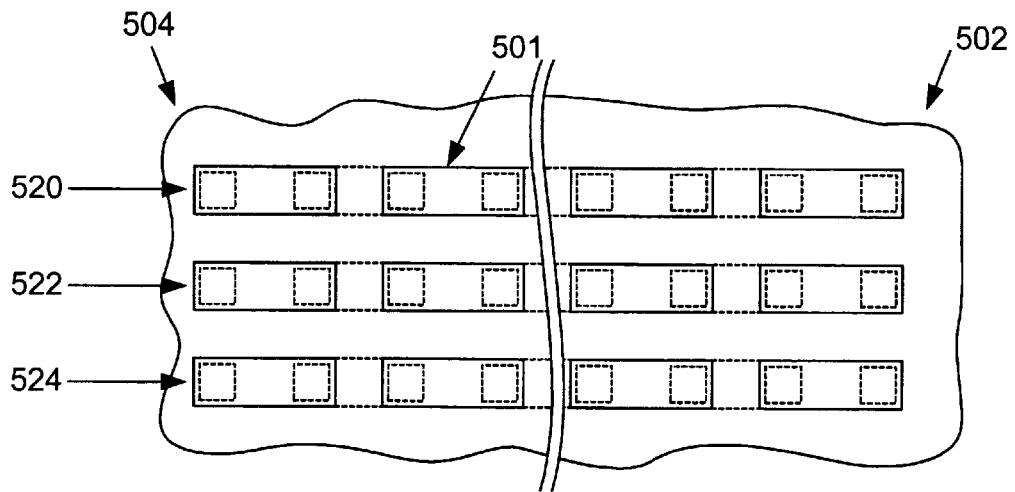

The via chains 501 shown in FIG. 14c are configured such that both shorts between the neighboring chains as well as opens in individual via chains can be advantageously observed. For this purpose, the via chains 501 are formed as in the manner the via chains 500 are formed, as shown in FIG. 14b, except that every other via chain is not grounded to the substrate. For example, in FIG. 14c, while a first row 520 and a third row 524 of via chains 501 are grounded at the distal end 504, a second row 522 is not grounded. Since the via chain at row 522 is not grounded to the substrate and cannot generate secondary electrons, it remains dark as long as it is not shorted to the neighboring grounded via chains. When the via chain at row 522 is shorted to the via chain at a next row, for example 520, the neighboring chain 520 provides a path for the electrons to the ground and secondary electron emission occurs in both the via chain in row 522 and 520, thus indicating a short-type defect. Moreover, grounded via chains at the first and second rows 520 and 524 are used to observe opens in the via chains as described for the via chains 500 in FIGS. 14a–14b.

H. Test Structures for Defects Caused by Chemical Mechanical Polishing

As is described more fully below, the third test structures 406 are located on the intermediate portion of the exemplary test die 204 and distributed along the scan direction 'A' shown in FIG. 5. As previously mentioned, the third test structures may, for example, comprise arrays of isolated contact test structures, CMP test structures, overlay test structures and CMP dummy metal test structures. Each of these structures may be contained within a plurality of modules.

One aspect of the present invention is able to detect defects caused by the chemical mechanical polishing (CMP) process. As is well known in the art, the CMP process is often used to planarize profiles that build up during multi-level deposition processes. As various layers are etched into the patterns during the process, the surface becomes uneven. In order to perform subsequent photolithographic process steps, such unevenness is planarized by the CMP process. However, the CMP process may polish away functioning circuit parts or cause unwanted density, pitch and or rise in the horizontal aspect ratio (length:width). Thus, it is desirable to detect defects created by the CMP process.

In one embodiment, several test structures for detecting defects caused by the CMP process are provided. Several different structures for detecting defects resulting from the CMP process are discussed below. Typically, these test structures will reside in whole or in part within the scanned swath of the test chip.

1. Test Structures for Detecting Pitch CMP Defects

Figure 16A:
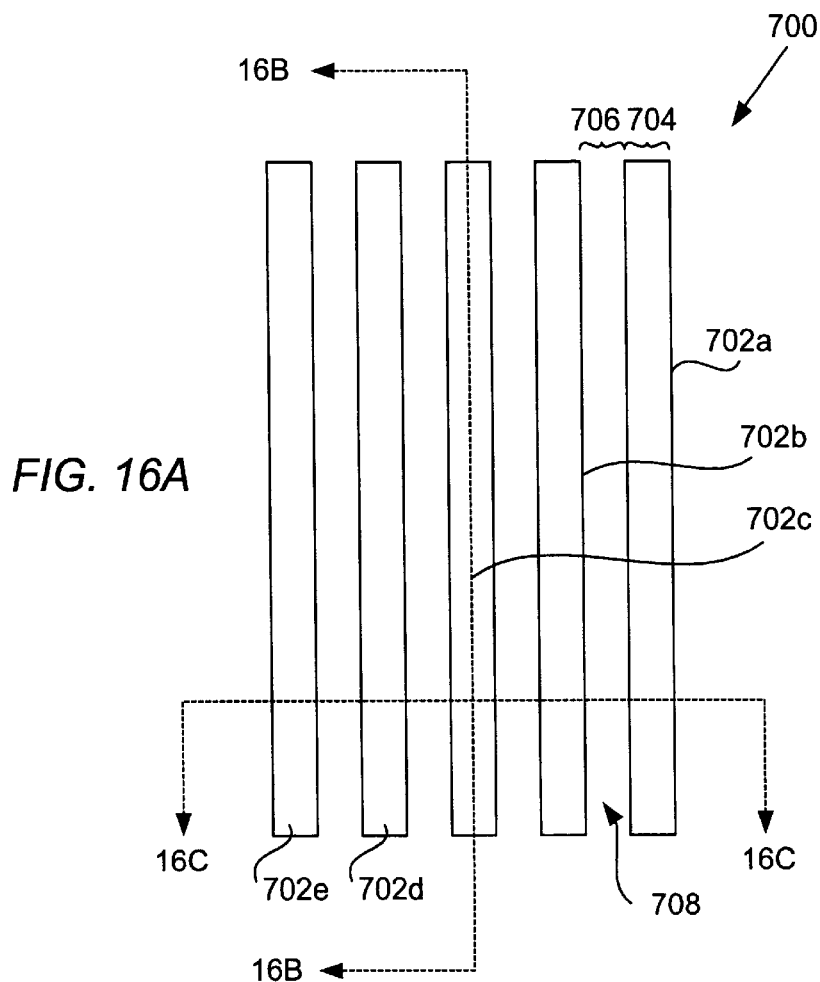
FIGS. 16a through 16c illustrate a CMP pitch test pattern.
Figure 16B:
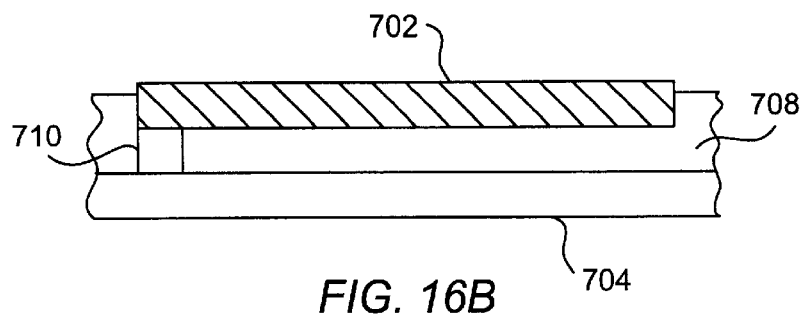
Figure 16C:
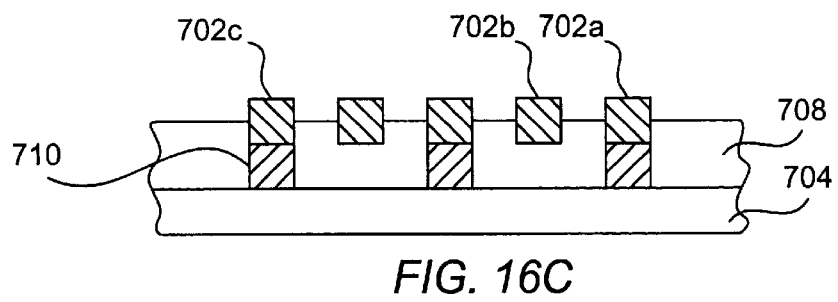

The test structure illustrated in FIGS. 16a–c exemplifies a CMP pitch test pattern 700. In this pattern 700, test elements 702, such as metal lines representing M1 interconnect lines, have substantially the same line width 704. Each metal line 702 is separated from one another by a space 706 that is substantially equal to the line width of the test line. Therefore, the test pattern 700 has a fixed density of about 50% line area. The test pattern 700 is configured such that every other metal line in the pattern is grounded (see FIG. 6c). FIG. 6b illustrates one of the metal lines 702 that is grounded to a substrate 704 by a contact 710 formed through an isolation layer 708. Such test patterns can be formed in a plurality of modules and in different critical dimensions on the test die.

During the electron beam inspection, as the probe is scanned across the metal lines 702 of the pitch test pattern 700, if there are no defects, grounded metal lines will emit secondary electrons indicating that all lines are good. If one of the grounded lines is open, that line will remain dark, indicating a defect. If one of the ungrounded lines is shorted to one of the neighboring grounded lines, both lines will emit secondary electrons, thereby indicating the short between them.

As mentioned above, in a preferred embodiment of the present invention, the CMP pitch test patterns will generally be located in whole or in part within the scanned swath of the test chip. In this manner, the test patterns can be tested for defects during the scan of the scanned swath.

The CMP pitch test structures will preferably comprise metal lines that are less than 20 $\mu$m in length. More preferably, such test structures comprise metal lines that are about 10 $\mu$m or less in length. Still more preferably, such test structures comprise metal lines that are 5 $\mu$m or less in length.

A test chip may have various CMP pitch test structures, each with a different pitch. The width of the metal lines in the test structures with the widest lines will typically have lines of about 2 $\mu$m to 3 $\mu$m wide. Other CMP pitch test structures on the test chip may comprise significantly thinner metal lines, such as lines as thin, for example, as 0.05 $\mu$m. Preferably, a majority of the CMP pitch test structures on the test chip will generally comprise metal lines of a width less than 0.5 $\mu$m. More preferably, the majority of the CMP pitch test structures on the test chip will comprise lines of a width less than 0.2 $\mu$m.

Typically, the CMP pitch test structures on a test chip will each cover the same area (for example, 10 $\mu$m by 10 $\mu$m or 5 $\mu$m by 5 $\mu$m) such that all of the CMP pitch test structures have lines of substantially the same length. However, the number of lines in a CMP pitch test structure will be inversely proportional to the width of the lines in the test structure. For example, if the width of the lines is 1 $\mu$m, a 10 $\mu$m CMP pitch test structure will comprise five lines and if the width of the lines is 0.5 $\mu$m, a 10 $\mu$m CMP pitch test structure will comprise 10 lines.

In order to save space on the test chip, multiple CMP pitch test structures can be placed together in a row. Generally, in such an instance, the width of the metal lines among the multiple test structures will vary. For example, six CMP pitch test structures might be placed in a row in the x-direction with each of the metal lines in the test structures extending in the y-direction. The first and sixth test structures might have wide lines, with the second and fifth test structures having narrower lines and the third and fourth test structures having still narrower lines. It should be noted, however, that in this example, it would be preferred that the "wide lines" be no more than 1.25 microns wide.

2. Test Structures for Detecting Density CMP Defects

Figure 17:
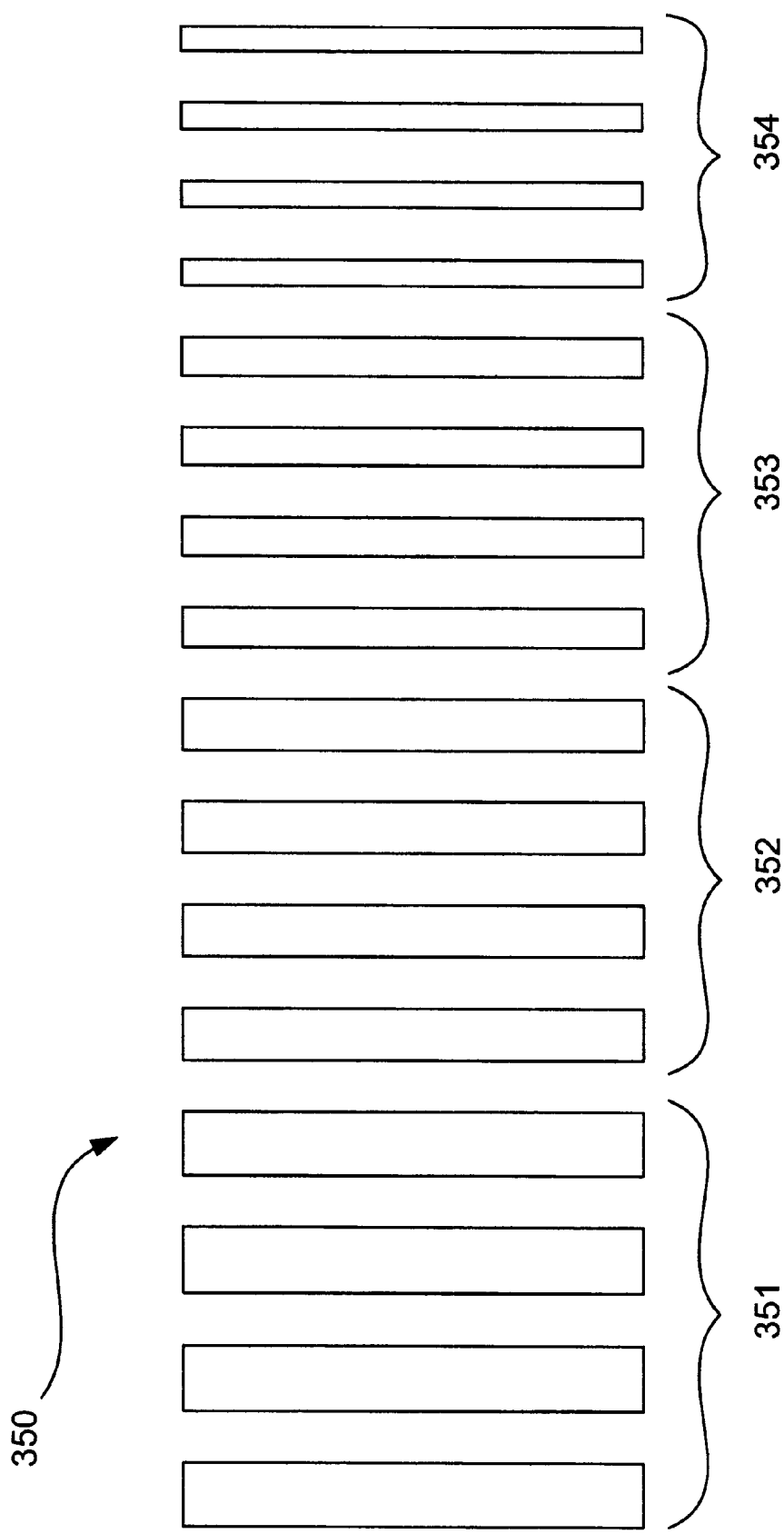
FIG. 17 illustrates a CMP density test pattern.

FIG. 17 shows a section of a CMP density test pattern 350 to monitor the effects of the CMP process on patterns having metal lines with differing line widths and line space between the neighboring metals lines. The CMP density test pattern 350 as shown in FIG. 17 has four sections (351, 352, 353, and 354), each section having four metal lines. In section 351, the metal lines take approximately 50% of the space. In section 352, the metal lines take approximately 37% of the space. In section 353, the metal lines take approximately 25% of the space. And, in section 354, the metal lines take approximately 12% of the space. It is preferred that the lines of each section be of substantially equal length and width, as is illustrated in FIG. 17.

Similar to the test pattern discussed above with respect to CMP pitch testing, the density test pattern illustrated in FIG. 17, is configured such that every other metal line is connected to ground. As such, the density test pattern can be tested using voltage contrasting in the same manner as is described in connection with the CMP pitch testing pattern.

The dimensions of each section in the example illustrated by FIG. 17 is 5 $\mu$m by 5 $\mu$m. As such, the width of each of the metal lines in section 351, for example, is 0.625 $\mu$m, as is the width of each of the spaces between the metal lines. The length of each metal line in the pattern is 5 $\mu$m.

In the example provided by FIG. 17, the width in the lines in each section is substantially equal in both length and width. Further, the spaces in each section are also substantially equal in both length and width. Further, each section takes up the same space (real estate) on the test chip. In addition, in the pattern, the width of a line together with the width of the space to its right equals a constant—in this example 1.25 $\mu$m.

It should be noted that the pattern shown in FIG. 17 could have additional lines extending both to the left and the right. For example, to the left of section 351, there might be one or more sections wherein the four metal lines are wider than the spaces that separate them. To the left, there might be one or more sections wherein the four metal lines are narrower than the metal lines in section 354.

It should also be noted that the metal lines might be significantly longer than 5 μm and still be within the scope of the invention. Preferably, however, each metal line will be no longer than 10 μm. More preferably, each metal line will be approximately 5 μm or less in length. At the same time, it should be noted that, in a particular section, the metal lines can be of any width that fits within the real estate allotted to a metal line and its adjacent space. For example, a metal line might take up 100% of the allotted real estate. Or it can take, for example, closer to 4%, or even less.

Furthermore, the number of metal lines per section can vary. In the preferred embodiment, each section has an even number of metal lines, more preferably eight. However, a section can consist of an odd number of metal lines. Furthermore, it is possible to have sections within a single pattern that have differing numbers of metal lines.

In a specific embodiment the density test pattern will reside within the scanned swath of the test chip, either in whole or in part, so that it is scanned and voltage contrast analysis can be applied. It is preferred that each metal line in the density test pattern reside entirely within the scanned swath so that it can be scanned. However, the metal lines in the pattern might reside only partially within the scanned swath and still be scanned such that voltage contrasting methods are applied.

Figure 18:
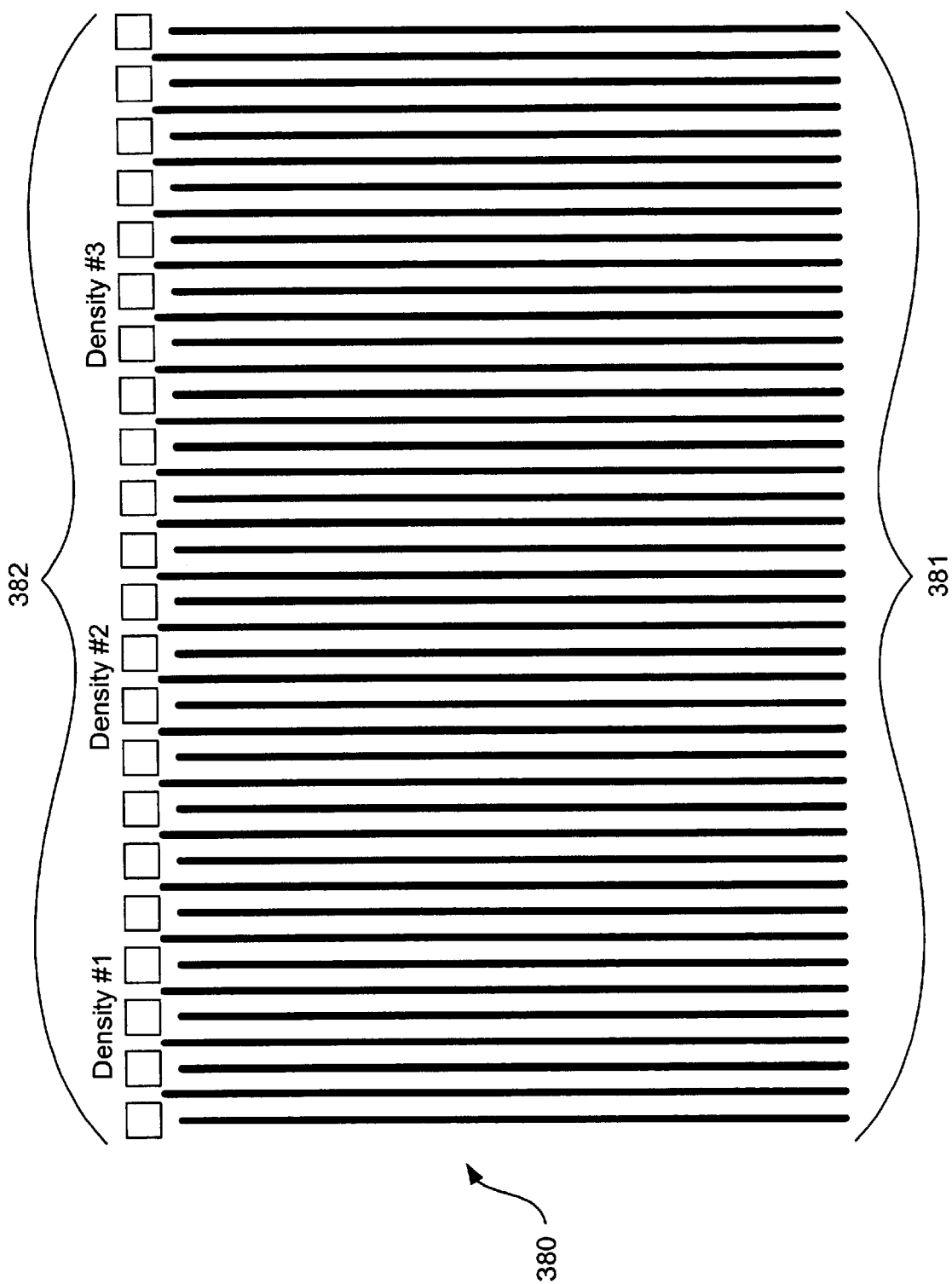
FIG. 18 illustrates a further CMP density test pattern.

FIG. 18 provides a further example of a density pitch pattern 380 for CMP defect-related testing. The pattern comprises a plurality of metal lines 381 with a plurality of contacts to ground 382. The pattern shown in FIG. 18 illustrates three different density patterns. In the embodiment shown here, the metal lines in the test pattern are 5 microns or less in length and the widest line (Density #3) is 0.2 microns or less in width. The metal lines in the plurality of metal lines 381 are alternately electrically isolated.

3. Test Structures for Testing Horizontal Aspect Ratio

Figure 20:
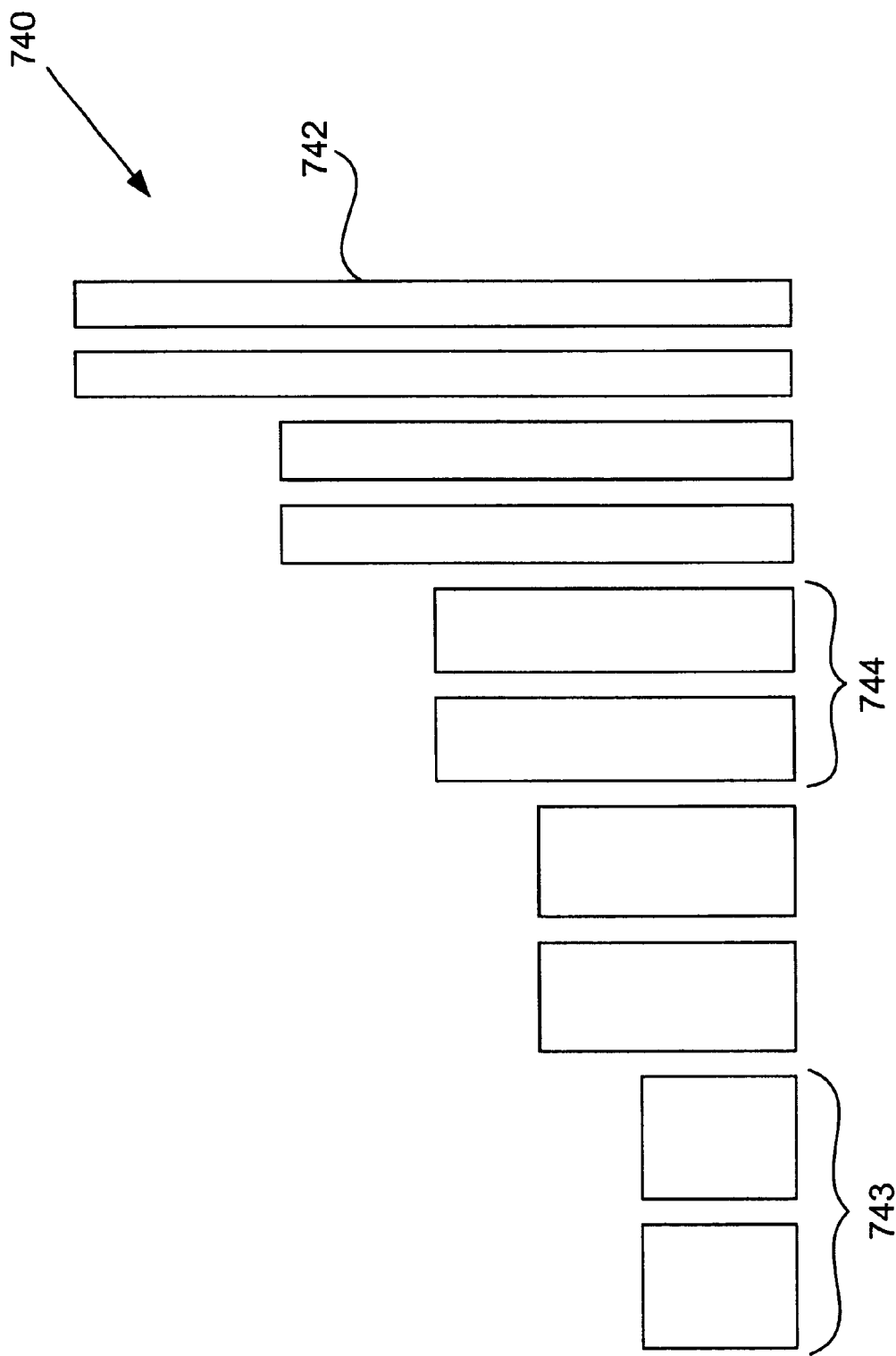
FIG. 20 shows a section of a CMP aspect ratio test pattern.

FIG. 20 shows a section of a CMP aspect ratio test pattern 740 comprising metal lines 742 having different width and length to accommodate reasonable utilization of the real estate on the test die. As can be seen in FIG. 20, the lines in pattern 740 rise in the horizontal aspect ratio from left to right. Also, the length increases from left to right, while the width increases from right to left. Similar to the previously described CMP test structures, in this configuration every other metal line is grounded to the substrate and test structure 740 is repeated in various modules with different critical dimensions. As can also be seen in FIG. 20, in one embodiment, the lines are paired into lines with the same horizontal aspect ratio (and preferably the same dimensions). In each such pair (e.g., pairs 743 and 744), one of the lines is electrically isolated (floating) and the other is not electrically isolated (preferably connected to ground).

It should be noted that the pattern 740 can be repeated on the test die with increasing or decreasing space between lines. This is true of any horizontal aspect ratio test pattern. Such repetition (repeated test patterns with increasing or decreasing space between lines) can be utilized to develop a row of test patterns on the substrate.

Figure 19:
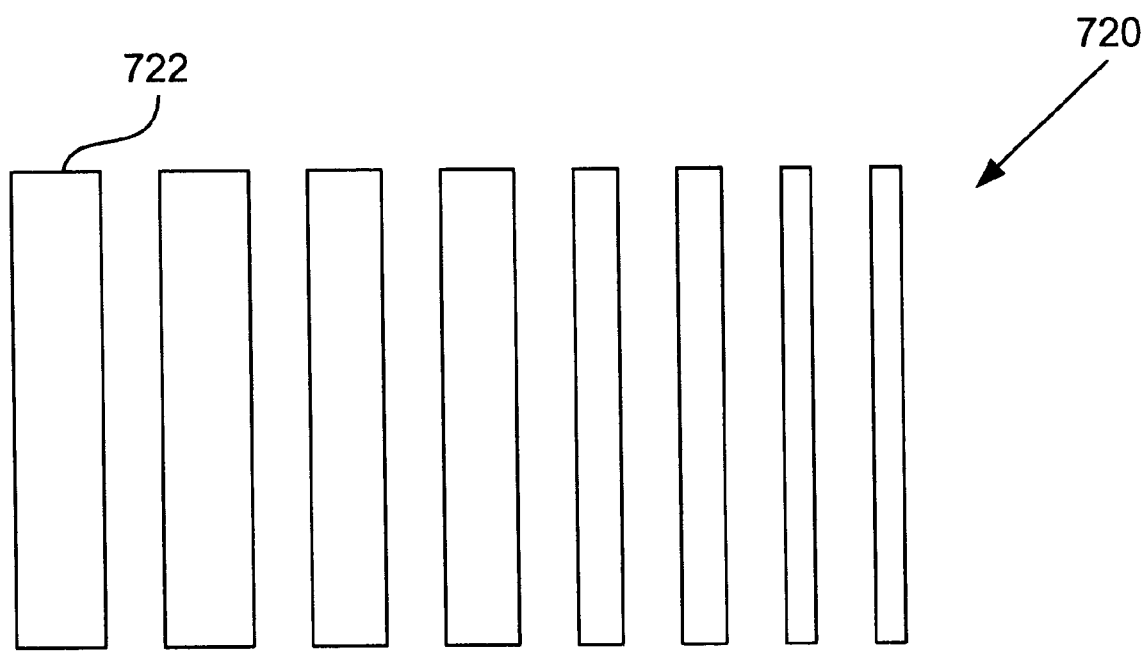
FIG. 19 illustrates a CMP horizontal aspect ratio test pattern.

FIG. 19 illustrates another horizontal aspect ratio test pattern 720. Here the horizontal aspect ratio increases from left to right, but the length of the lines remains the same, preferably no more than 10 microns and even more preferably no more than 5 microns. This pattern can be repeated on the test die similar to the test pattern of FIG. 20. Again, the lines of test pattern 720 are paired into lines of equal dimension, with the lines in the pair alternately electrically isolated. Test patterns 720 and 740 are inspected the same way as the CMP pitch test structure 700.

Figure 21:
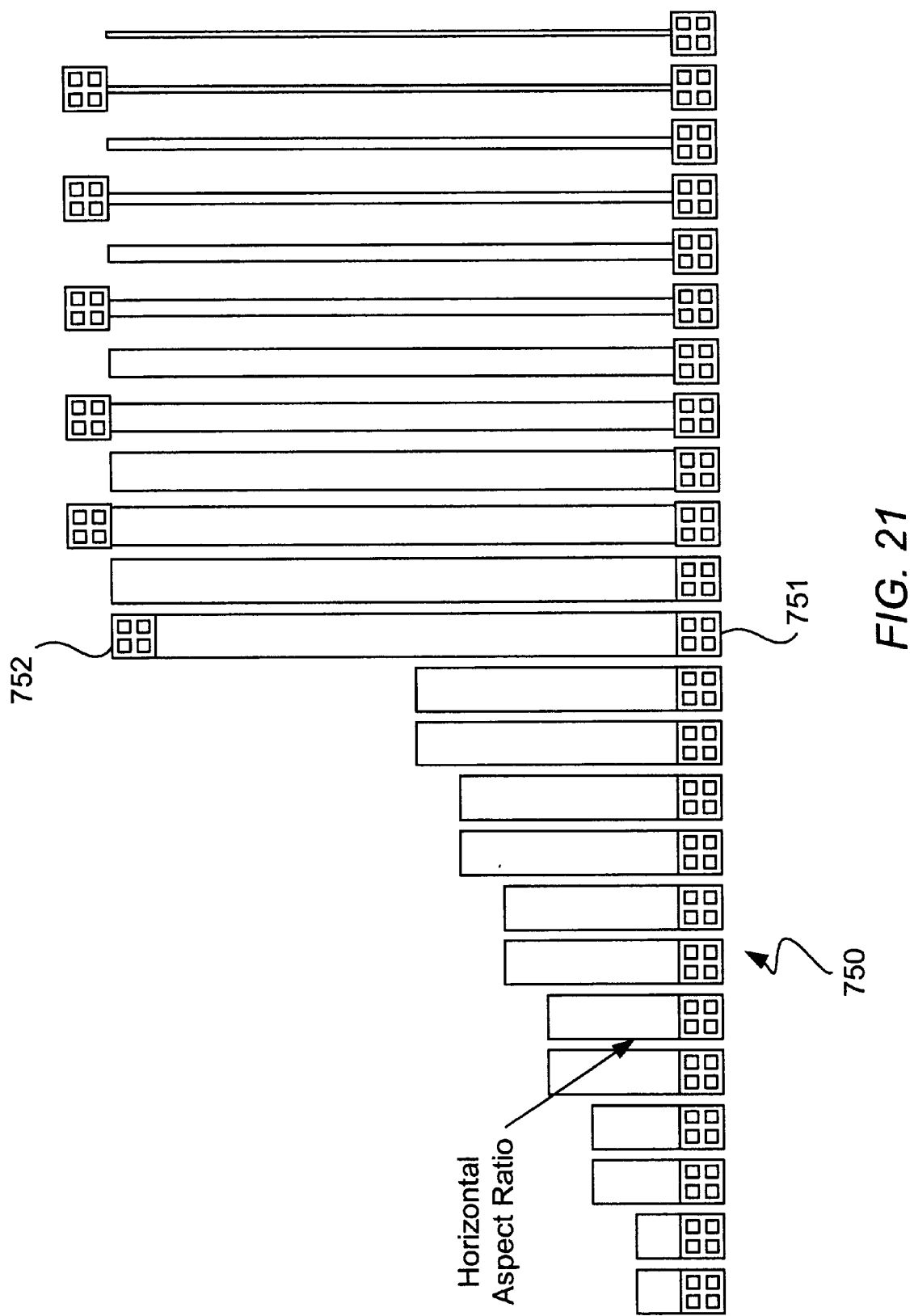
FIG. 21 shows a section of a CMP aspect ratio test pattern.

FIG. 21 illustrates an additional horizontal aspect ratio test pattern 750. The pattern comprises metal lines in increasing horizontal aspect ratio from left to right. Every other line has a contact to ground 752. On the bottom of each line is a scan structure, which is of uniform size throughout the pattern 750. In one embodiment of the present invention, the metal lines would be scanned along the scan structures (in order to insure better uniformity). However, such scan structures are not required to practice the present invention. It should be noted, however, that such scan structures can also be utilized in the other CMP patterns (pitch and density) described above.

I. Contact Arrays

Figure 15A:
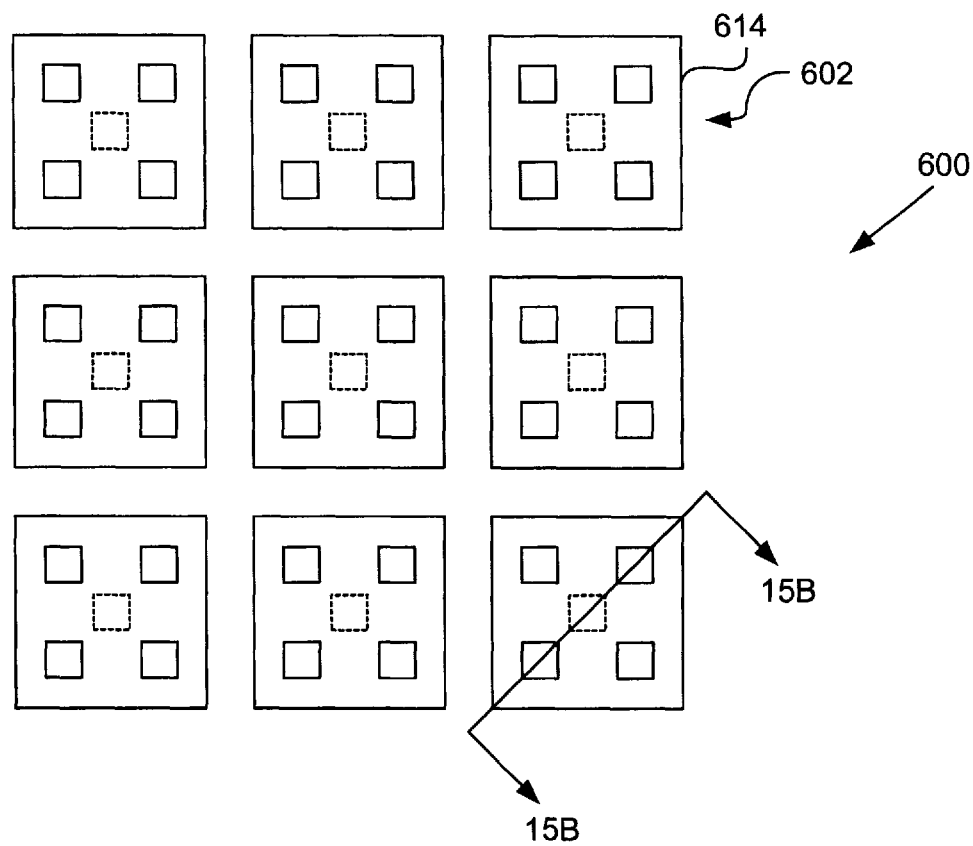
FIGS. 15a and 15b show an exemplary array of isolated contact test structures.

FIG. 15a shows an exemplary array 600 of isolated contact test structures 602 that is located on the intermediate portion 210. Such structures enable monitoring of defective contacts in integrated circuits.

Figure 15B:
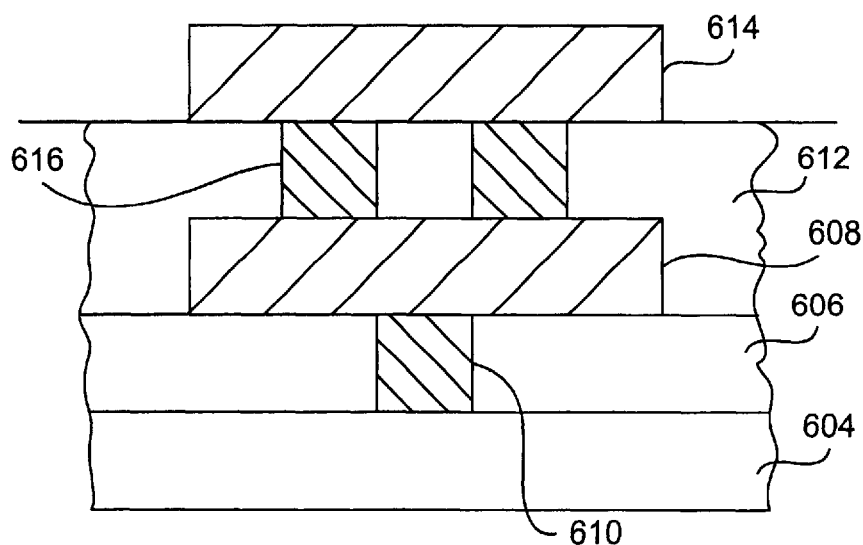

Rows of the array 600 preferably extend parallel to the proximal edges 206A and 208A of the first and second portions 206 and 208 of the test die 204 (See FIG. 4c). FIG. 15b exemplifies the multilayer construction of the isolated contact test structure 602 formed on a substrate 604 using conventional semiconductor processing techniques. An isolation layer 606, such as an oxide layer, isolates a M1 layer portion 608 (M1 pad), from the substrate 604. A contact 610 formed through the isolation layer 606 connects the M1 layer to the substrate 604. Preferably, an interlayer dielectric 612 isolates the M1 layer portion from a M2 layer portion 614 (M2 pad). M2 layer portion is connected to the M2 layer portion by vias 616 formed through the interlayer dielectric 612, thereby establishing a ground connection for the M2 pad 614. In the illustrated embodiment, M1 and M2 layer portions 608 and 614 are connected with four vias, which will be referred to as redundant vias. In this embodiment redundant vias 616 help to monitor defective contacts without concerning about failing vias, thus limiting the failure mechanism to the contact 610. This configuration shown in FIGS. 15a and 15b assures that the random defects, in any of the vias 616, do not prevent contact to the substrate 604. As long as one of the vias 616 is not defective, ground connection between the M2 pad and the substrate will be established.

During the electron beam inspection, as the probe is scanned along the rows of exposed metal of M2 pads 614, if the contact 610 is not open the electrons from the beam will find path to the ground and secondary electrons will be emitted from the pad 616 indicating that the contact is good. If the contact is open, the pad 616 will remain dark.

J. Test Structures to Monitor Misalignment

Figure 22A:
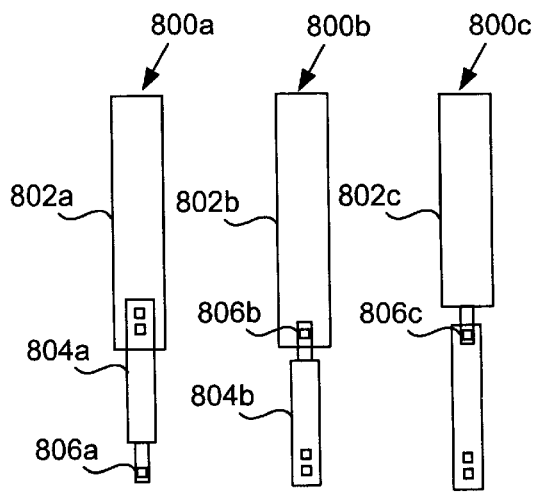
FIGS. 22a and 22b show top view test structures used to observe misalignment problems.
Figure 22B:
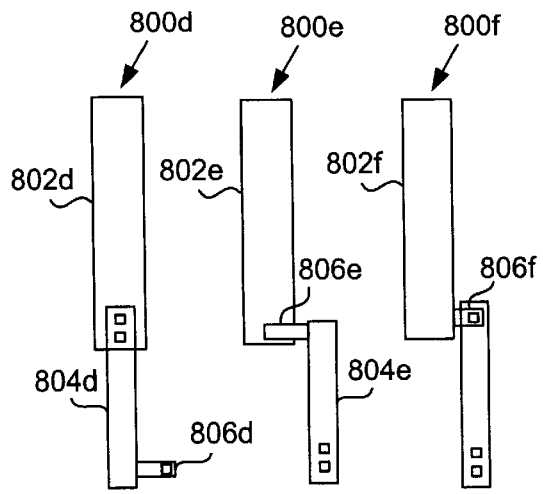
Figure 22C:
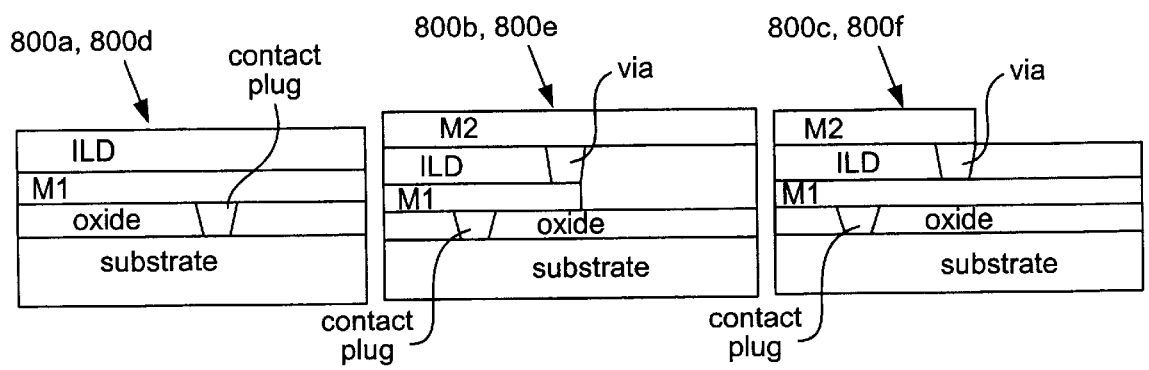
FIG. 22c shows a cross section of the test structures of FIGS. 22a and 22b.

As is well known in the semiconductor industry, each step of IC manufacturing requires precise alignment control in order to prevent unwanted contacts between devices or changes in device dimensions. FIGS. 22a through 22c show six types of overlay test structures 800a through 800f used to observe misalignment problems occurring during the manufacturing process, such as those that occur during the patterning of metal layers. Test structures 800a and 800d are "M1 to contact" type structures and have strips of M1 metal (804a and 804d, respectively) extending over a contact (806a and 806d). Test structures 800b and 800e are "via to M1" type structures and have a M2 via (806b and 806e, respectively) over a M1 metal strip (804b and 804e). Test structures 800c and 800f are "M2 to via" type structures and have strips of M2 metal (802c and 802f, respectively) extending over a via (806c and 806f). Each type includes a test structure for measuring misalignment in the x direction (e.g., FIG. 22a), as well as the y direction (e.g., FIG. 22b). Of course, any other misalignment direction may be used.

Figure 23A:
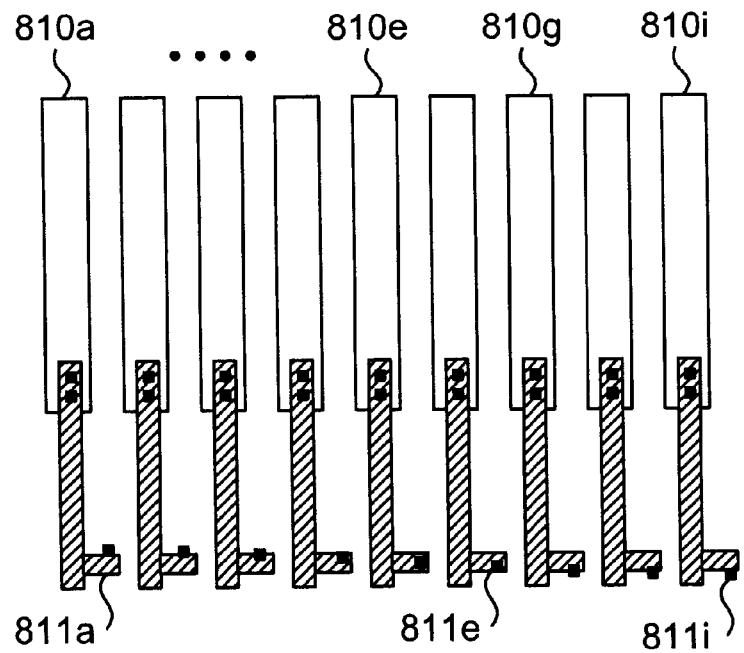
FIGS. 23a and 23b shows an array of test structures used to observe misalignment and amount of misalignment in the y direction and x direction, respectively.
Figure 23B:
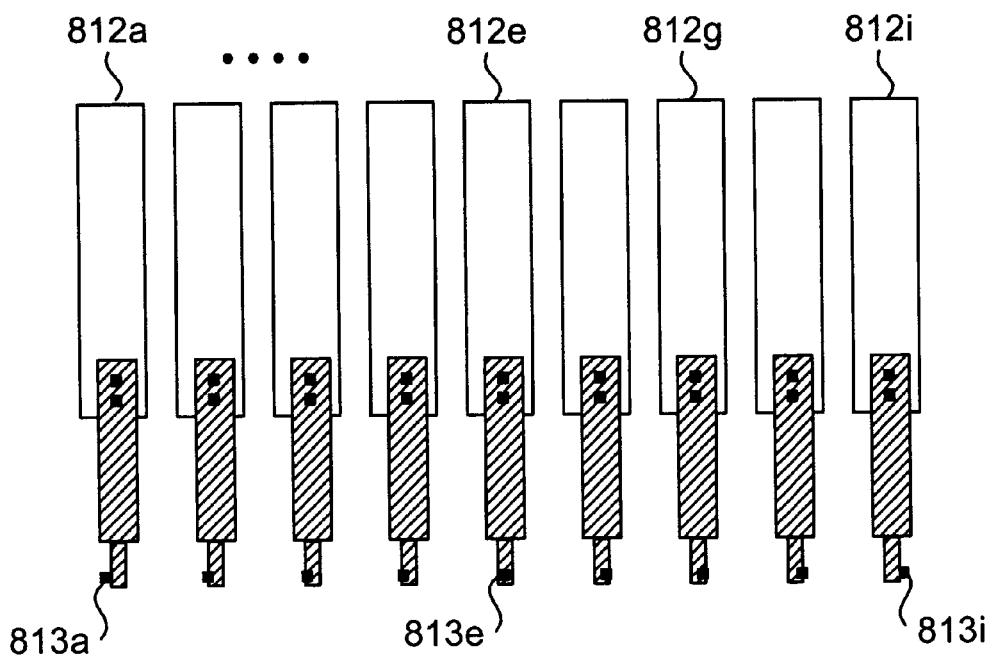

As exemplified in FIGS. 23a and 23b, each test structure may form part of an array that is utilized to determine whether a misalignment has occurred and a measurement of such misalignment. An array of "M1 to contact" type structures are shown in both FIG. 23a and 23b. The structures are fabricated to be almost identical to each other, except for positioning of a contact (e.g., 811 or 813). As shown in FIG. 23a, the middle test structure 810e has a contact 811e that is perfectly centered when there is no misalignment. The structures to the right of the middle structure have incrementally misaligned contacts in the negative y direction. The rightmost contact 811i is misaligned so that it no longer touches the M1 layer. In contrast, the structures to the left of the center are incrementally misaligned in the positive y direction. the leftmost contact 811a is misaligned so that it no longer touches the M1 layer. Similarly, the test structures of FIG. 23b are incrementally misaligned in the positive and negative x directions.

The contacts 811 and 813 are tied to the substrate and grounded. Thus, if the test structures are aligned, particular test structures will be touching the contact and others will not. As a result, during voltage contrast testing, the contacting test structures should appear bright, while the non-contacting structures should appear dark. In the illustrated example, the test structures 810a, 810i, 812a, and 812i (which do not touch the contacts 811 or 813) should appear dark, and the remaining structures should appear bright.

However, when there is a misalignment, some of the test structures that are expected to appear bright may actually appear dark, and some of the structures that are expected to appear dark may appear bright. The relative positions of the contacts 811 and 813 are chosen so that a misalignment may be readily measured. For example, the contacts of the array are designed to be offset from M1 by increments of 0.0005 $\mu$m. Thus, the misalignment amount may be determined by how many test structures appear dark. For example, if only the two rightmost test structures 810g through 810i (and the leftmost structure) appear dark, the misalignment is 0.0005 $\mu$m or less in the negative y direction.

When using die to die comparison mode for defect analysis, the overlay structures must have a set of corresponding structures of which none are connected to ground. These ungrounded structures serve as references and are compared to the grounded structures to ensure that all connected overlay structures are detected. If the reference structures are not provided the results from the overlay structures will not be consistent.

K. CMP Dummy Metal Filings

Figure 24A:
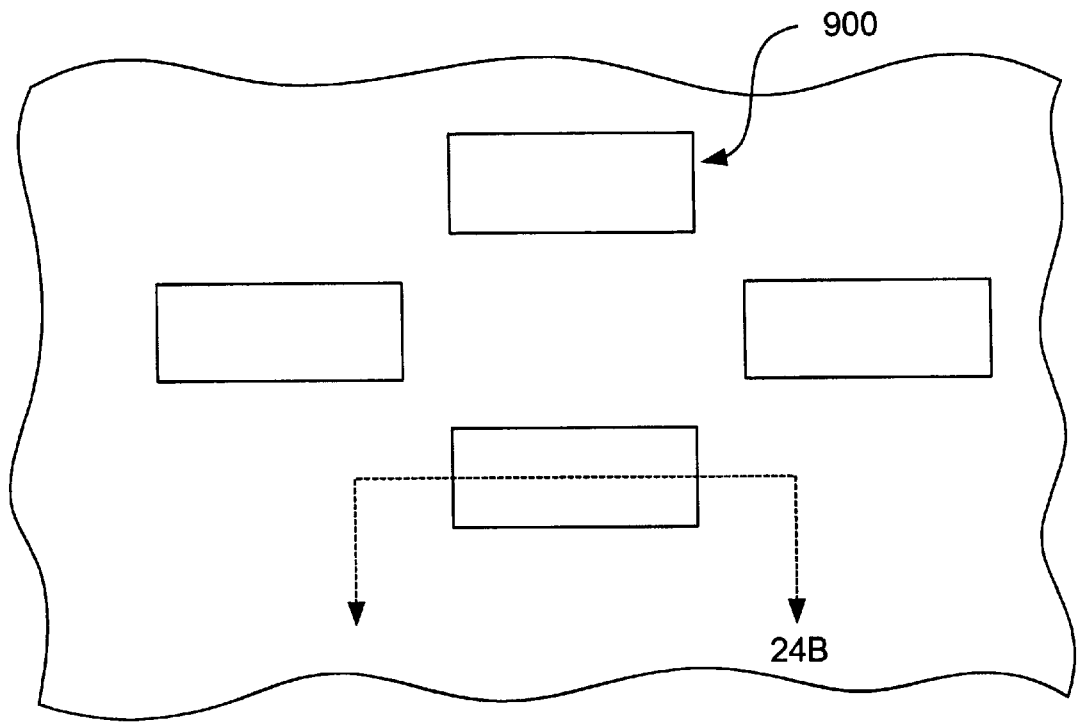
FIGS. 24a and 24b exemplify a multilevel test structure converted from a metal filler for monitoring the integrity of the CMP process with the addition of vias and/or contacts.
Figure 24B:
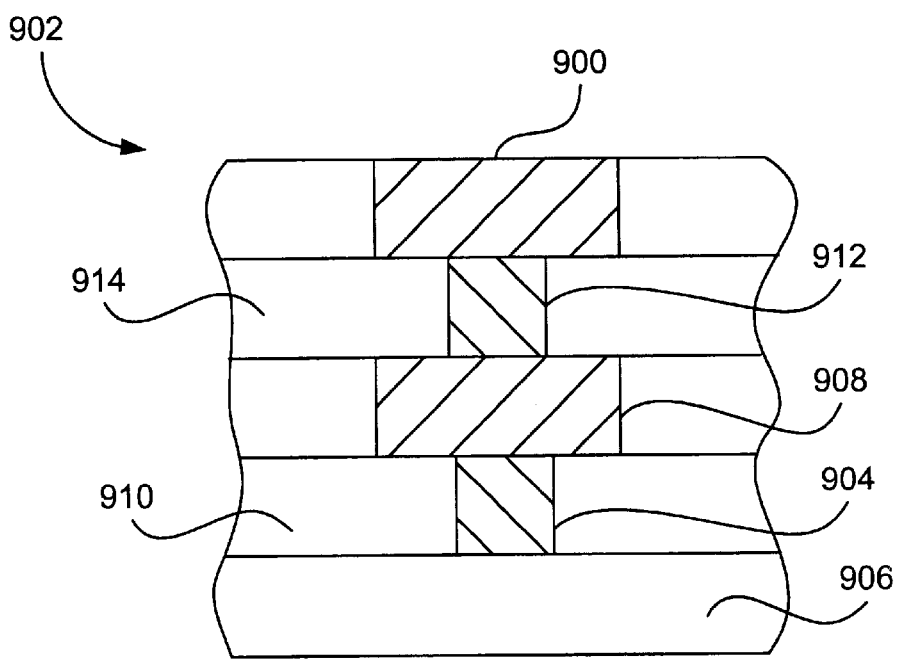

Another test structure that may be formed within the intermediate section 210 of the test die 204 is the test structures using CMP dummy metal filings as a test pad to test for vias. As is commonly known in the art, CMP dummy fillings are auxiliary metal structures CMP process integrity distributed on a wafer to facilitate an even polishing of a surface of the wafer. They prevent rapid erosion of relatively soft materials located on the surface when such materials are neighboring harder materials. In one embodiment, as shown in FIGS. 24a–24b, a metal filler may be converted to a multilevel test structure to monitor the integrity of the CMP process with the addition of vias and/or contacts.

In one exemplary test structure 902, a contact 904 is formed between a substrate 906 and a first metal layer portion 908 (first metal pad), and through an isolation layer 910. The first metal pad 902 may be connected to the metal filler 900 by at least one via 912 formed through a interlayer dielectric 914. This structure 902 may have more metal layers above the metal under test (MUT) and more redundant vias between these metal layers. During the electron beam inspection, the probe is scanned along the rows of metal fillers 900. If a defect free path to substrate is established, metal filler 900 emits secondary electrons, indicating that the via and the contact are not open. If any one of them are open, the metal filler remains dark.

After the test chip is initially designed, it may be determined whether empty space requires dummy fillings to prevent defects caused by CMP polishing. Under current technology, this is often determined using software tools available in the marketplace. This determination will be based on the size and configuration of the empty space. Once this determination is made, according to the present invention, the dummy fillings can be fabricated as contacts that can be tested similar to the contacts of the contact arrays described above. In this manner, the empty space is utilized for testing purposes on the test chip. In addition, this same method can be utilized for empty space of VLSI products.

FIGS. 26a–26c illustrate the process for utilizing dummy shapes for purposes of testing for defects. FIG. 26a illustrates a product chip 900 with empty space 901. FIG. 26b illustrates a pattern of typical dummy shapes 902 used to fill up empty space on a product chip. FIG. 26c shows that contacts 904 have been added to some of the dummy shapes 903 to permit voltage contrast testing (the other dummy shapes are allowed to float). Such usable dummy shapes can be included in both dedicated test chips and product chips (for in-line voltage contrast testing).

L. Location and Characterization of Defects

As discussed above, once a defect is detected via the voltage contrast technique, it may be important to determine the location of the defect and to characterize it. Where the scan of the scanned swath has been in the x-direction, inspection of the test structure at issue may be required in the y-direction. For example, in connection with the exemplary test chip described above, a conductive line may prove defective based on the analysis of the scan of the primary scan area. As discussed above, these defect(s) may reside outside the scanned swath (i.e., primary scan area). In other words, the primary scan area is scanned first to determine whether the test structure contains one or more defect(s). Testing may then be performed in the y-direction to locate and characterize the defect(s).

Preferably, defects are located after completion of the scan in the x-direction. That is, all of the stubs of the conductive lines are scanned to determine if any conductive line is defective. The location of each defective stub and corresponding conductive line is then recorded. After all of the stubs are scanned, each conductive line may then be scanned in the y-direction in an efficient pattern. For example, if the stubs were scanned left to right in the x-direction, each conductive line is then scanned in the y-direction, starting with the leftmost line. In sum, scanning the test structure along the entire x-direction (prior to locating the individual defects) allows a quick assessment of the number of defects within the test structure. If required, the individual defects may then be located and characterized as described below.

Of course, any other suitable scan pattern may be implemented. For example, when a conductive line is found defective during an x-direction scan, the x-direction scan is halted and the defect is immediately located along the y-direction conductive line. The x-direction scan may then resume after the defect is located. However, this scan pattern is not as efficient as a scan pattern that allows the x-direction scan to complete prior to locating the defects.

Figure 25:
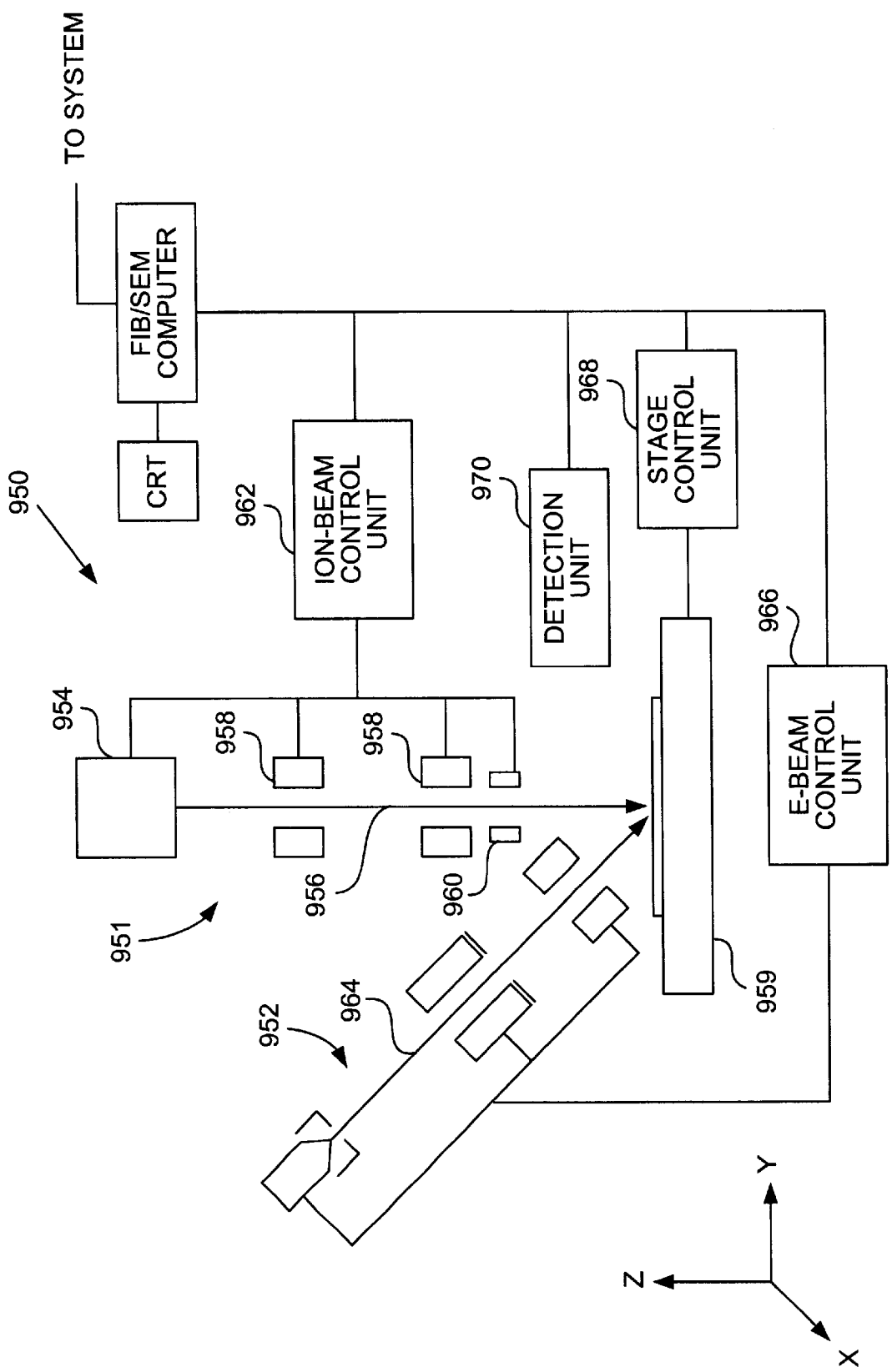
FIG. 25 is a diagrammatic representation of an analysis tool for analyzing a failed test die containing test structures.

Accordingly, once the defective structures on the die are relocated and identified, the exact location and the cause of the defects may need to be identified. In a specific embodiment, this can be carried out using an analysis tool. FIG. 25 shows a fundamental construction of an analysis tool 950 for analyzing a failed test die containing test structures. The analysis system may preferably comprise a dual beam analysis tool comprising both a Focused Ion Beam (FIB) unit 951 and an electron beam (SEM) unit 952. The analysis tool 950 is coupled to the system 10 of FIG. 1 and is a integral part of the system.

The system of 10 provides the recorded layout data for the defective structures of the test circuit and the type of the defect such as opens or shorts type of defects. The analysis tool 950 that is used in specific embodiments of the present invention is able to scan the defect containing locations with either a focused ion beam (FIB) or an electron beam to provide two different types of scanning action. The focused ion beam can be used to provide localized cutting or removal of the material from a defect containing location so as to expose underlying materials locally, thereby avoiding the need for removal of an entire layer or layers in certain instances. The electron beam can be used for chemical analysis using Energy Dispersive X-ray (EDX) analysis and imaging of the area under analysis.

As shown in FIG. 25, the exemplary FIB unit generally contains a liquid metal ion source 954 using gallium (Ga) to generate a Ga ion beam 956. A lens system 958 focuses the ion beam to a spot size on the test die of the wafer which is placed on a stage 959. A set of scan coils 960 is placed in the vicinity of the lens system 958. When energized, the scan coils 960 cause the ion beam 956 to scan over the test die. The output of ion source, lens system focusing, and scan coil actions are controlled by an ion beam control unit 962. During the material removal, the control unit 962 controls scanning of a target surface by focused beam with respect to scanning area, frequency, and time of scanning.

The focused ion beam, which is focused and scanned as mentioned above, irradiates a selected portion of defected structure. The acceleration voltage of ion beam 956 can range from 10 to 30 kev. Current of the focused ion beam 52 can be set between 10 pA and 1000 pA.

The scanning electron beam unit 952 irradiates an electron beam 964 on the die in the vicinity of beam 52. The acceleration voltage, current level and beam diameter of electron beam 964 are controlled by an electron beam control unit 966. The electron beam 964 is used for imaging, e.g., secondary and/or back scattering electron imaging, as well as EDX chemical analysis. The electron beam 964 may also be used to irradiate the area of interest on the die when that area is also being irradiated with the focused ion beam.

As mentioned before, the wafer under inspection is mounted on a stage 959, and further the stage is associated with a stage control unit 968 for displacing wafer stage 959 in x, y and z directions. A detection unit 970 may be placed at an appropriate location for detecting various signals generated at the surface of the wafer in response to irradiation by focused ion beam or electron beam. Although simplified in FIG. 25, it is understood that the detection unit 970 represents various detectors such as secondary electron, back scattering electron, x-ray or mass spectroscope or the like. A signal from the detection unit 970 is amplified and inputted into a FIB/SEM computer. The ion beam control unit 962, stage control unit 968 and the electron beam control unit 966 are also connected to the FIB/SEM computer system which is further connected to the system 10.

Once the defect site is relocated and marked, a chemical analysis known as EDX (electron dispersion X-ray) is performed at the location of interest. The EDX analysis is performed using electron beam unit 952 by focusing electron beam on the defective structure. Interaction of the beam electrons with the material atoms generates an X-ray spectrum which reveals the chemistry of the location under focus. When the X-ray spectrum of from the material is determined the most of the elements present at that location can be qualitatively identified, which may provide a determination of the cause of the failure. For example, if there is no tungsten at that location, the EDX spectrum should not show tungsten at that location. At his stage, if the cause of the defect is determined and identified, the process is completed and a new test die can be tested. Assuming that the initial inspection has not revealed the cause of the failure, FIB unit can be used to either strip back a layer or produce a cross-section using the focused ion beam to reveal cross sectional structure of the area of interest.

After the FIB stripping has been performed, the locations are then inspected once again using the scanning electron beam imaging and/or another EDX analysis and it is once again determined whether the cause of the failure can be identified. This process is repeated until the cause of the failure is identified. It will be appreciated that this process allows rapid corrective action to be taken in real-time in a manufacturing environment because once the cause of failure in the test structures is found, the manufacturing process of the wafers may be modified in order to improve the yield of the wafers.

In connection with the location of defects that have been detected, an additional technique can be utilized to locate a defect. The technique comprises pre-scanning the wafer under test with a dose that is designed only to partially charge the structures. Shorter lines will have less capacitance loading and will be charged more completely to the equilibrium potential. Thus, the potential of floating lines will vary approximately linearly with the length of the line. Longer lines will take longer to charge. The lines can then be scanned.

As such, defects on the line can be recognized, for example, by using the following technique:

1. If the line is at ground potential, the signal level from the end of the line will be mid level (say 50% of full scale);
2. if the line is full length and floating, then the signal level will be about 75% of full scale;
3. if the line is partial length and floating, then the signal level will approach 100% as the line length gets progressively shorter.

By calibrating the signal level versus position, one can infer the position of the end of the line and use this information to quickly move the wafer so the defect is in the field of view to image the defect for classification. Alternatively, each defective line may be scanned in an array mode to locate the defect. In general terms, a first field of view that is taken from a first portion of the line is compared with a second field of view taken from an adjacent second portion of the line. In one embodiment, the first field of view is subtracted from the second field of view. The subtraction result is directly related to whether the defect is located within the first or second field of view. Thus, the defect location may be determined based on such subtraction results.

M. Use of Voltage Contrast Testing in the Production of Product Chips

Figure 27:
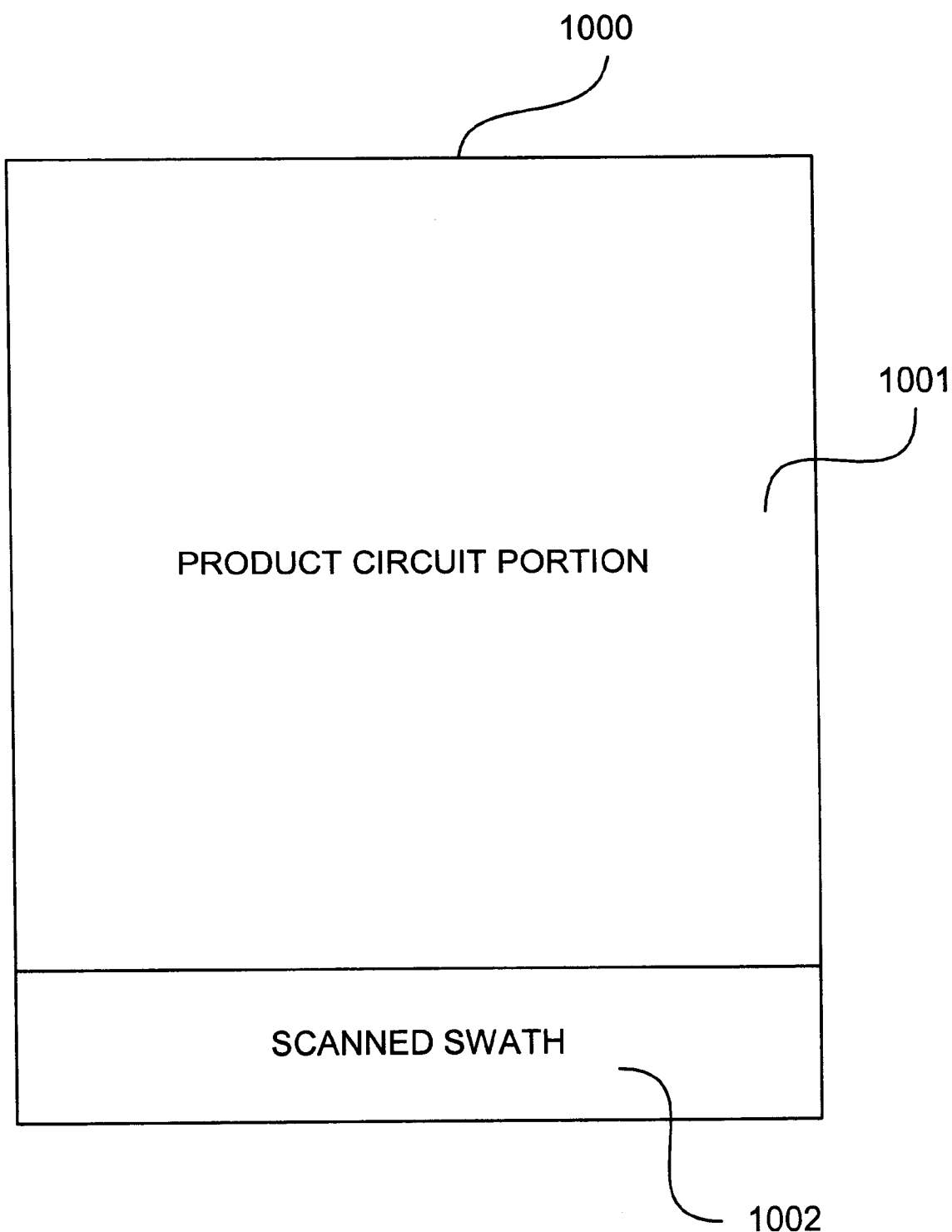
FIG. 27 illustrates a product chip.

The techniques and various test structures for voltage contrast testing are not only useful in the context of test chips, but can also be used in the context of product chips. FIG. 27 illustrates such a product chip 1000. The product chip 1000 has a product circuitry portion 1001 (which includes the circuitry needed to carry on the functions of the product chip) and a scanned swath 1002 at one edge of the chip. It is preferred that such a scanned swath be located at the edge of a product chip, but such location is not necessary in order to practice the present invention.

The scanned swath on a product chip can comprise any combination of test structures of the type described above. In fact, the exact combination of test structures may well depend on the particular circuitry of the product chip. Also, the exact combination may depend on particular concerns at the manufacturing plant. In any event, the scanned swath can be tested at a single point or multiple points during the manufacturing process. Moreover, during the manufacturing process, new test structures can be added to the scanned swath at any point of the manufacturing process and then tested.

Figure 28:
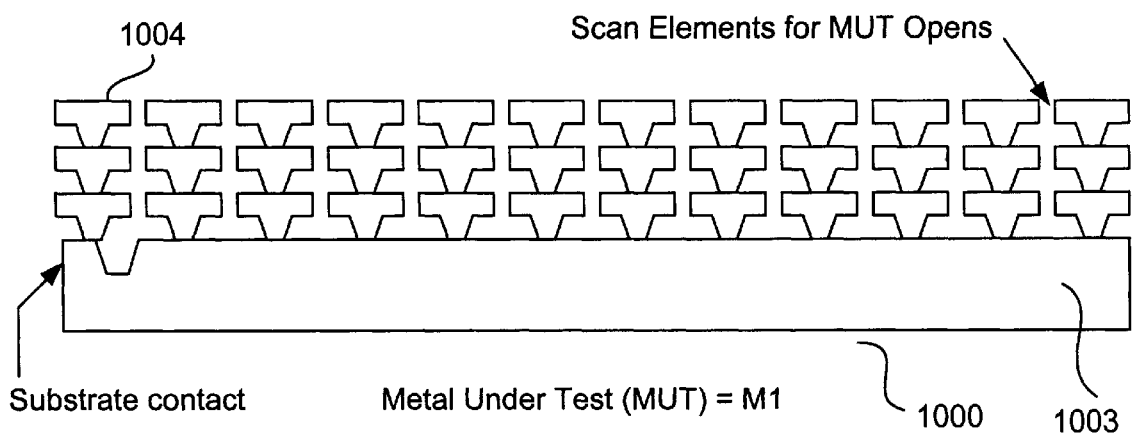
FIG. 28 provides a cross-sectional view of vertical taps for testing purposes.

FIG. 28 provides a cross-sectional view of vertical taps 1004 (or stacked plugs) for testing purposes. The vertical taps shown here are contained in the scanned swath of the exemplary product chip 1000. Shown is the substrate 1003 of the product chip. As shown, the vertical taps or stacked plugs 1004 may be used monitor buried layer M1. Such vertical taps are but one type of test device that can (if desired) be fabricated in the scanned swath.

Figure 29:
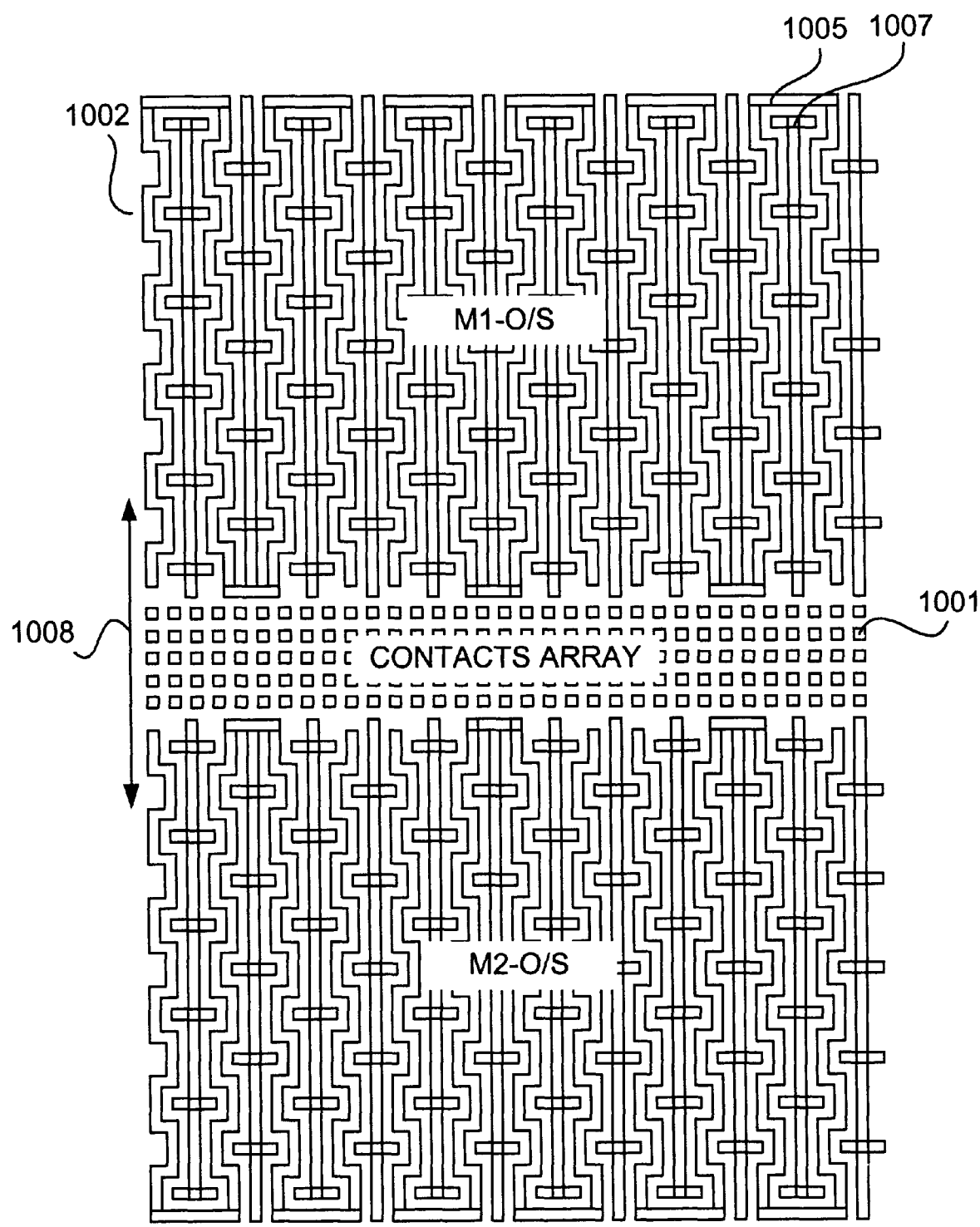
FIG. 29 shows test structures that can be included in a scanned swath.

FIG. 29 shows test structures that can be included in the scanned swath 1002. Included is a contacts array 1006 and conductive lines alternately connected to ground 1005 and left floating 1007. All of these structures can be tested using conventional voltage contrasting techniques, as well as the novel techniques described herein. In a specific embodiment, a scanning device with a continuously moving stage, such as the type described above, will be used to scan the test structures shown in FIG. 29. The preferred direction of continuous motion is illustrated by the arrow 1008, although the continuous motion can be in another direction. Here, however, in order to take only a narrow strip of the product chip for testing purposes, the conductive lines are preferably scanned with the continuous motion being substantially parallel to the conductive lines rather than substantially perpendicular to the conductive lines (as is preferably applied in the context of a dedicated test chip where space is less of a concern).

Once the scanned swath of a product chip has been inspected using voltage contrast techniques at an inspection station, the total defects number of defects can be counted. When a sample stage is continuously moved in a first direction through the primary scan area to detect shorts, for example, the number of open shorts can be quickly quantified. An algorithm can then be applied to infer the expected impact on yield for the product die and this may be used to produce a defect control limit for each defect type at that layer. For example, if there are "n1" opens in an opens test structure that has a critical area "A1" to open shorts per die, then the expected defect level in the product die is given by (n1)*(A1/A2), where A2 is the critical area of the product die for open shorts at the given process layer. The critical area for a given process layer is defined as the total area of the pattern that would result in a failed device for a defect of a given type at the critical dimension.

Once this control is established, if the defect level measured on subsequent lots via scanning of the scanned swath of subsequent product chips exceeds the control limit, the manufacturer will know that its manufacturing process is trending out of control. Further, the manufacturer will have direct feedback from the scanning of the scanned swath as to which defect mechanism is causing the problem. Since the test structures of the scanned swath provide directly the classification of the defect, by the location and signature of the defect in a given test structure, the manufacturer is able to immediately diagnose the problem and fix it.

N. Utilization of Voltage Contrast Testing to Optimize Other Test Devices

The voltage control testing devices, configurations and techniques described above also can be utilized to optimize other inspection systems used during the manufacturing process. Such inspection systems include, for example, KLA-Tencor products AIT II (Patterned Wafer Inspection System) and the KLA-2138 (Wafer Inspection System with UlTra-Broadband Technology). Such systems detect many defects in semiconductor chips. However, some of these detected defects may not be significant in that they do not affect the performance or operation of chips. Voltage contrast testing, on the other hand, by its nature, identifies only significant defects (so-called "killer defects"). Therefore, the voltage contrasting techniques and structures described above can be used to optimize other testing systems so that such systems maximize the detection of "killer defects" and/or minimize the detections of "nuisance defects."

Such optimization will include doing the following operations:

1. A test chip or test portion of a product chip will be inspected by an SEM inspection device in order to detect significant defects;
2. test structures with defects will then be further scanned in order to locate the defect and classify the defect according to its class (e.g., "open," "short" or "via open") to produce a wafer map of significant defects by class;
3. the same test chip or test portion of a product chip is then inspected by the inspection tool to be optimized;
4. preferably, the step 3 is repeated several times with the inspection tool set at differing configurations;
5. defect map(s) are generated based on the inspections using the inspection tool to be optimized;
6. the various defect maps are each overlaid with the wafer map generated by the voltage contrast testing and analyzed to determine which configuration of the inspection tool maximizes capture of significant defects while minimizing capture of insignificant defects; and
7. the inspection tool is set to the optimal configuration.

The inspection tool may generate its defect map from a different layer than the layer on which the voltage contrast defect maps are generated. The above described procedure may also be used to periodically calibrate or spot check the inspection tool.

The process can also be automated using standard automatic nuisance filtering techniques and assign the "killer"

defects as real and the other defects as nuisance and allow the automatic Segmented Autothreshold and Real Time Classification algorithms to configure the tool to maximize the capture of the "killer" defects and minimize the capture of the nuisance defects. See, e.g., U.S. Provisional Patent Application No. 60/167,955 filed on Nov. 29, 1999 by inventors Bakker et al., entitled "POWER ASSISTED AUTOMATIC SUPERVISED CLASSIFIER CREATION TOOL FOR SEMICONDUCTOR DEVICES," which is incorporated herein by reference in its entirety.

One example of a system that can be used to automate this process is KLA-Tencor's product Klarity. Klarity is KLA-Tencor's automated defect data analysis solution. It allows semiconductor fabrication facilities to automate analysis of defect data generated by inspection, classification and review tools. This yield analysis module allows users to automate complex engineering methodologies using simple flowcharts in effect, transferring expert engineering knowledge and defect analysis routines to fab operators. Such automation enables the user to quickly analyze huge volumes of defect data and helps reduce the defect data set to represent only the most critical yield deterrents.

The voltage contrasting techniques, structures and devices described above can also be utilized in conjunction with defect classification methods. For example, the voltage contrasting techniques, etc. can be used in conjunction with the methods and apparatus described in the U.S. Provisional application referenced above and incorporated herein. In one embodiment, electrical (or voltage contrast) data and optical images are sorted and grouped by defect type. The electrically obtained defect information may then be used to characterize the optical images (e.g., sort into killer and non-killer defects) during the setup phase of an optical inspection. Furthermore, wafer maps generated as a result of the inventive voltage contrasting techniques described above can be studied and analyzed to find systematic defects. For example, if the wafer maps of several test chips show that defects are frequently located in a particular area of tested chips, it may indicate a systematic problem in that particular location.

The wafer defect maps that are generated from voltage contrast measurements may also be used in other inspection or review tools. For example, the defect map is generated on a first inspection tool, and the defect map is then used to locate the defects on a second inspection or review tool. For example, a focused ion beam tool may be used to uncover and view the defect, as described above. In sum, the defect map may be used to determine the defect's location after the sample is removed from the voltage contrast tool.

Figure 34:
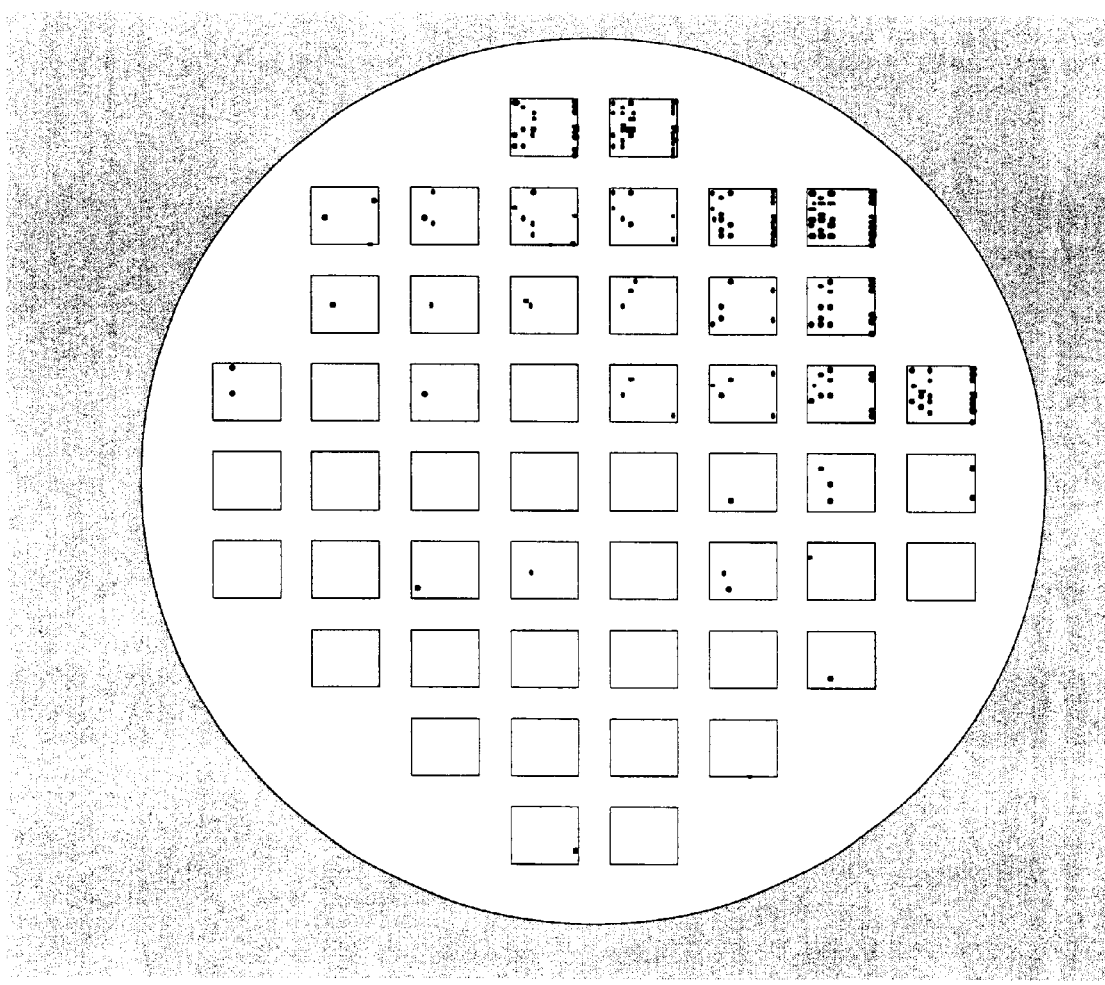
FIG. 34 is an example of a defect that forms an edge type pattern.

Further, certain patterns may emerge in the wafer maps that identify a particular defective (or out of specification) manufacturing process. That is, the particular physical arrangements of the defects on the sample may indicate the type of defect. An example of a defect that forms an edge type pattern is shown in FIG. 34. A particular type of fabrication process will typically have a particular defect footprint. For example, defects that are arranged in patterns that radiate from the center of the chip may indicate a problem with equipment that spins a particular layer onto the wafer. The defect shown in FIG. 34 may originate from an etch process in which the etch tool has a gas entry port on one side of the wafer and a gas exhaust port on the opposite side of the wafer. Thus, a particular arrangement of defects can then be compared and matched to a particular equipment footprint and corresponding process step. In addition, the defect data maps from several wafers across several lots can be stored in a database, and signature analysis applied across the large data set. This would allow one to detect low level signatures in the data that are indicative of systematic process yield problems. A processor may be utilized to efficiently compare the defect data maps to signature patterns. Of course, a user may also manually compare the maps to signatures. By way of another example, the voltage contrast data may be utilized in conjunction with optical data to determine which manufacturing process to inspect so that the capture of killer defects is maximized.

Electrical defect data from a voltage contrast inspection may also be associated with other types of data taken during various steps in the fabrication process. For example, electrical defect data and a corresponding optical image may be generated from a test structure after each process step. Each electrical defect is then characterized and associated with one or more optical images. Process information (e.g., identity of process step and the process machine's operating parameters) may also be associated with the each associated pair of electrical defect and optical image. The evolution of a defect may then be traced through the defect's corresponding optical images. For example, a defect that appears after a particular process may result from such process. The process may then be adjusted (e.g., the operating conditions are adjusted). Additionally, once a particular defect type is associated with a particular optical image, any subsequent optical images that are characterized as being the same as the previous optical image can also be identified as having the same defect type as the previous optical image.

O. Alternative Test Structures

Figure 30:
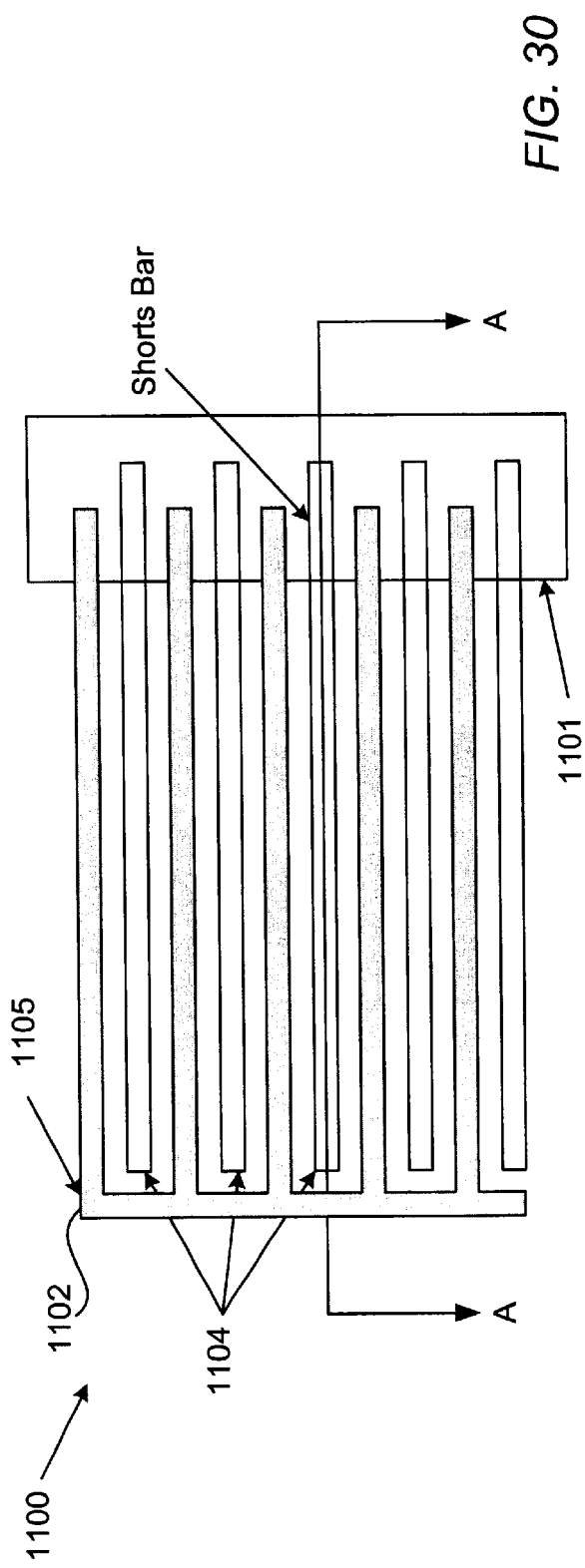
FIG. 30 illustrates a test structure having a plurality of straight and uniform-width lines.

The above described test structures are merely illustrative and are not meant to limit the scope of the invention. For example, any suitable test structure may be utilized that facilitates efficient inspection mechanisms. For example, a test structure may simply be a plurality of straight and uniform-width lines. This configuration is in contrast to the alternating island and conductive line test structure illustrated in FIGS. 5 and 6a. FIG. 30 illustrates such a test structure 1100. This test structure 1100 includes alternating floating conductive lines 1104 and grounded conductive lines 1102. In this embodiment, the lines are substantially straight. One end (1105) of the conductive lines 1102 is tied to ground, while the other end of both conductive lines 1102 and 1104 project into the scan area 1101. The lines projecting into the scan area may have varying lengths to distinguish between the two sets of conductive lines (i.e., 1104 and 1102). Of course, the two sets of lines 1102 and 1104 may have the same length.

As described above, opens within the conductive lines 1102 may be detected by performing voltage contrast on the conductive line ends within the scan area 1101. Likewise, opens between a conductive line 1104 and an adjacent conductive line 1102 may also be detected by performing voltage contrast on the conductive line ends 1104 within scan area 1101. Additionally, stacked plugs as described above with reference to FIGS. 8 through 13 may also be utilized in conjunction with the structure of FIG. 30. As described above, a stacked plug may be used to monitor a buried conductive layer (e.g., for opens).

Figure 31:
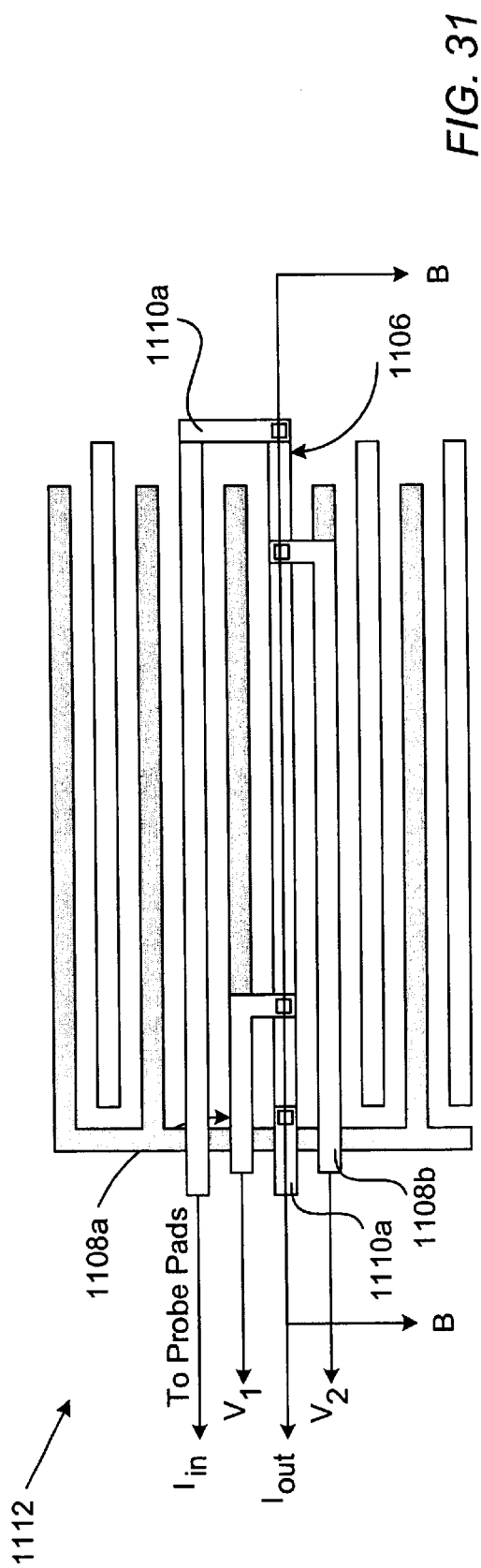
FIG. 31 illustrates a CMP test structure for measuring CMP line thickness.

The test structures that are positioned partially within the scan area 1101 may also be utilized to measure other characteristics, in addition to shorts and opens. For example, the test structures may be utilized to measure various process parameters, such as CMP parameters. FIG. 31 illustrates a CMP test structure 1112 utilized to measure CMP line thickness. As shown, a routing metal layer is utilized to connect a conductive line 1106 formed during a CMP process to four probe pads (not shown). Specifically, a first routing strip 1110*a* and a second routing strip 1110*b* are utilized to force a current through an end of the conductive strip 1106 and out through the opposite end of the conductive strip. That is, a current source is coupled between two probe pads coupled via the first and second routing strips 1110 to each end of the conductive strip 1106. A third and fourth strip are then utilized to measure a voltage difference between each end of the conductive line 1106. A resistance value for the conductive line 1106 may then be calculated based on the measured voltage difference and current value. The width of the conductive line 1106 may then be derived from the resistance value to determine how much erosion and/or dishing has occurred in the conductive line 1106 during the CMP process.

Probe pads may be coupled to any of the above described test structures, as well as the CMP test structure of FIG. 31. These probe pads may then be utilized to measure parametric data regarding the test structure. The parametric data may be utilized with the voltage contrast defect data to determine various characteristics regarding the test structure. For example, if it is determined that a particular conductive line of the test structure is shorted with an adjacent grounded line, the line may be probed to determine a leakage current value. Additionally, various mixed signal tests may be performed via the probe pads.

FIG. 32 illustrates a serpentine type test structure 1200 that may also be utilized to measure line resistance. As shown, the test structure 1200 includes a plurality of first scan elements 1202 and a second plurality of second scan elements 1204. Each of the first scan elements is formed from a stacked plug coupled to the M1 layer 1210. The M1 layer 1210 forms a serpentine pattern that is coupled to ground through vias 1212. Each of the second scan elements 1204 is formed from an M3 conductive line coupled to an M2 conductive line. The second scan elements 1204 are floating.

When voltage contrast is performed on the first scan elements 1202, each first scan element 1202 is expected to have a different brightness since each first scan element has a different line length relative to the grounded vias 1212. For example, the first scan element 1202*c* is expected to have a brightness level of 100% since this element is coupled directly to ground. The first scan elements 1202*b* and 1202*d* to either side of element 1202*c* are expected to have a 50% brightness level, while the first scan elements 1202*e* and 1202*a* are expected to have a 25% brightness level. Since brightness level is also related to line width, the measured brightness level for each first scan element 1202 may be used to calculate line width deviation and/or line resistance.

When voltage contrast is performed on the second scan elements 1204, shorts between M2 and M1 may be monitored. That is, since the second scan element is expected to be electrically isolated from the underlying M1 layer 1210, the second scan element is expected to appear dark. When the second scan element is bright under voltage contrast, a short has occurred between the second scan element 1204 and the underlying M1 layer 1210.

The test structures described above are arranged to facilitate voltage contrast measurement during a continuous scan through the primary scan area (as described above). That is, voltage contrast readings are taken from a plurality of conductive lines as the electron beam moves continuously across the ends of the conductive lines. In an alternative embodiment, test structures may be utilized that facilitate stepper movement techniques to obtain voltage contrast data. For example, stepper type test structures may be utilized with a stepper type SEM, such as the KLA-Tencor 8100 or eV300, Schlumberger, AMAT SEMvision, or Hitachi CD tool.

Figure 33:
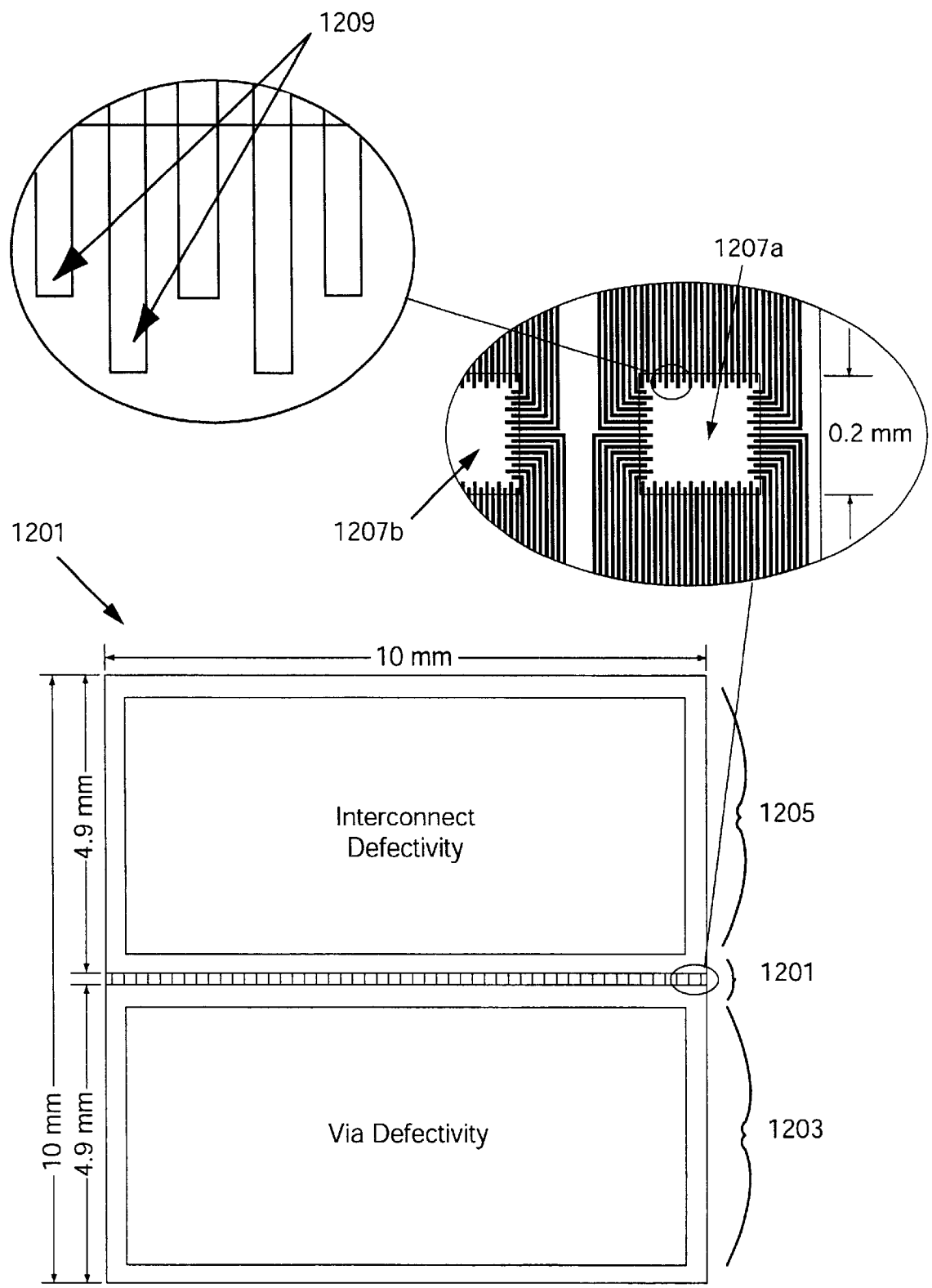
FIG. 33 illustrates test structures suitable for stepper-type techniques.

FIG. 33 illustrates test structures 1201 suitable for stepper-type techniques. Since voltage contrast measurements are performed on one group of test structures at a time, the test structures are arranged into voltage contrast groups. Thus, a first voltage contrast measurement may be conducted on a first group; then on a second group; etc. As shown, the test structures 1201 include a primary scan area 1201 and two secondary scan areas 1203 and 1205. The primary scan area 1201 includes a plurality of test fields (e.g., 1207*a* and 1207*b*) arranged in an array across the primary scan area 1201. A plurality of conductive line ends terminate within each test field 1207. A first portion of the conductive lines extends into the secondary scan area 1203, and a second portion extends into secondary scan area 1205.

Each test field 1207 is sized to facilitate a raster scan of substantially the entire test field without moving the sample stage. For example, the test field is sized such that a raster scan of the field area results in a relatively clear image of the line ends that terminate within the test field 1207. The field area size depends on the particular requirements of the stepper type SEM. Preferably, the test fields are substantially equally spaced from each other to allow a same stepper distance from one field to the next field. The test structures may be arranged in any suitable pattern, such as a two dimensional array or a check board pattern.

The secondary scan areas may include any suitable type of test structures. As shown, the secondary scan area 1205 is arranged for detection of interconnect defects (e.g., opens and shorts) as described above. Secondary scan area 1203, on the other hand, is arranged for detection of via defects as described above. In the illustrated embodiment, the secondary scan areas 1203 and 1205 includes alternating conductive lines of floating and grounded lines. A first end of each conductive line stretches into the secondary scan area, while a second ends extends into the test field 1207. Additionally, the first ends of the grounded lines are grounded. During a voltage contrast inspection within the test field 1207, the second ends of the grounded conductive lines are expected to have a different brightness than the second ends of the floating lines. For example, the grounded line ends appear bright and the floating line ends appear dark. When there is an open defect in one of the grounded conductive lines, the defective line appears a same brightness as an adjacent floating line (e.g., dark). When there is a short between one of the floating conductive lines and a grounded line, the shorted floating line will appear a same brightness as the grounded line (eg., bright). In sum, when a particular line is defective, it's scanned second end will appear to have a n unexpected brightness level. The defect position may then be found by stepping down the particular defective conductive line.

The stepper type test structures (e.g., FIG. 33) may be inspected in any suitable manner that facilitates determining whether there are any defects within a test structure by scanning only a portion of the test structure and then determining a specific location of the defect by scanning the remainder of the test structure. By way of example, the following inspection procedures may be utilized:

1. pre-align wafer to facilitate location of conductive line groups;
2. the conductive line ends are initially positioned under the SEM column by moving the wafer stage; (or the SEM column is positioned over a first group of conductive line ends)
3. an electron beam is scanned over the first group to obtain voltage contrast data;
4. a list of defect data and its associated stub (conductive line end) are stored; and 5. steps 1–4 are repeated for a second group of conductive line ends.

The pre-alignment is performed in any suitable manner so that the SEM is able to automatically step to each group of conductive line ends (herein referred to as "fields"). For example, a step size is entered to ensure that the right step is taken to get from one field to another field. The stage is then automatically stepped from field to field.

A list of defects for each field may be recorded. The defects may then be located in each group of conductive lines associated with each defective field based on the recorded list. For example, the stage is repositioned so that the SEM column is stepped along a longitudinal axis of a defective conductive line. Alternatively, the defects field under test may be located prior to moving to the next field. In this embodiment, a list of defects and their associated stubs may also be recorded for each field. Additionally, the specific defect locations may be recorded for each field.

A defect in a defective line may be found in any suitable manner. In one embodiment, a portion of the defective line that is nearest and outside of the field is positioned under the SEM column. Voltage contrast data is then taken for this portion to determine, for example, if there is a transition from bright to dark within the defective line. The brightness transition position correlates to the position of the defect. If there is no transition within this portion, a next portion that is adjacent to the previously scanned portion of the defective line is positioned under the SEM column.

Alternatively, any suitable search algorithm may be utilized to position portions of the defective line under the SEM column. In a binary search example, a mid-portion between the ends of the defective line is initially positioned under the column. If there is no brightness transition, it is then determined whether the defect is in a first half of the line nearest the field or the other half of the line. For example, if the line is expected to be grounded at the end that is farthest from the field and the mid-portion of the line appears dark, it is determined that the defect is probably located in the half of the line that is farthest from the test field. The search continues on a half portion of the currently searched portion (e.g., a quarter portion of the line is searched next) until the defect is found. A binary defect search mechanism may also be implemented with any other test structures described herein (e.g., the structure of FIGS. 6a–6c or 33).

As described above, the defect's location may also be approximated based on the brightness level in the scanned end. The wafer under test is pre-charged with a dose that is selected to partially charge the structures. Shorter lines will have less capacitance loading and will be charged more completely to an equilibrium potential. Thus, the potential of floating lines will vary approximately linearly with the length of the line. Longer lines will take longer to charge. For example, a length of a floating conductive line with an open defect may be determined from the amount of charging or brightness level of the scanned end.

Shorts between adjacent lines may be quickly found by scanning between the lines, rather than over a single conductive line. For example, a non-raster e-beam may be used to scan, e.g., in a single line scan, between two adjacent and shorted conductive lines. Preferably, the spot size of the e-beam has a radius that is less that the distance between the two adjacent lines. As the e-beam scans between the lines, a significant change in the intensity level of the scan area (e.g., the scan area goes from bright to dark or from dark to bright) indicates the position of the short between the adjacent lines.

Each described test structure may also include a guard ring or one or more conductive structures to control the electrical field of conductive lines and thereby improve detectability of defects. Otherwise, a conductive structure that is not adjacent to another conductive line (e.g., an edge line within a test structure array or a stub that is longer than adjacent stubs) may appear brighter (due to a large edge effect) than a conductive line that is adjacent to another conductive line. In sum, one or more conductive portions that are not under test are used to control the electric field within one or more conductive portions that are under test. In one embodiment, conductive "guard" structures are placed adjacent to specific conductive portions within the test structure that are not located next to other conductive portions of the test structure. The guard structure may be charged to a predefined potential (e.g., grounded) or left floating. Preferably, each guard structure has a different potential than the adjacent conductive line from the test structure. For example, a floating guard structure is positioned adjacent to a grounded conductive line of the test structure.

Figure 35:
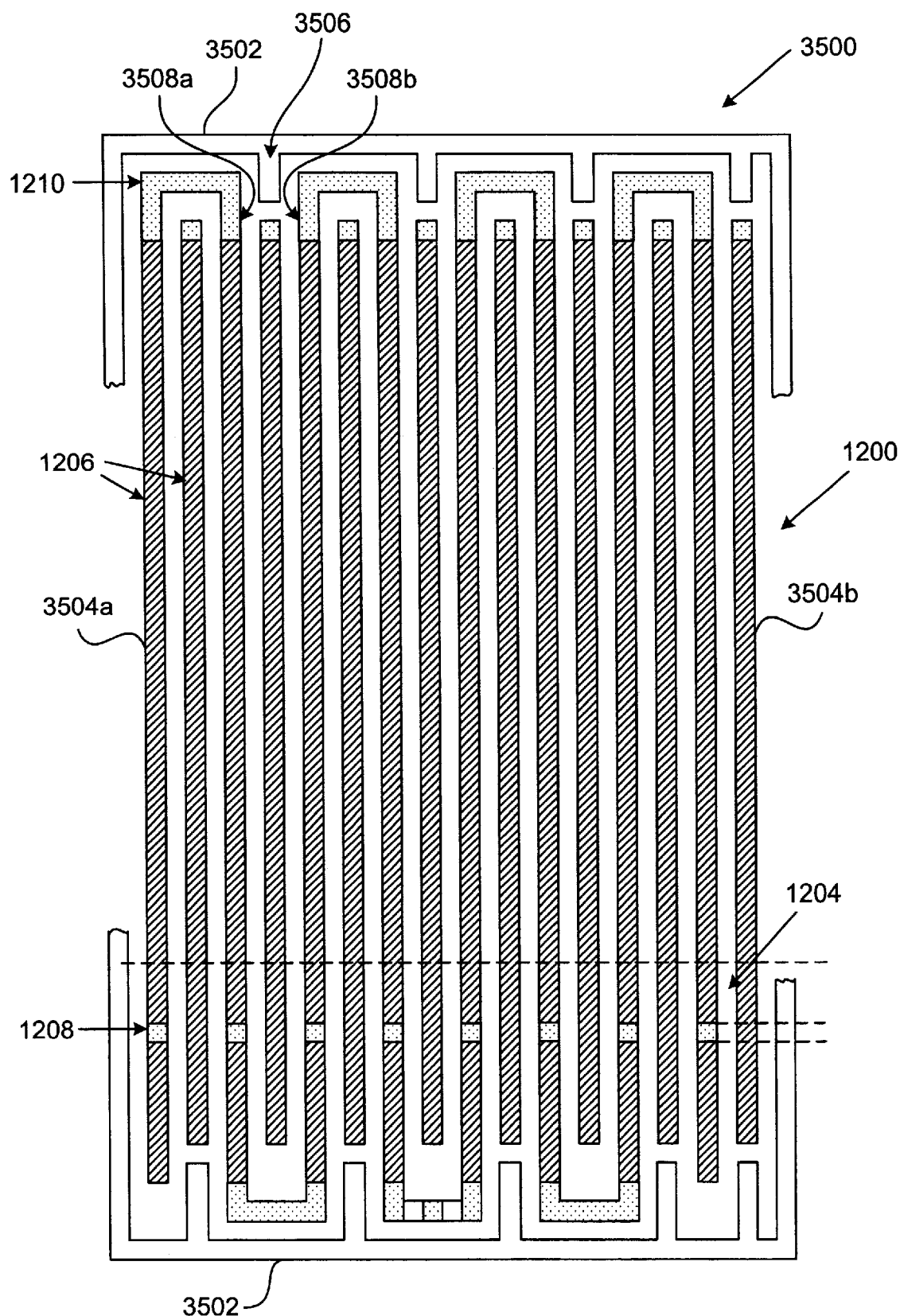
FIG. 35 is a diagrammatic representation of the test structure of FIG. 32 with the addition of a conductive guard ring.

FIG. 35 is a diagrammatic representation of the test structure of FIG. 32 1200 with the addition of a conductive guard ring 3502. The guard ring 3502 encircles the test structure 1200 so that portions of the guard ring are adjacent to outside portions of the test structure. In the illustrated embodiment, the guard ring is adjacent to outside conductive portions 3504*a* and 3504*b*. The guard ring 3502 also includes finger-like portions (e.g., 3506) that are adjacent to portions of the test structure that do not extend along the entire length of an adjacent other structure (e.g., stubs 3508*a* and 3508*b*). A similar guard ring structure may also be utilized with other test structures described herein (e.g., the structures of FIGS. 6a–6c and 33).

In another embodiment, a strip may be placed down the center of the primary scan area to facilitate random mode alignment. When the features of a scan area are very repetitive and small, image aliasing increases and alignment is difficult. Accordingly, one or more large and unique feature may be placed within the scan area in the x and y directions to be used for alignment in the x and y direction.

Although the foregoing invention has been described in some detail for purposes of clarity of understanding, it will be apparent that certain changes and modifications may be practiced within the scope of the appended claims. It should be noted that there are many alternative ways of implementing both the process and apparatus of the present invention. For example, prior to performing a scan in a primary scan area (e.g., 300 $\mu$m), a large area of the wafer (e.g., 10 mm) may be pre-charged with a flood gun to establish voltage contrast equilibrium over the test structures of the wafer. As a result, the amount of time for inspecting the primary scan areas of the test structures may be significantly reduced. By way of another alternative embodiment, the test structures of the present invention may also be utilized in any suitable critical dimension measurement tool. That is, the test structures may be formed with structures having critical dimensions (e.g., minimum line width and line-to-line spacing).

Any other suitable charge control mechanisms may also be utilized for inspecting the above-described test structures. Several mechanisms for controlling charge are described in co-pending U.S. patent application Nos. 09/579,867, 09/502,554, and 09/394,133 and U.S. Pat. No. 6,066,849, which applications and patent are herein incorporated by reference in their entirety. Additionally, any suitable charged particle beam (e.g., electron beam) inspection system and/or methodologies may be used to inspect the above described test structures and to implement the above described inspection methods (e.g., e-beam systems and/or methods described in U.S. patent application Nos. 09/579,867, 09/502,554, and 09/394,133 and U.S. Pat. No. 6,066,849). Although the test structure embodiments are described above as being inspected with an electron beam system, of course, other types of systems may be utilized. For example, a photo emission system (constant or pulsed beam) may work well for charging selected portions of the test structures for voltage contrast analysis. Other systems may be used in conjunction with (e.g., off-column) or in place of an electron beam system.

The mechanisms of the present invention may be implemented for any suitable application, besides semiconductor chip manufacturing. For example, other applications are data disks, gallium arsenide semiconductor devices, and multichip modules. In general terms, the embodiments of the present invention may be applied to any suitable technology for manufacturing electronic devices or any other type of objects having fine patterns. Furthermore, techniques for characterizing defects and/or creating an x and y map of defects may also be applied across an entire wafer to facilitate detection of systematic process problems. In other words, defects may be mapped across the wafer. When an specific area of the wafer is found to have a significantly higher number of defects than other areas, it may be determined that a process is performing improperly for such specific area. The process may then be adjusted to subsequently reduce defects in such specific area of the wafer. Additionally, the above described test structures may be formed on any suitable portion of the wafer, such as within the scribe line or on any portion of one or more dice.

Accordingly, the present embodiments are to be considered as illustrative and not restrictive, and the invention is not to be limited to the details given herein, but may be modified within the scope and equivalents of the appended claims.

What is claimed is:

1. A method of forming a semiconductor die having a scanning area, the method comprising:

forming a first plurality of test structures entirely within the scanning area;

forming a second plurality of test structures partially within the scanning area; and scanning the scanning area with an electron beam to detect defects outside of the scanning area.

2. The method of claim 1, wherein the first plurality of test structures comprises test structures that are electrically isolated and others that are not.

3. The method of claim 1 wherein the second plurality of test structures comprises test structures that are electrically isolated and others that are not.

4. The method of claim 1 the first plurality of test structures comprises test structures that are electrically isolated and others that are not and the second plurality of test structures comprises test structures that are electrically isolated and others that are not.

5. The method of claim 1 wherein the second plurality of test structures comprises test structures that are primarily located outside the scanning area.

6. A method as recited in claim 5 wherein the second plurality of test structures are arranged such that a short associated with a portion of the second plurality of test structures that is located outside the scanning area is detectable by performing voltage contrast on a portion of the second plurality of test structures that is located within the scanning area.

7. The method of claim 1 further comprising forming product circuitry on the semiconductor die outside of the primary scan area.

8. The method of claim 1 wherein the scanning area is located in the middle of semiconductor die.

9. The method of claim 1, further comprising forming a wafer from the plurality semiconductor dies.

10. A method as recited in claim 1, wherein at least two of the scanning areas from two of the semiconductor dies are aligned along their longitudinal axis.

11. The method of claim 1, wherein the semiconductor die has a plurality of scanning areas.

12. The method of claim 1, wherein the second plurality of test structures form a rectangular shape and the scanning areas are arranged to optimize an aspect ratio of the second plurality of test structures of each scanning area.

13. The method of claim 1, wherein the scanning areas are arranged in a checkerboard pattern.

14. The method of claim 1, wherein the first plurality of test structures include a mix of test structure types.

15. The method of claim 11 wherein the first plurality of test structures include a first type of test structure and a second type of test structure, the first type differing from the second type, and the first and second test structures are selected from a group consisting of a via chain test structure, a chemical mechanical polishing (CMP) test structure, a contact array test structure, a test structure for measuring misalignment, and a CMP dummy metal filler test structure.

16. The method of claim 15, wherein the CMP test structure is arranged for measurement of a CMP parameter selected from a group consisting of a pitch value, a density value, and a horizontal aspect ratio value.

17. The method of claim 1, wherein the first plurality of test structures form a contiguous single structure that is coupled to a predefined voltage potential and the second plurality of test structures form a plurality of separate lines interleaved between portions of the first test structures.

18. The method of claim 17, wherein the first test structures form a serpentine shaped structure and includes one or more contacts that are coupled to the predefined voltage potential.

19. The method of claim 18, wherein the one or more contacts are located within the middle of the first test structures and is coupled to a ground potential, the second test structures being designed to be floating.

* * * * *